US012109410B2

(12) United States Patent
Leonhardt et al.

(10) Patent No.: US 12,109,410 B2
(45) Date of Patent: Oct. 8, 2024

(54) BIOELECTRIC STIMULATOR

(71) Applicant: LEONHARDT VENTURES LLC, Corona Del Mar, CA (US)

(72) Inventors: Howard J. Leonhardt, Corona Del Mar, CA (US); Jorge Genovese, Buenos Aires (AR)

(73) Assignee: LEONHARDT VENTURES LLC, Corona Del Mar, CA (US)

(*) Notice: Subject to any disclaimer, the term of this patent is extended or adjusted under 35 U.S.C. 154(b) by 326 days.

(21) Appl. No.: 17/216,423

(22) Filed: Mar. 29, 2021

(65) Prior Publication Data

US 2021/0236817 A1 Aug. 5, 2021

Related U.S. Application Data

(63) Continuation of application No. 15/812,760, filed on Nov. 14, 2017, now Pat. No. 10,960,206, which is a (Continued)

(51) Int. Cl.
*A61N 1/32* (2006.01)
*A61B 5/243* (2021.01)
(Continued)

(52) U.S. Cl.
CPC ......... *A61N 1/326* (2013.01); *A61M 39/0208* (2013.01); *A61N 1/37205* (2013.01);
(Continued)

(58) Field of Classification Search
CPC .... A61N 1/326; A61N 1/37205; A61N 1/375; A61N 1/36002; A61N 1/36007;
(Continued)

(56) References Cited

U.S. PATENT DOCUMENTS

D263,073 S 2/1982 Jonkers et al.
D273,893 S 5/1984 Weitzman
(Continued)

FOREIGN PATENT DOCUMENTS

AU 2019363173 A3 4/2020
CA 2685161 A1 10/2007
(Continued)

OTHER PUBLICATIONS

Mei al. "Combined effect of rhTGF-β1 and rhPDGF-BB on the expression of Pyk2 protein and mRNA gene during orthodontic tooth movement in SD rats" Shanghai Kou Qiang Yi Xue. Oct. 2019;28(5):472-477. Chinese. PMID: 32274476.
(Continued)

*Primary Examiner* — Mark W. Bockelman
(74) *Attorney, Agent, or Firm* — TraskBritt

(57) ABSTRACT

Described is a low voltage, pulsed electrical stimulation device for controlling expression of, for example, follistatin, a muscle formation promotion protein, by tissues. Epicardial stimulation is especially useful for heart treatment. Follistatin controlled release is also useful for treating other ailments, such as erectile dysfunction, aortic aneurysm, and failing heart valves.

15 Claims, 19 Drawing Sheets

Related U.S. Application Data continuation-in-part of application No. 15/460,129, filed on Mar. 15, 2017, now Pat. No. 10,646,644.

(60) Provisional application No. 62/454,521, filed on Feb. 3, 2017, provisional application No. 62/385,124, filed on Sep. 8, 2016, provisional application No. 62/375,271, filed on Aug. 15, 2016, provisional application No. 62/364,472, filed on Jul. 20, 2016, provisional application No. 62/363,012, filed on Jul. 15, 2016, provisional application No. 62/352,930, filed on Jun. 21, 2016, provisional application No. 62/308,702, filed on Mar. 15, 2016.

(51) Int. Cl.
*A61M 5/142* (2006.01)
*A61M 39/00* (2006.01)
*A61M 39/02* (2006.01)
*A61N 1/36* (2006.01)
*A61N 1/362* (2006.01)
*A61N 1/372* (2006.01)
*A61N 1/375* (2006.01)

(52) U.S. Cl.
CPC .............. *A61N 1/375* (2013.01); *A61B 5/243* (2021.01); *A61M 5/14276* (2013.01); *A61M 2039/0036* (2013.01); *A61M 2202/07* (2013.01); *A61M 2205/05* (2013.01); *A61M 2205/50* (2013.01); *A61M 2205/502* (2013.01); *A61N 1/36002* (2017.08); *A61N 1/36007* (2013.01); *A61N 1/36071* (2013.01); *A61N 1/36114* (2013.01); *A61N 1/3629* (2017.08)

(58) Field of Classification Search
CPC ............ A61N 1/36071; A61N 1/36114; A61N 1/3629; A61M 39/0208; A61M 5/14276; A61M 2039/0036; A61M 2202/07; A61M 2205/05; A61M 2205/50; A61M 2205/502; A61B 5/243
See application file for complete search history.

(56) References Cited

U.S. PATENT DOCUMENTS 4,622,952 A 11/1986 Gordon
4,976,733 A 12/1990 Girardot
5,135,478 A 8/1992 Sibalis
5,211,622 A 5/1993 Liboff et al.
5,295,958 A 3/1994 Shturman
5,543,318 A 8/1996 Smith et al.
5,555,883 A 9/1996 Avitall
5,693,029 A 12/1997 Leonhardt
5,713,917 A 2/1998 Leonhardt et al.
5,725,377 A 3/1998 Lemler et al.
5,817,139 A 10/1998 Kasano
5,957,949 A 9/1999 Leonhardt et al.
6,047,700 A 4/2000 Eggers et al.
6,344,052 B1 2/2002 Greenan et al.
6,618,625 B2 9/2003 Silverstone
6,957,106 B2 10/2005 Schuler et al.
6,988,004 B2 1/2006 Kanno et al.
7,029,276 B2 4/2006 Mao
7,136,699 B2 11/2006 Palti
7,341,062 B2 3/2008 Chachques et al.
7,483,749 B2 1/2009 Leonhardt et al.
7,686,799 B2 3/2010 Leonhardt et al.
7,881,784 B2 2/2011 Pasricha et al.
8,041,428 B2 10/2011 Errico et al.
8,133,267 B2 3/2012 Leonhardt et al.
8,166,976 B2 5/2012 Webster et al.
8,226,407 B2 7/2012 Hanewinkel et al.
8,465,533 B2 6/2013 Palti
8,534,289 B2 9/2013 Hernandez
8,639,361 B2 1/2014 Nathanson
8,646,455 B2 2/2014 Webster et al.
8,656,930 B2 2/2014 Schuler et al.
8,660,669 B2 2/2014 Nemeh et al.
8,738,144 B2 5/2014 Schneider
8,909,346 B2 12/2014 Chalmers
8,945,104 B2 2/2015 Boone et al.
9,032,964 B2 5/2015 Poliner et al.
9,173,811 B2 11/2015 Greiner et al.
9,533,170 B2 1/2017 Dye et al.
9,545,331 B2 1/2017 Ingemarsson-Matzen
D778,449 S 2/2017 Ingemarsson-Matzen
9,656,096 B2 5/2017 Pilla
9,662,184 B2 5/2017 Lowe
9,687,383 B2 6/2017 Ingemarsson-Matzen
9,707,403 B2 7/2017 Schuler
9,855,418 B2 1/2018 Haralambidis
9,987,326 B2 6/2018 Koeffler et al.
D832,447 S 10/2018 Wiffen
10,543,119 B2 1/2020 Ingemarsson-Matzen
10,561,836 B2 2/2020 Sama
D881,399 S 4/2020 Ingemarsson-Matzen
10,646,644 B2 5/2020 Leonhardt et al.
10,960,206 B2 3/2021 Leonhardt et al.
11,058,536 B2 7/2021 Huber
11,110,274 B2 9/2021 Leonhardt
2002/0143373 A1 10/2002 Courtnage et al.
2003/0032998 A1 2/2003 Altman
2003/0220556 A1 11/2003 Porat et al.
2004/0010231 A1 1/2004 Leonhardt et al.
2004/0115587 A1 6/2004 Breining et al.
2004/0147906 A1 7/2004 Voyiazis et al.
2004/0236238 A1 11/2004 Schuler et al.
2005/0075679 A1* 4/2005 Gliner ................ A61N 1/36082 607/45
2005/0171578 A1 8/2005 Leonhardt
2006/0030908 A1 2/2006 Powell et al.
2006/0100553 A1 5/2006 Lodin
2006/0116721 A1 6/2006 Yun et al.
2006/0195164 A1 8/2006 Sondergaard et al.
2007/0123758 A1 5/2007 Miesel et al.
2007/0167984 A1 7/2007 Kieval et al.
2007/0190028 A1 8/2007 Qu et al.
2007/0265680 A1 11/2007 Liu
2008/0227046 A1 9/2008 Lowe et al.
2008/0243060 A1 10/2008 Hartmann et al.
2009/0132010 A1 5/2009 Kronberg
2009/0240304 A1 9/2009 Blum et al.
2010/0082027 A1 4/2010 Chalmers
2010/0184183 A1 7/2010 Schussler et al.
2010/0217148 A1 8/2010 Binder
2012/0156648 A1 6/2012 Kaufman et al.
2013/0253413 A1 9/2013 Levine et al.
2014/0023983 A1 1/2014 Lowe et al.
2014/0214115 A1 7/2014 Greiner et al.
2014/0214116 A1 7/2014 Peterson et al.
2014/0214124 A1 7/2014 Greiner et al.
2014/0214144 A1 7/2014 Peterson et al.
2014/0228910 A1 8/2014 Schuler et al.
2017/0028184 A1 2/2017 Godden et al.
2017/0036032 A1 2/2017 Schuler et al.
2017/0112983 A1 4/2017 Thorne et al.
2017/0266371 A1 9/2017 Leonhardt et al.
2017/0274206 A1 9/2017 Leonhardt
2018/0043159 A1 2/2018 Hassan et al.
2018/0064935 A1 3/2018 Leonhardt et al.
2018/0071135 A1 3/2018 Ingemarsson-Matzen
2018/0117322 A1 5/2018 Chang et al.
2018/0193646 A1 7/2018 Fostick et al.
2019/0015661 A1 1/2019 Leonhardt et al.
2019/0022389 A1 1/2019 Leonhardt
2019/0022396 A1 1/2019 Leonhardt
2019/0125932 A1 5/2019 Leonhardt et al.
2019/0255321 A1 8/2019 Planard-Luong
2019/0290541 A1 9/2019 Greiner et al.
2020/0030136 A1 1/2020 Hernandez
2020/0121984 A1 4/2020 Sama
2020/0289826 A1 9/2020 Leonhardt

(56) References Cited

U.S. PATENT DOCUMENTS

| | | | |
|---|---|---|---|
| 2020/0324106 | A1 | 10/2020 | Leonhardt |
| 2020/0330753 | A1 | 10/2020 | Leonhardt et al. |
| 2021/0228870 | A1 | 7/2021 | Leonhardt |

FOREIGN PATENT DOCUMENTS

| | | | |
|---|---|---|---|
| EP | 0603451 | A1 | 6/1994 |
| EP | 3291880 | B1 | 7/2021 |
| GB | 2578310 | A | 5/2020 |
| GB | 2578318 | A | 5/2020 |
| JP | 2013-034881 | A | 2/2013 |
| KR | 10-2007-0010908 | A | 1/2007 |
| KR | 10-0726825 | B1 | 6/2007 |
| WO | 92/17118 | A1 | 10/1992 |
| WO | 2006/116728 | A2 | 11/2006 |
| WO | 2007/146187 | A2 | 12/2007 |
| WO | 2008/145724 | A1 | 12/2008 |
| WO | 2009/021535 | A1 | 2/2009 |
| WO | 2011/016629 | A2 | 2/2011 |
| WO | 2014/172693 | A2 | 10/2014 |
| WO | 2016/135295 | A1 | 9/2016 |
| WO | 2017/142948 | A1 | 8/2017 |
| WO | 2020/079436 | A3 | 4/2020 |
| WO | 2020/185622 | A1 | 9/2020 |

OTHER PUBLICATIONS

Shimamura et al. "OPG/RANKL/RANK axis is a critical inflammatory signaling system in ischemic brain in mice." Proceedings of the National Academy of Sciences of the United States of America vol. 111,22 (2014): 8191-6. doi: 10.1073/pnas.1400544111.

HealthCMI, "Acupuncture Combats Hypertension In University of California Research," Available online at <https://www.healthcmi.com/Acupuncture-Continuing-Education-News/1688-acupuncture-c . . . >, (2016), 9 pages.

HealthCMI, "UC Irvine—Acupuncture Reduces Hypertension Confirmed," Available Online at <https://www.healthcmi.com/Acupuncture-Continuing-Education-News/1792-uc-irvine-acup . . . >, (2017), 6 pages.

Heart Valve Calcifications—Focused Ultrasound TherapyFocused Ultrasound Therapy; Research Paper Last Updated: Jan. 28, 2020, The Focused Ultrasound Foundation Newsletter (5 pages).

Hearts build new muscle with this simple protein patch, jacobsschool.ucsd.edu/news/news_releases/release.sfe?id=1813(Sep. 16, 2015).

Hoffmann, "Regeneration of the gastric mucosa and its glands from stem cells", Curr Med Chem, 15(29):3133-44 (2008).

Holding et al. "The correlation of RANK, RANKL and TNFa expression with bone loss volume and polyethylene wear debris around hip implants" Biomaterials 27(30):5212-9—Nov. 2006.

Holen et al. "Role of Osteoprotegerin (OPG) in Cancer" Clin Sci (Lond). Mar. 2006; 110(3):279-91. doi: 10.1042/CS20050175.

Hopkins Medicine "Overview of Pacemakers and Implantable Cardioverter Defibrillators (ICDs)," hopkinsmedicine.org/healthlibrary/conditions/cardiovascular_diseases/ )verview of pacemakers and implantable cardioverter defibrillators icds 85,P00234/, last visited Sep. 12, 2018.

https://www.dicardiology.com/content/bioleonhardt-unveils-stem-pump Jan. 28, 2014.

Hu et al. "Klotho Deficiency Causes Vascular Calcification in Chronic Kidney Disease" J Am Soc Nephrol. Jan. 2011; 22(1): 124-136.

Hu et al. "Exosomes derived from human adipose mesenchymal stem cells accelerates cutaneous wound healing via optimizing the characteristics of fibroblasts", Nature Scientific Reports, vol. 6, Article No. 32993 (2016).

HU Klein, "Vagus Nerve Stimulation: A new approach to reduce heart failure" Cardiology Journal (2010).

Huang et al. "Myocardial transfection of hypoxia-inducible factor-1a and co-transplantation of mesenchymal stem cells enhance cardiac repair in rats with experimental myocardial infarction", Stem Cell Research & Therapy 5:22 (2014) DOI: 10.1186/scrt410.

Hudson et al. "Local delivery of recombinant osteoprotegerin enhances postorthodontic tooth stability" Calcif Tissue Int. Apr. 2012; 90(4):330-42. doi: 10.1007/s00223-012-9579-4.

Hy et al., "Insulin-like growth factor 1 and hair growth," Dermatol Online J,; 5(2):1 (Nov. 1999).

Iglesias-Linares et al. "The use of gene therapy vs. corticotomy surgery in accelerating orthodontic tooth movement." Orthod Craniofac Res. Aug. 2011; 14(3):138-48. doi: 10.1111/j.1601-6343.2011.01519.x.

Infante et al. "RANKL/RANK/OPG system beyond bone remodeling: involvement in breast cancer and clinical perspectives" Journal of Experimental & Clinical Cancer Research (2019) 38:12. https://doi.org/10.1186/s13046-018-1001-2.

Interesting study about prolactin, VEGF and angiogenic inhibition, http://www.regrowth.com/hair-loss-forums/topic/interesting-study-about-prolactin-vegf-and-angiogenic-inhibition/ (Nov. 2006).

International Search Report for International Application No. PCT/US19/52288, dated Jan. 10, 2020, 11 pages.

International Search Report for International Application No. PCT/US2019/025177, dated Sep. 3, 2019, 3 pages.

International Written Opinion for International Application No. PCT/US19/52288, dated Jan. 10, 2020, 07 pages.

International Written Opinion for International Application No. PCT/US2019/025177, dated Sep. 3, 2019, 5 pages.

Involvement of hepatocyte growth factor/scatter factor and Met receptor signaling in hair follicle morphogenesis and cycling, FASEB J Feb. 2000 14:319-332.

Israeli innovation uses nerve stimulation to treat heart failure https://www.israel21c.org/israeli-innovation-uses-nerve-stimulation-to-treat-heart-failure/ (Feb. 11, 2007).

Istanbullu et al., "Electrochemical Biofilm Control: Mechanism of Action," Biofouling, vol. 28, (2012), pp. 769-778.

Jansen et al. "Stimulation of osteogenic differentiation in human osteoprogenitor cells by pulsed electromagnetic fields: an in vitro study" BMC Musculoskeletal Disorders (2010) 11:188 DOI: 10.1186/1471-2474-11-188.

Jeffrey, "How to Decalcify Your Pineal Gland (And Why It's Really Important for Higher Mental Performance)," (available at https://scottjeffrey.com/decalcify-your-pineal-gland/), Retrieved on May 23, 2019, 23 pages.

Jia et al., "Activin B Promotes Initiation and Development of Hair Follicles in Mice" Cells Tissues Organs, 198:318-326 (Feb. 2014).

Jing-Hong et al. "Electrochemical Therapy of Tumors" Hindawi Publishing Corporation, Conference Papers in Medicine, vol. 2013, Article ID 858319, 13 pages, http://dx.doi.org/10.1155/2013/858319.

Jouybar et al. "Enhanced Skin Regeneration by Herbal Extract-Coated Poly-L-Lactic Acid Nanofibrous Scaffold" Artif Organs. Nov. 2017; 41(11):E296-E307. doi: 10.1111/aor.12926 (Abstract Only).

Jung et al. "Prospective 1-Year Follow-Up Study of Breast Augmentation by Cell-Assisted Lipotransfer" Aesthetic Surgery Journal 2016, vol. 36(2) 179-190 © 2015 The American Society for Aesthetic Plastic Surgery, Inc.

Kanno et al., Establishment of a Simple and Practical Procedure Applicable to Therapeutic Angiogenesis, Circulation, 1999, pp. 2682-2687, vol. 99.

Kanzaki et al. "Local OPG gene transfer to periodontal tissue inhibits orthodontic tooth movement." J Dent Res 2004; 83:92/925.

Kanzaki et al. "Local RANKL gene transfer to the periodontal tissue accelerates orthodontic tooth movement", Gene Therapy, (2006) 13, 678-685.

Kanzaki et al. "Periodontal ligament cells under mechanical stress induce osteoclastogenesis by receptor activator of nuclear factor kappaB ligand up-regulation via prostaglandin E2 synthesis", J Bone Miner Res 2002;17:21 / 220.

Kasimanickam et al., "Prevention and Treatment of Biofilms by Hybrid- and Nanotechnologies," International journal of Nanomedicine, vol. 8, (2013), pp. 2809-2819.

Kaur et al. "Electrically conductive polymers and composites for biomedical applications", RSC Adv., 2015,5, 37553-37567 DOI: 10.1039/C5RA01851J.

(56) References Cited

OTHER PUBLICATIONS

Keles et al. "Inhibition of tooth movement by osteoprotegerin vs. pamidronate under conditions of constant orthodontic force", Eur J Oral Sci. Apr. 2007; 115(2):131-6.
Keunen et al. "Anti-VEGF treatment reduces blood supply and increases tumor cell invasion in glioblastoma," Proc. Natl. Acad. Sci. U. S. A. Mar. 1, 2011; 108(9): 3749-3754, published online Feb. 14, 2011; doi: 10.1073/pnas.1014480108.
Khan et al. "Accelerating Tooth Movement: What Options We Have?" J Dent Health Oral Disord Ther 2016, 5(7): 00181.
Kido et al. "Hypoxia-Inducible Factor 1-Alpha Reduces Infarction and Attenuates Progression of Cardiac Dysfunction After Myocardial Infarction in the Mouse" JACC, vol. 46, Issue 11, Dec. 6, 2005, pp. 2116-2124. https://doi.org/10.1016/j.jacc.2005.08.045.
Kim et al., "Effect of Electrical Energy on the Efficacy of Biofilm Treatment Using the Bioelectric Effect," NPJ Biofilms and Microbiomes, vol. 1, (2015), Article 15016, 8 pages.
Kim et al., The effects of electrical current from a micro-electrical device on tooth movement, http://e-kjo.org/search.php?where=aview&id=10.4041/kjod.2008.38.5.337& . . . visited Aug. 2, 2017.
King et al. "Mechanical Decalcification of the Aortic Valve" 272 The Annals of Thoracic Surgery vol. 42 No. 3 Sep. 1986 (pp. 269-272).
Kinney et al., "High Intensity Focused Electromagnetic Therapy Evaluated by Magnetic Resonance Imaging: Safety and Efficacy Study of a Dual Tissue Effect Based Non-Invasive Abdominal Body Shaping," Lasers in Surgery and Medicine, vol. 51, (2019), pp. 40-46.
Kondo et al. "Types of tooth movement, bodily or tipping, do not affect the displacement of the tooth's center of resistance but do affect the alveolar bone resorption" Angle Orthod Jul. 2017; 87(4):563-569.
Kose et al. "Citric acid as a decalcifying agent for the excised calcified human heart valves" Anadolu Kardiyol Derg 2008; 8: 94-8 (Eng Abstract).
Krishnan et al. (eds.), "Biological Mechanisms of Tooth Movement", John Wiley & Sons 2015 (10 pages).
Lamoureux et al. "Therapeutic Relevance of Osteoprotegerin Gene Therapy in Osteosarcoma: Blockade of the Vicious Cycle between Tumor Cell Proliferation and Bone Resorption" Cancer Res 1 2007 67(15):7308-7318; DOI: 10.1158/0008-5472.CAN-06-4130.
Landau et al. "Review: Proposed Methods to Improve the Survival of Adipose Tissue in Autologous Fat Grafting" Plast Reconstr Surg Glob Open. 2018;6(8):e1870. Published Aug. 3, 2018. doi:10.1097/GOX.0000000000001870.
Sutherland et al. "Prolonged electrical stimulation of the nipples evokes intermittent milk ejection in the anaesthetised lactating rat," Exp Brain Res. 1987;66(1):29-34.
Szkotak et al., "Differential Gene Expression to Investigate the Effects of Low-Level Electrochemical Currents on Bacillus subtilis," AMB Express, vol. 1, (Nov. 2011), 12 pages.
Tajima et al. "HIF-1alpha is necessary to support gluconeogenesis during liver regeneration" Biochem Biophys Res Commun. Oct. 2, 2009; 387(4):789-94. doi: 10.1016/j.bbrc.2009.07.115. Epub Jul. 28, 2009.
Tamaki et al., "Cardiomyocyte Formation by Skeletal Muscle-Derived Multi-Myogenic Stem Cells after Transplantation into Infarcted Myocardium", PloS ONE 3(3): e1789. doi: 10.1371/journal.pone.0001789 (Mar. 2008).
Tan et al. "Bioelectric Perturbations in Orthodontic tooth movement" 2010 Journal of Dental Sciences & Research 1:1: pp. 41-49.
Tan et al., "Acupuncture Therapy for Essential Hypertension: a Network Meta-Analysis," Annals of Translational Medicine, vol. 7, (2019), pp. 1-12.
Tavlasoglu et al. "Is partial decalcification of posterior mitral annular bed logical in all mitral valve replacement procedures?" European Journal of Cardio-Thoracic Surgery 43 (2013) 449-450.
Thattaliyath et al., "Modified Skeletal Myoblast Therapy For Cardiac Failure Using AAV SDF1", Proc. Inti. Soc. Mag. Reson. Med. 16, p. 579 (2008).
Tokyo Medical and Dental University "RANKL expressed by osteocytes has an important role in orthodontic tooth movement" Science Daily Oct. 20, 2017.
Totsugawa, et al. "Ultrasonic annular debridement in minimally invasive aortic valve replacement" Gen Thorac Cardiovasc Surg. Jan. 2020;68(1):81-83. doi: 10.1007/s11748-019-01158-8. Epub Jun. 15, 2019. (Abstract Only).
Trafton, Anne, "A Noninvasive Method for Deep Brain Stimulation," MIT News Office, (available at http://news.mit.edu/2017/noninvasive-method-deep-brain-stimulation-0601), (Jun. 1, 2017), 3 pages.
UCIrvine, "Electroacupuncture for Hypertension in Women: The Susan Samueli Center for Integrative Medicine at UC Irvine is Recruiting Patients for a Study", Principle Investigators: Dr. Stephanie Tjen-a-Looi and Dr. Shaista Malik, MOD# 20266, HS# 1999-2222, (2017), 1 page.
Ueland et al. "Inflammatory cytokines as biomarkers in heart failure," Clinica Chimica Acta, vol. 443, Mar. 30, 2015, pp. 71-77; doi.org/10.1016/j.cca.2014.09.001.
Valvublator Heart Valve Regeneration, accessed Apr. 24, 2020 https://valvublator.com (6 pages).
Van Dam et al. "RANK/RANKL signaling inhibition may improve the effectiveness of checkpoint blockade in cancer treatment" Critical Reviews in Oncology/Hematology vol. 133, Jan. 2019, pp. 85-91.
Verna et al. "The rate and the type of orthodontic tooth movement is influenced by bone turnover in a rat model" European Journal of Orthodontics 22 (2000) 343-352.
Vilela-Martin et al., "Effects of Transcutaneous Electrical Nerve Stimulation (TENS) on Arterial Stiffness and Blood Pressure in Resistant Hypertensive Individuals: Study Protocol for a Randomized Controlled Trial," Trials, vol. 17, (2016), pp. 1-13.
Vinod Krishnan, Ze'ev Davidovitch (eds.), Biological Mechanisms of Tooth Movement, (John Wiley & Sons 2015 (10 Pages).
Wagenseil et al., "Elastin in large artery stiffness and hypertension," Journal of Cardiovascular Translational Research, vol. 5, No. 3, 2012, pp. 264-273, Available online at <https://www.ncbi.nlm.nih.gov/pmc/articles/PMC3383658/ >, 21, pages.
Walsh & Choi "Biology of the RANK* RAN* OPG System in Immunity, Bone, and Beyond", Front Immunol. 2014; 5: 511.
Wang et al. "Local and sustained miRNA delivery from an injectable hydrogel promotes cardiomyocyte proliferation and functional regeneration after ischemic injury", Nat Biomed Eng. 2017; 1: 983-992, doi: 10.1038/s41551-017-0157-y.
Wang et al., "Controlling *Streptococcus mutans* and *Staphylococcus aureus* Biofilms With Direct Current and Chlorhexidine," AMB Express, vol. 7, (Nov. 2017), 9 pages.
Warner "Inflammation Adds to Blood Pressure Risks, High Blood Pressure and C-Reactive Protein May Trigger Heart Attack, Stroke" Art. WebMD Health News (2003) 2 pages.
Wei et al., "Epicardial FSTL1 reconstitution regenerates the adult mammalian heart," Nature 525: 479-485 (Sep. 24, 2015).
Welch "RGS2 Proteins Regulate Blood Pressure" JASN Nov. 2010, 21 (11) 1809-1810.
Wellman et al., "Bacterial Biofilms and the Bioelectric Effect," Antimicrobial Agents and Chemotherapy, vol. 40, (1996), pp. 2012-2014.
What Is Elastin? http://www.keracyte.com/index.php/site/page?view=whatIsElastin.
Wong et al., "Dual Functional Polyelectrolyte Multilayer Coatings for Implants: Permanent Microbicidal Base With Controlled Release of Therapeutic Agents," Journal of the American Chemical Society, vol. 132, (2010), pp. 17840-17848.
Wu et al., "Vascular Calcification: an Update on Mechanisms and Challenges in Treatment," Calcified Tissue International, vol. 93, (Oct. 2013), pp. 365-373.
Xiong et al. "Current understanding of neuroinflammation after traumatic brain injury and cell-based therapeutic opportunities" Chin J Traumatol. Jun. 2018; 21(3): 137-151. doi: 10.1016/j.cjtee.2018.02.003.
Yamaguchi, "RANK/RANKL/OPG during orthodontic tooth movement", Orthod Craniofac Res. May 2009; 12(2):113-9. doi: 10.1111/j.1601-6343.2009.01444.x.

(56) References Cited

OTHER PUBLICATIONS

Yamakazi et al., "Hair cycle-dependent expression of hepatocyte growth factor (HGF) activator, other proteinases, and proteinase inhibitors correlates with the expression of HGF in rat hair follicles", J Investig Dermatol Symp Proc., 4(3):312-5 (Dec. 1999).
Yang "Effect RANKL Produced by Periodontal Ligament Cells on Orthodontic Tooth Movement" (2016) Dental Theses. Paper 13.
Yang et al., "Acupuncture for hypertension," Cochrane Database of Systematic Reviews, Available Online at <https://www.cochranelibrary.com/cdsr/doi/10.1002/14651858.CD008821.pub2/full >, (2018), 4 pages.
Yang Lei, "Mechanisms and Reversal of Elastin Specific Medial Arterial Calcification" (2014). All Dissertations, Paper 1307, (available at https://tigerprints.clemson.edu/all_dissertations/1307), 214 pages.
Yarbrough et al., "Specific Binding and Mineralization of Calcified Surfaces by Small Peptides," Calcified Tissue International, vol. 86, (2010), pp. 58-66.
Yu et al. "Association between inflammation and systolic blood pressure in RA compared to patients without RA" Arthritis Research & Therapy vol. 20, Article No. 107 (2018).
Zalavras, Charalampos G. "CORR Insights(Registered): Cathodic Voltage-Controlled Electrical Stimulation Plus Prolonged Vancomycin Reduce Bacterial Burden of a Titanium Implant-associated Infection in a Rodent Model," Clinical Orthopaedics and Related Research, vol. 474, (2016), pp. 1676-1678.
Zaniboni et al. "Do electrical current and laser therapies improve bone remodeling during an orthodontic treatment with corticotomy?" Clin Oral Invest 23, 4083-4097 (2019). https://doi.org/10.1007/s00784-019-02845-9.
Zdzisinska et al. "RANK/RANKL i OPG w szpiczaku plazmocytowym [The role of RANK/RANKL and OPG in multiple myeloma]" Postepy Hig Med Dosw (Online). 2006; 60:471-482 (Abstract Only).
Zhang et al. "Exosomes derived from human embryonic mesenchymal stem cells promote osteochondral regeneration", Osteoarthritis and Cartilage, vol. 24, Issue 12, Dec. 2016, pp. 2135-2140.
Zhang et al., "Comparison of arterial stiffness in non-hypertensive and hypertensive population of various age groups," Jan. 24, 2018, 2 pages (Abstract Only).
Zhang et al., "Highly Stable and Reusable Imprinted Artificial Antibody Used for in Situ Detection and Disinfection of Pathogens," Chemical Science, vol. 6, (2015), pp. 2822-2826.
Zhao et al. "Local osteoprotegerin gene transfer inhibits relapse of orthodontic tooth movement." Am J Orthod Dentofacial Orthop. Jan. 2012; 141(1):30-40. doi: 10.1016/j.ajodo.2011.06.035.
Zupan et al. "The relationship between osteoclastogenic and anti-osteoclastogenic pro-inflammatory cytokines differs in human osteoporotic and osteoarthritic bone tissues," Journal of Biomedical Science, 2012, 19:28 (DOI: 10.1186/1423-0127-19-28).
Abdel-Rehim "Change of serum klotho protein and its relationship with endothelial dysfunction, oxidative stress and arterial aging in essential hypertensive patients" J Kidney 2018, vol. 4 (Dec. 2018).
Ahrens et al. "Klotho expression is a prerequisite for proper muscle stem cell function and regeneration of skeletal muscle" Ahrens et al. Skeletal Muscle (Jul. 2018) 8:20 pp. 1-14.
Akbari el al. "Association of Klotho gene polymorphism with hypertension and coronary artery disease in an Iranian population" BMC Cardiovascular Disorders (Dec. 2018) 18:237.
Asps, "Stem Cell Treatments 'Go Deep' to RegenerateSun-Damaged Skin" Article, American Society of Plastic Surgeons (May 27, 2020) 4 pages.
Banerjee et al. "MicroRNAs in Skin and Wound Healing" Methods Mol Biol. 2013; 936: 343-356, Author manuscript (Mar. 2015 ).
Barnhill "It's Electric! All About Microcurrent Facials" accessed Aug. 4, 2021, https://intothegloss.com/2016/04/microcurrent-treatment/.
Basu et al. "Exosomes for repair, regeneration and rejuvenation" Expert Opinion on Biological Therapy, 16:4, 489-506, DOI: 10.1517/14712598.2016.1131976.
Beugels et al. "Electrical stimulation promotes the angiogenic potential of adipose-derived stem cells" Scientific Reports (Aug. 2019) 9:12076.
Botchkareva "MicroRNA/mRNA regulatory networks in the control of skin development and regeneration" Cell Cycle 11:3, 468-474; (Feb. 2012) Landes Bioscience.
Carboni ei al. "An initial study on the effect of functional electrical stimulation in erectile dysfunction: a randomized controlled trial" IJIR: Your Sexual Medicine Journal (May 2018) 30:97-101.
Chaikin et al. "Microcurrent stimulation in the treatment of dry and wet macular degeneration" Clinical Ophthalmology 2015:9 2345-2353 (Dec. 2015).
Chen et al. "Beyond anti-VEGF: dual-targeting antiangiogenic and antiproliferative therapy" Am J Transl Res. 2013;5(4):393-403 Published May 24, 2013.
Chen et al. "Nanosecond Pulsed Electric Field (nsPEF) Ablation as an Alternative or Adjunct to Surgery for Treatment of Cancer" Chen et al., Surgery Curr Res 2013, S12 DOI: 10.4172/2161-1076.S12-005.
Choi et al. "Exosomes from human adipose-derived stem cells promote proliferation and migration of skin fibroblasts" Experimental Dermatology. (Sep. 2017) 1-3.
Costa et al. "Selecting patients for cytotoxic therapies in gastroenteropancreatic neuroendocrine tumours" Best Pract Res Clin Gastroenterol. Dec. 2012;26(6):843-54. doi: 10.1016/j.bpg.2012.12.001. PMID: 23582923.
Costa et al. "Treatment of advanced hepatocellular carcinoma with very low levels of amplitude-modulated electromagnetic fields" Br J Cancer. Aug. 23, 2011;105(5):640-8. doi: 10.1038/bjc.2011.292. Epub Aug. 9, 2011. PMID: 21829195; PMCID: PMC3188936.
Desai et al. "Use of Platelet-Rich Fibrin over Skin Wounds: Modified Secondary Intention Healing" Modified secondary intention healing. J Cutan Aesthet Surg (Jan.-Mar. 2013) vol. 6, pp. 35-37.
Dimensija "PRF Injections ForPRF Forskin Rejuvenationskin Rejuvenationand Tissueand TissueRegenerationRegeneration" accessed Aug. 4, 2021, https://dimensija.lv/news/prf-injekcijas-adas-atjaunosanai-un-audu-regeneracijai?lang=en.
Duscher et al. "Stem Cells in Wound Healing: The Future of Regenerative Medicine? A Mini-Review" (May 2015) Stem Cells in Wound Healing, Gerontology 2016;62:216-225.
Fallon "The obvious next step in the evolution of natural rejuvenation" Article (Aug. 2017) (accessed Aug. 4, 2021) https://www.newbeauty.com/platelet-rich-fibrin-skin-rejuvenation-prf/.
FDA "Same Surgical Procedure Exception under 21 CFR 1271.15(b): Questions and Answers Regarding the Scope of the Exception-Guidance for Industry" U.S. Department of Health and Human Services, Food and Drug Administration, Center for Biologics Evaluation and Research, Nov. 2017.
Fujiya et al. "Microcurrent Electrical Neuromuscular Stimulation Facilitates Regeneration of Injured Skeletal Muscle in Mice" Journal of Sports Science and Medicine (Jun. 2015) 14, 297-303.
Ge et al. "The aging skin microenvironment dictates stem cell behavior" PNAS (Mar. 2020), vol. 117, No. 10, pp. 5339-5350.
Goldberg et al. "Skin Rejuvenation with Non-Invasive Pulsed Electric Fields" Sci Rep 5, 10187 (May 2015).
HealthCMI, "Acupuncture Controls Hypertension In Groundbreaking Trial," Available online at <https://www.healthcmi.com/Acupuncture-Continuing-Education-News/1804-acupuncture-c . . . >, (2017), 9 pages.
Horsburgh et al "MicroRNAs in the skin; role in development, homeostasis, and regeneration" Clin Sci (Lond) (Jul.-Aug. 2017) 131 (15): 1923-1940.
Hunckler et al. "A current affair: electrotherapy in wound healing" Journal of Multidisciplinary Healthcare (Apr. 2017)10 179-194.
Itatani et al. "Resistance to Anti-Angiogenic Therapy in Cancer-Alterations to Anti-VEGF Pathway" Int J Mol Sci. Apr. 18, 2018;19(4):1232. doi: 10.3390/ijms19041232. PMID: 29670046; PMCID: PMC5979390.
Ivanyi "How Microcurrent Treatments Improve Acne" Envision Acne & Skin Care Center, website accessed Aug. 4, 2021, https://envisionacnecenter.com/microcurrent-treatments-improve-acne/.
Jamal et al. "Klotho, Hypertension and Arterial Stiffness: A Review" Austin J Nephrol Hypertens.(Jul. 2019) 6(2): 1082.

(56) References Cited

OTHER PUBLICATIONS

JCCR "Emerging roles of klotho in cardiovascular diseases%5D" Accessed Jun. 2, 2021 https://medcraveonline.com/JCCR/emerging-roles-of-klotho-in-cardiovascular-diseases.html%5D.
John et al. "Growth Factors in Skin Care—Series Introduction" (Mar. 2015) website accessed Aug. 4, 2021 http://barefacedtruth.com/2015/03/28/growth-factors-skin-care-introduction/.
John et al. "Growth Factors in Skin Care—Series Introduction" BareFacedTruth (Mar. 2015) 9 pages.
Kawagishi et al. S"onic hedgehog signaling regulates the mammalian cardiac regenerative response" Journal of Molecular and Cellular Cardiology; vol. 123, p. 180-184 (Oct. 2018).
Kim et al. "Picking Winners and Losers: Cell Competition in Tissue Development and Homeostasis" vol. 36, Issue 7, p. 490-498, Jul. 1, 2020 (Abstract Only).
Lam et al. "Mesenchymal stem cell therapies for skin repair and regeneration" J Dermat Cosmetol. (Aug. 2017) vol. 1, Issue 3, pp. 62?64.
Ledzewicz et al. "Analysis of optimal controls for a mathematical model of tumor anti-angiogenesis" Optim. Control Appl. Meth. 2006; 00:1-16.
Leonhardt "PressureStim Blood Pressure Control" accessed Jun. 2, 2021, https://pressurestim.com.
Leonhardt "PressureStim Receives IRB Approval to Launch Bioelectric Hypertension Treatment Clinical Study" Accessed Jun. 2, 2021, https://www.prdistribution.com/news/pressurestim-receives-irb-approval-to-launch-bioelectric-hypertension-treatment-clinical-study-2.html?fbclid=lwAR28Dh97RAKXXHrfgUONKW1pk-MWyeF_ibUlpQc_2XEN32C6sS%E2%80%A6.
LifeWave X39™ Patches; website access Aug. 4, 2021 https://lifewave.com/corporphan/store/product/39000.022.009/.
Loizzi et al. "Biological Pathways Involved in Tumor Angiogenesis and Bevacizumab Based Anti-Angiogenic Therapy with Special References to Ovarian Cancer" International Journal of Molecular Sciences. (Sep. 2017); 18(9):1967. https://doi.org/10.3390/ijms18091967.
Lopes-Bastos et al. "Tumour-Endothelial Cell Communications: Important and Indispensable Mediators of Tumour Angiogenesis" Anticancer Research Mar. 2016, 36 (3) 1119-1126.
Maltese et al. "The Putative Role of the Antiageing Protein Klotho in Cardiovascular and Renal Disease" Hindawi Publishing Corporation International Journal of Hypertension, (Sep. 2011) vol. 2012, Article ID 757469, 5 pages.
Mao et al. "13-Hydrogel fibrous scaffolds for accelerated wound healing" In Woodhead Publishing Series in Biomaterials, Electrofluidodynamic Technologies (EFDTs) for Biomaterials and Medical Devices, Woodhead Publishing, (Jan. 2018) pp. 251-274, ISBN 9780081017456, https://doi.org/10.1016/B978-0-08-101745-6.00013-X.
McMillan "Longevity Protein' Enables Muscle Regeneration In Old Mice" accesses Jun. 2, 2021; https://www.forbes.com/sites/fionamcmillan/2018/11/25/longevity-protein-enables-muscle-regeneration-in-old-mice/?sh=51709d57392a.
Metro News "Bioelectricity: A shocking revolution in skincare?" Website accessed Aug. 4, 2021 https://metro.co.uk/2010/09/26/bioelectricity-a-shocking-revolution-in-skincare-523763/.
Miron "The Concept of Smart Tissue Regeneration with PRF" (Apr. 3, 2017) accessed Aug. 4, 2021 http://oasisdiscussions.ca/2017/04/03/prf/.
Muratori et al. "The cytotoxic synergy of nanosecond electric pulses and low temperature leads to apoptosis" Sci Rep 6, 36835 (2016). https://doi.org/10.1038/srep36835.
Nacopoulos "Use of Platelet Rich Fibrin in Facial Aesthetics and Rejuvenation" (Jun. 2017) accessed Aug. 4, 2021 https://doi.org/10.1002/9781119406792.ch13.
Nature "Skin regeneration with insights" Nature 551, 141 (Nov. 2017) https://doi.org/10.1038/551141a.
Odell et al. "Anti-inflammatory Effects of Electronic Signal Treatment" Pain physician. 11. 891-907 (2008). 10.36076/ppj.2008/11/891.
Ojeh et al. "Stem Cells in Skin Regeneration, Wound Healing, and Their Clinical Applications" Int. J. Mol. Sci. (Oct. 2015), 16, ISSN 1422-0067 www.mdpi.com/journal/ijms.
Payne et al. "Bioelectric Control of Metastasis in Solid Tumors" Bioelectricityvol. 1, No. 3, (Sep. 16, 2019) https://doi.org/10.1089/bioe_2019.0013.
Petrescu et al. "Platelet rich fibrin as a gingival tissue regeneration enhancer" Journal of Dental Sciences, https://doi.org/10.1016/j.jds.2020.08.014.
Rocha et al. "Ultrasensitive System for Electrophysiology of Cancer Cell Populations: A Review" Bioelectricityvol. 1, No. 3 (Published Online:Sep. 16, 2019) https://doi.org/10.1089/bioe.2019.0020.
Ronchetti et al. "Dermal alterations in patients with Wilson's disease treated with D-penicillamine" J Submicrosc Cytol Pathol (Jan. 1989) 21(1 ):131-9.
Santos et al. "Interferential electrical stimulation improves peripheral vasodilatation in healthy individuals" Braz J Phys Ther. May-Jun. 2013; 17(3):281-288.
Sartori et al. "Effects of Transcutaneous Electrical Nerve Stimulation in Autonomic Nervous System of Hypertensive Patients: A Randomized Controlled Trial" Current Hypertension Reviews, Apr. 2018, 14, 66-71.
Segura et al. "New Material Developed for Accelerated Skin Regeneration in Major Wounds" National Institute of Biomedical Imaging and Bioengineering (Dec. 2015) Accessed Aug. 4, 2021 https://www.newswise.com/articles/new-material-developed-for-accelerated-skin-regeneration-in-major-wounds?channel=.
Silva et al. "Engineered hydrogel-based matrices for skin wound healing" (Dec. 2016) In book: Wound Healing Biomaterials (pp. 227-250) DOI:10.1016/B978-1-78242-456-7.00011-8.
Singh et al. "3D Printing of Scaffold for Cells Delivery: Advances in Skin Tissue Engineering" Polymers (Jan. 2016), 8, 19; doi:10.3390/polym8010019.
Skardal "Amniotic Fluid Stem Cells for Wound Healing" Perinatal Stem Cells (Jul. 2014) Springer, New York, NY. https://doi.org/10.1007/978-1-4939-1118-9_2.
Skardal et al. "Bioprinted Amniotic Fluid-Derived Stem Cells Accelerate Healing of Large Skin Wounds" Stem Cells TranslationalMedicine (Oct. 2012)1:792-802.
Su et al. "Klotho protein lowered in elderly hypertension" Int J Clin Exp Med (Aug. 2014) 7(8):2347-2350.
Sun "Regulation of Blood Pressure by Klotho" University of Oklahoma Health Sciences Center, Oklahoma City, OK, United States; accessed Jun. 2, 2021; https://grantome.com/grant/NIH/R01-HL102074-01A1.
Sun et al. "Amniotic fluid stem cells provide considerable advantages in epidermal regeneration: B7H4 creates a moderate inflammation microenvironment to promote wound repair" Scientific Reports (Jun. 2015) 5:11560, DOI: 10.1038/srep11560.
Takenaka et al. "Klotho Supplementation AttenuatesBlood Pressure and Cyst Growth InMouse Polycystic Kidney Disease" Journal of Hypertension: vol. 36—Issue—p. e76 (Jun. 2018).
Tyler "Nature's Electric Potential: A Systematic Review of the Role of Bioelectricity in Wound Healing and Regenerative Processes in Animals, Humans, and Plants" Front. Physiol., (Sep. 2017) https://doi.org/10.3389/fphys.2017.00627.
Vig et al. "Advances in Skin Regeneration Using Tissue Engineering" Int. J. Mol. Sci. (Apr. 2017), 18, 789; doi: 10.3390/ijms18040789.
Wei et al. "Nanofat-derived stem cells with platelet-rich fibrin improve facial contour remodeling and skin rejuvenation after autologous structural fat transplantation" Research Paper, Oncotarget (Jul. 2017) vol. 8, (No. 40), pp. 68542-68556.
Wu et al. "MSC-exosome: A novel cell-free therapy for cutaneous regeneration" Cytotherapy, vol. 20, Issue 3, (Mar. 2018) pp. 291-301, https://www.sciencedirect.com/science/article/pii/S146532491730717X.
Yang et al. "Effect of Amniotic Fluid Stem Cells and Amniotic Fluid Cells on the Wound Healing Process in a White Rat Model" APS, vol. 40, No. 5 (Sep. 2013).
Yildirimer et al. "Skin regeneration scaffolds: a multimodal bottom-up approach" Trends in Biotechnology, Dec. 2012, vol. 30, No. 12, pp. 638-648.

(56) References Cited

OTHER PUBLICATIONS

Yoon et al. "Skin Regeneration Effect and Chemical Composition of Essential Oil from Artemisia montana" Natural Product Communications (Sep. 2014) vol. 9, No. 11, pp. 1619-1622.
Yu et al. "Effects and mechanisms of a microcurrent dressing on skin wound healing: a review" Military Medical Research (Nov. 2014) 1:24 http://www.mmrjournal.org/content/1/1/24.
Yuan et al. "Electrical stimulation enhances cell migration and integrative repair in the meniscus" Sci Rep 4, 3674 (2014). https://doi.org/10.1038/srep03674.
Zaske "Discovery enables adult skin to regenerate like a newborn's" Medical Research, accessed Aug. 4, 2021 https://medicalxpress-com.cdn.ampproject.org/c/s/medicalxpress.com/news/2020-09-discovery-enables-adult-skin-regenerate.amp.
Zhang et al. "Therapeutic potential of stem cells in skin repair and regeneration" Chinese Journal of Traumatology (Apr. 2008) 11(4):209-221.
Zhong et al. "TKI-31 inhibits angiogenesis by combined suppression signaling pathway of VEGFR2 and PDGFRbeta" Cancer Biology & Therapy 5:3, 323-330, Mar. 2006.
Zhou et al. "Klotho Ameliorates Kidney Injury and Fibrosis and Normalizes Blood Pressure by Targeting the Renin-Angiotensin System" The American Journal of Pathology, vol. 185, No. 12, Dec. 2015.
Zhou et al. "Klotho Gene Deficiency Causes Salt-Sensitive Hypertension via Monocyte Chemotactic Protein-1/CC Chemokine Receptor 2-Mediated inflammation" J Am Soc Nephrol 26: 121-132, 2015 (Accepted Apr. 2014).
Zimmerman et al. "Cancer cell proliferation is inhibited by specific modulation frequencies" Br J Cancer. Jan. 17, 2012;106(2):307-13. doi: 10.1038/bjc.2011.523. Epub Dec. 1, 2011. PMID: 22134506; PMCID: PMC3261663.
Zimmerman et al. "Targeted treatment of cancer with radiofrequency electromagnetic fields amplitude-modulated at tumor-specific frequencies" Chin J Cancer. Nov. 2013;32(11):573-81. doi: 10.5732/cjc.013.10177. PMID: 24206915; PMCID: PMC3845545.
Dahm et al. "Decalcification of the aortic valve does not prevent early recalcification" J Heart Valve Dis., 9(1):21-6 (Jan. 2000).
Ghazalian et al. "Effects of whole-body vibration training on fibrinolytic and coagulative factors in healthy young men." Journal of Research in Medical Sciences: the official journal of Isfahan University of Medical Sciences vol. 19,10 (Oct. 2014): 982-986.
Messas et al. "Feasibility and Performance of Noninvasive Ultrasound Therapy in Patients With Severe Symptomatic Aortic Valve Stenosis: A First-in-Human Study. Circulation" Mar. 2, 2021;143(9):968-970. doi: 10.1161/CIRCULATIONAHA.120.050672. Epub Jan. 25, 2021.
Petrusca et al. "Experimental investigation of thermal effects in HIFU-based external valvuloplasty with a non-spherical transducer, using high-resolution MR thermometry" Phys Med Biol. Sep. 7, 2009;54(17):5123-38. doi: 10.1088/0031-9155/54/17/004. Epub Aug. 6, 2009 (ABSTRACT).
Tsang et al. "Large animal models of cardiovascular disease" Cell Biochemistry and Function (Feb. 2016) vol. 34, Issue 3 p. 113-132.
Villemain et al. Pulsed Cavitational Ultrasound Softening : A New Noninvasive Therapeutic Approach for Calcified Bioprosthetic Valve Stenosis JACC: Basic to Translational Science vol. 2, Issue 4, Aug. 2017, pp. 372-383.
Westermark et al. "Effect of externally applied focused acoustic energy on clot disruption in vitro" Clinical Science 97(1):67-71 (Jul. 1999); DOI:10.1042/CS19980379.
Wu et al. "Validation study toward measuring the mechanical properties of blood clots using resonant acoustic spectroscopy with optical vibrometry." Proceedings of SPIE—the International Society for Optical Engineering vol. 8214 (epub Feb. 2012): 82140G. doi:10.1117/12.906956.
Lanzetto et al. "Fundamental principles of an anti-VEGF treatment regimen: optimal application of intravitreal anti-vascular endothelial growth factor therapy of macular diseases," Graefes Arch. Clin. Exp. Ophthalmol. 2017; 255(7): 1259-1273 (published online May 19, 2017); doi: 10.1007/s00417-017-3647-4.
Lasserre et al., "Influence of Low Direct Electric Currents and Chlorhexidine Upon Human Dental Biofilms," Clinical and Experimental Dental Research, vol. 2, (Jul. 2016), pp. 146-154.
Lasserre et al., "Oral Microbes, Biofilms and Their Role in Periodontal and Peri-Implant Diseases," Materials, vol. 11, (Sep. 2018), Article 1802, 17 pages.
Lee et al. "Hepatocyte growth factor (HGF) activator expressed in hair follicles is involved in in vitro HGF-dependent hair follicle elongation," J. Dermatol. Sci., 25(2): 156-63 (Feb. 2001).
Lee et al., "Targeted Release of Tobramycin From a pH-Responsive Grafted Bilayer Challenged With *S. aureus*," Biomacromolecules, vol. 16, (2015), pp. 650-659.
Lei et al., "Efficacy of Reversal of Aortic Calcification by Chelating Agents," Calcified Tissue International, vol. 93, (Nov. 2013), 15 pages.
Leibrock et al., "NH4CI Treatment Prevents Tissue Calcification in Klotho Deficiency," Journal of the American Society of Nephrology, vol. 26, (2015), pp. 2423-2433.
Leonhardt "Micro Stimulator" http://www.bioleonhardt.com/micro-stimulator/.
Leonhardt "Leonhardt Adds HIF-1 Alpha To Estate of Bioelectric Controlled Release Regenerative Proteins" Press Release, Published Jun. 13, 2017.
Leonhardt, "Leonhardt Ventures Files Patent for Heart Valve Regeneration," (available at https://bioleonhardt.com/leonhardt-ventures-files-patent-for-heart-valve-regeneration/), (Mar. 20, 2018), 6 pages.
Leonhardt, H.—Leonhardt Announces Vibrational Energy Device For Preventing Blood Clots Provisional Patent Application and License Agreements, (available at https://leonhardtventures.com/leonhardt-announces-vibrational-energy-device-preventing-blood-clots-provisional-patent-application-license-agreements/), (Jul. 5, 2017), 5 pages.
Leonhardt, Leonhardt Announces Vibrational Energy Device For Preventing Blood Clots Provisional Patent Application and License Agreements, (available at https://leonhardtventures.com/leonhardt-announces-vibrational-energy-device-preventing-blood-clots-provisional-)atent-application-license-agreements/), (Jul. 5, 2017), 5 pages.
Leonhardt's Launchpads Announces Filing of Patent for Bioelectric Stimulation Controlled Klotho Expression—Powerful Anti-aging and Regeneration Promoting Protein, by API Podder, Published: Mar. 13, 2019, available online at <https://mysocialgoodnews.com/leonhardts-launchpads-announces-filing-of-patent-for-bioelectric-stimulation-controlled-klotho-expression-powerful-anti-aging-and-regeneration-promoting-protein/.
Li "Regulation of Renal Oxygenation and Blood Pressure" Art. Virginia Commonwealth University, Richmond, VA, United States (Abstract).
Li et al., "Exogenous IGF-1 promotes hair growth by stimulating cell proliferation and down regulating TGF-(Beta)1 in C57BL/6 mice in vivo" Growth Hormone & IGF Research, vol. 24, Issues 2-3, pp. 89-94 (Apr.-Jun. 2014).
Li et al., "Long-Lasting Reduction of Blood Pressure by Electroacupuncture in Patients with Hypertension: Randomized Controlled Trial," Medical Acupuncture, vol. 27, No. 4, (2015), pp. 253-266.
Li et al., "Repetitive Electroacupuncture Attenuates Cold-Induced Hypertension through Enkephalin in the Rostral Ventral Lateral Medulla," Scientific Reports, vol. 6, (2016), 10 pages.
Li et al., "The Mechanism of Acupuncture in Treating Essential Hypertension: A Narrative Review," International Journal of Hypertension, vol. 2019, (2019), Article ID 8676490, 10 pages.
Li, et al. "Local injection of RANKL facilitates tooth movement and alveolar bone remodelling." Oral Diseases, 25(2), 550-560. https://doi.org/10.1111/odi.13013.
Liang et al. "Therapeutic effect of low-intensity pulsed ultrasound on temporomandibular joint injury induced by chronic sleep deprivation in rats" Am J Transl Res. 2019; 11(6): 3328-3340.
Liesz et al. "Editorial: Mechanisms of neuroinflammation and inflammatory neurodegeneration in acute brain injury" Front. Cell. Neurosci., 2015. doi://doi.org/10.3389/fncel.2015.00300.

(56) References Cited

OTHER PUBLICATIONS

Lobo-Silva et al. "Balancing the immune response in the brain: IL-10 and its regulation," Journal of Neuroinflammation, 13:297 (2016); doi.org/10.1186/s12974-016-0763-8.
Longhurst et al. "Evidence-based blood pressure reducing actions of electroacupuncture: mechanisms and clinical application" Sheng Li Xue Bao. Oct. 25, 2017; 69(5): 587-597.
Lop et al., Cutting-Edge Regenerative Medicine Technologies for the Treatment of Heart Valve Calcification, Calcific Aortic Valve Disease, (2013), (available at http://dx.doi.org/10.5772/55327), 57 pages.
Malakhov et al. "Assessment of Efficacy of Non-Invasive Peripheral Transcutaneous Electrical Nerve Stimulation for Correction of Blood Pressure in Patients With Arterial Hypertension" Journal of Hypertension: Jul. 2019—vol. 37—Issue—p. e88-e89 doi: 10.1097/01.hjh.0000570296.70620.44.
Mann, "Innate Immunity and the Failing Heart: The Cytokine Hypothesis Revisited," Circ. Res. Mar. 27, 2015; 116(7): 1254-1268.
Martin "Historically significant events in the discovery of RANK/RANKL/OPG" World J Orthop. Oct. 18, 2013; 4(4): 186-197. doi: 10.5312/wjo.v4.i4.186.
Mass Device "Greatbatch wins FDA PMA for Algovita SCS" http://www.massdevice.com/greatbatch-wins-fda-pma-for-algovita-scs/ (Dec. 1, 2015).
Matsumori, "Cytokines and Heart Failure: Pathophysiological Roles and Therapeutic Implications," Heart Failure, Springer, Tokyo; doi.org/10.1007/978-4-431-68331-5_3.
Mcbride et al. "Aortic valve decalcification" J Thorac Cardiovasc Surg. Jul. 1990;100(1):36-42; discussion 42-3 (Abstract Only).
McGrath "OPG/RANKL/RANK Pathway as a Therapeutic Target in Cancer" Journal of Thoracic Oncology, Sep. 2011 6(9): 1468-1473.
Mclean et al., "Training the Biofilm Generation—a Tribute to J. W. Costerton," Journal of Bacteriology, vol. 194, (Dec. 2012), pp. 6706-6711.
Meadows et al. "Anti-VEGF Therapies in the Clinic," Cold Spring Harb. Perspect. Med. Oct. 2012; 2(10): a006577: doi: 10.1101/cshperspect.a006577.
Medtronic "Cardiac Resynchronization Therapy (CRT) Devices For Heart Failure" http://www.medtronic.com/us-en/patients/treatments-therapies/crt-devices.html.
Miles et al. "Assessment of the changes in arch perimeter and irregularity in the mandibular arch during initial alignment with the AcceleDent Aura appliance vs no appliance in adolescents: A single-blind randomized clinical trial", Dec. 2016, vol. 150, Issue 6 American Journal of Orthodontics and Dentofacial Orthopedics (9 pages).
Mishra "Angiogenic neovessels promote tissue hypoxia," Proc. Natl. Acad. Sci. U. S. A. Sep. 20, 2016; 113(38): 10458-10460, published online Sep. 13, 2016; doi: 10.1073/pnas. 1612427113.
Moe, "Klotho: A Master Regulator of Cardiovascular Disease?," Circulation, vol. 125, (2012), pp. 2181-2183.
Mosteiro et al. "Tissue damage and senescence provide critical signals for cellular reprogramming in vivo." Science, 2016; 354 (6315): aaf4445 DOI: 10.1126/science.aaf4445.
Niiranen et al., "Relative Contributions of Arterial Stiffness and Hypertension to Cardiovascular Disease: The Framingham Heart Study," Journal of the American Heart Association, vol. 5, No. 11, 2016, 8 pages.
Nimeri et al. "Acceleration of tooth movement during orthodontic treatment—a frontier in Orthodontics", Prog Orthod 2013; 14:42; DOI: 10.1186/2196-1042-14-42.
Nodzo et al., "Cathodic Electrical Stimulation Combined With Vancomycin Enhances Treatment of Methicillin-Resistant *Staphylococcus aureus* Implant-Associated Infections," Clinical Orthopaedics and Related Research, vol. 473, (2015), pp. 2856-2864.
Nodzo et al., "Cathodic Voltage-Controlled Electrical Stimulation Plus Prolonged Vancomycin Reduce Bacterial Burden of a Titanium Implant-associated Infection in a Rodent Model," Clinical Orthopaedics and Related Research, vol. 474, (2016), 1668-1675.
Nordstorm "Electrical Stimulation Blood Pressure Treatment Devices Market to Set Astonishing Growth by 2026" Art. Apr. 4, 2019 Gator Ledger.
Norton et al. "Bioelectric Perturbations of Bone: Research Directions and Clinical Applications" Angle Orthod (1984) 54 (1): 73-87.
Novack "Inflammatory osteoclasts, a different breed of bone eaters?" Arthritis Rheumatol. Dec. 2016; 68(12): 2834-2836. doi: 10.1002/art.39835.
Novickij et al., "Induction of Different Sensitization Patterns of MRSA to Antibiotics Using Electroporation," Molecules, vol. 23,(2018), Article 1799, 10 pages.
O'Neill et al., "Recent Progress in the Treatment of Vascular Calcification," Kidney International, vol. 78, (Dec. 2010), pp. 1232-1239.
Oranger et al. "Cellular Mechanisms of Multiple Myeloma Bone Disease" Clinical and Developmental Immunology vol. 2013, Article ID 289458, 11 pages http://dx.doi.org/10.1155/2013/289458.
Otero et al. "Expression and Presence of OPG and RANKL mRNA and Protein in Human Periodontal Ligament with Orthodontic Force", Gene-Regulation-and-Systems-Biology, 2016, 10, 15-20.
Our Approach to Improve Hair Loss by Increasing Hair Growth Factor IGF-1, http://www.jhgc.com.sg/theory/igf-1/index.html.
Apuzzo et al. "Biomarkers of Periodontal Tissue Remodeling during Orthodontic Tooth Movement in Mice and Men: Overview and Clinical Relevance", The Scientific World Journal, vol. 2013 (2013), Article ID 105873, 8 pages, http://dx.doi.org/10.1155/2013/105873.
"Electric Tumor Treatment Fields," No. 0827 Policy, aetna.com/cpb/medical/data/800_899/0827.html (Nov. 18, 2016), last visited Sep. 12, 2018.
"Electrical brain stimulation could support stroke recovery," sciencedaily.com/releases/2016/03/160316151108.htm (Mar. 16, 2016), last visited Sep. 12, 2018.
Alghatrif et al. "The Conundrum of Arterial Stiffness, Elevated blood pressure, and Aging" Curr Hypertens Rep. Feb. 2015; 17(2): 12. doi: 10.1007/s11906-014-0523-z.
Almpani et al., "Nonsurgical Methods for the Acceleration of the Orthodontic Tooth Movement", Tooth Movement. Front Oral Biol., vol. 18, pp. 80-91 (Karger, Basel, CH 2016) (DOI:10.1159/000382048), Published online: Nov. 24, 2015.
Andersson et al. "Drinking, antidiuresis and milk ejection from electrical stimulation within the hypothalamus of the goat," Acta Physiol Scand. Dec. 31, 1955; 35(2):191-201; DOI: 10.1111/j.1748-1716.1955.tb01277.x.
Ando et al." RANKL/RANK/OPG: key therapeutic target in bone oncology" Curr Drug Discov Technol. Sep. 2008; 5(3): 263-268.
Apuzzo et al. "Biomarkers of Periodontal Tissue Remodeling during Orthodontic Tooth Movement in Mice and Men: Overview and Clinical Relevance", The Scientific World Journal, vol. 2013 (2013), Article ID 105873, 8 pages, http://dx.doi.0rg/10.1155/2013/105873.
Aronowitz et al. "Mechanical versus enzymatic isolation of stromal vascular fraction cells from adipose tissue" SpringerPlus (2015) 4:713 DOI 10.1186/s40064-015-1509-2.
Atkinson et al. "Bioelectric Properties of the Tooth" 1969 vol. 48 issue: 5, pp. 789-794.
Aubert et al. "A new ultrasonic process for a renewal of aortic valve decalcification" Cardiovascular Ultrasound 2006, 4:2 doi:10.1186/1476-7120-4-2.
Aydin et al., "Focusing of Electromagnetic Waves by a Left-Handed Metamaterial Flat Lens," vol. 13, (2005), pp. 8753-8759.
Back et al. "Endogenous Calcification Inhibitors in the Prevention of Vascular Calcification: A Consensus Statement From the COST Action EuroSoftCalcNet" Frontiers in Cardiovascular Medicine | www.frontiersin.org, Jan. 2019 | vol. 5 | Article 196.
Banerjee, P. "Electrical muscle stimulation for chronic heart failure: an alternative tool for exercise training?" Curr Heart Fail Rep., 7(2):52-8. doi: 10.1007/s11897-010-0013-9 (Jun. 2010).
Bang et al., "Attenuation of Hypertension by C-Fiber Stimulation of the Human Median Nerve and the Concept-Based Novel Device," Scientific Reports, vol. 8, (2018), 12 pages.
Barbault et al., Amplitude-modulated electromagnetic fields for the treatment of cancer: Discovery of tumor-specific frequencies and

(56) References Cited

OTHER PUBLICATIONS assessment of a novel therapeutic approach, Journal of Experimental & Clinical Cancer Research, Apr. 14, 2009, vol. 28, No. 51, doi:10.1186/1756-9966-28-51, 10 pages.
Barker et al., "A Formidable Foe is Sabotaging Your Results: What You Should Know About Biofilms and Wound Healing," Plastic and Reconstructive Surgery, vol. 139, (2017), pp. 1184e-1194e.
Beebe et al. "Bioelectric Applications for Treatment of Melanoma," Cancers (Basel). Sep. 2010; 2(3): 1731-1770, published online Sep. 27, 2010; doi: 10.3390/cancers20317.
Beitelshees et al. "CXCL5 polymorphisms are associated with variable blood pressure in cardiovascular disease-free adults" Hum Genomics. 2012; 6(1): 9.
Berman "Suzanne Somers' Experimental Breast Reconstruction" Medpage Today, Feb. 7, 2012, www.medpagetoday.com > blogs > celebritydiagnosis.
Bi et al. "Key Triggers of Osteoclast-Related Diseases and Available Strategies for Targeted Therapies: A Review" Front Med (Lausanne). 2017; 4: 234. doi: 0.3389/fmed.2017.00234.
Blood Vessels Hold Key To Thicker Hair Growth, https://www.sciencedaily.com/releases/2001/02/010215074636.htm(Feb. 2001).
Blum "Role of cytokines in heart failure," American Heart Journal, vol. 135, Issue 2, Feb. 1998, pp. 181-186; doi.org/10.1016/S0002-8703(98)70080-8.
Borden et al., "Electric Current-Induced Detachment of *Staphylococcus epidermidis* Biofilms from Surgical Stainless Steel," Applied and Environmental Microbiology, vol. 70, (2004), pp. 6871-6874.
Borgobello, B. "FDA approves the treatment of brain tumors with electrical fields," New Atlas, http://newatlas.com/treatment-of-brain-tumors-with-electrical-fields/21433/(Feb. 13, 2012), last visited Sep. 12, 2018.
Boyle "Wound-Treating Jelly Regenerates Fresh, Scar-Free Skin", Popular Science, (Dec. 15, 2011), "New material developed for accelerated skin regeneration in major wounds", Science Highlight, (National Institute of Biomedical 11 Imaging and Bioengineering, Dec. 17, 2015).
Bradshaw et al. "Designer self-assembling hydrogel scaffolds can impact skin cell proliferation and migration" Nature Scientific Reports, vol. 4, Article No. 6903 (2014).
Brooks et al. "Bioelectric impedance predicts total body water, blood pressure, and heart rate during hemodialysis in children and adolescents" J. Ren Nutr., 18(3):304-311 (May 2008); doi: 10.1053/j.jm.2007.11.008.
Buckle et al. "Soluble Rank Ligand Produced by Myeloma Cells Causes Generalised Bone Loss in Multiple Myeloma" PLoS One. 2012; 7(8): e41127. doi: 10.1371/journal.pone.0041127 PMCID: PMC3430669.
Cai et al., "Intermedin Inhibits Vascular Calcification by Increasing the Level of Matrix (Gamma)—Carboxyglutamic Acid Protein," Cardiovascular Research, vol. 85, (2010), pp. 864-873.
CalXStars Business Accelerator, Inc.—Website—Justia Patents—Mar. 15, 2017—US Patent Application for Stimulator, Pump & Composition Patent Application (Application #20170266371) https://protect-us.mimecast.com/s/tSaBCxkVlwuDr61CvMWbF?domain=patents.justia.com.
Campbell et ali. "Electrical stimulation to optimize cardioprotective exosomes from cardiac stem cells" Med Hypotheses. Mar. 2016; 88:6-9. doi: 10.1016/j.mehy.2015.12.022. Epub Jan. 11, 2016.
Canty et al., "Antibiotics Enhance Prevention and Eradication Efficacy of Cathodic-Voltage-Controlled Electrical Stimulation against Titanium-Associated Methicillin-Resistant *Staphylococcus aureus* and Pseudomonas aeruginosa Biofilms," mSphere, vol. 4, (May/Jun. 2019), e00178-19, 14 pages.
Caubet et al., "A Radio Frequency Electric Current Enhances Antibiotic Efficacy Against Bacterial Biofilms," Antimicrobial Agents and Chemotherapy, vol. 48, (2004), vol. 4662-4664.
Cerrada et al. "Hypoxia-Inducible Factor 1 Alpha Contributes to Cardiac Healing in Mesenchymal Stem Cells-Mediated Cardiac Repair," Stem Cells and Development, 22(3): 501-511 (2013).
Cervera "The interplay between genetic and bioelectrical signaling permits a spatial regionalisation of membrane potentials in model multicellular ensembles," Nature, Scientific Reports, Oct. 12, 2016 vol. 6, Article No. 35201 (2016).
Chang et al. "Pulsed electromagnetic fields stimulation affects osteoclast formation by modulation of osteoprotegerin, RANK ligand and macrophage colony-stimulating factor", Journal of Orthopaedic Research, 23 (2005) 1308-1314.
Chang et al. Effect of Pulse-Burst Electromagnetic Field Stimulation on Osteoblast Cell Activities; Bioelectromagnetics 25:457-465 (2004).
Chemet & Levin, "Transmembrane voltage potential is an essential cellular parameter for the detection and control of tumor development in a Xenopus model," Dis. Models & Mech. 6, pp. 595-607 (2013); doi:10.1242/dmm.010835.
Chen et al. "Secreted Klotho Attenuates Inflammation-Associated Aortic Valve Fibrosis in Senescence-Accelerated Mice P1" Hypertension. 2018;71:877-885. DOI: 10.1161/HYPERTENSIONAHA.117.10560.) Downloaded from http://ahajournals.org by on Apr. 24, 2020 (9 pages).
Chen et al., "Deficiency in the Anti-Aging Gene Klotho Promotes Aortic Valve Fibrosis Through AMPK(Alpha)-Mediated Activation of RUNX2," Aging Cell, vol. 15, (Oct. 2016), pp. 853-860.
Chen et al., "Regenerative Hair Waves in Aging Mice and Extra-Follicular Modulators Follistatin, Dkk1, and Sfrp4," Journal of Investigative Dermatology, Aug. 2014, vol. 134, Issue 8, pp. 2086-2096.
Chen et al., "The Role and Mechanism of (Alpha)-Klotho in the Calcification of Rat Aortic Vascular Smooth Muscle Cells," BioMed Research International, vol. 2015, (2015), 7 pages.
Chen et al., "The Strategy to Prevent and Regress the Vascular Calcification in Dialysis Patients," BioMed Research International, vol. 2017, (2017), 11 pages.
Chen et al., Efficacy and Safety of Acupuncture for Essential Hypertension: A Meta-Analysis, Medical Science Monitor, vol. 24, (2018), pp. 2946-2969.
Chiang et al., "Silver-Palladium Surfaces Inhibit Biofilm Formation," Applied and Environmental Microbiology, vol. 75, (2009), pp. 1674-1678.
Christouls et al. "Pathogenesis and Management of Myeloma Bone Disease" Expert Rev Hematol. 2009; 2(4):385-398.
Ciria et al., Antitumor effectiveness of different amounts of electrical charge in Ehrlich and fibrosarcoma Sa-37 tumors, BMC Cancer, Nov. 26, 2004, 10 pages, vol. 4, No. 87.
Collette et al., "Measurement of the local aortic stiffness by a non-invasive bioelectrical impedance technique," in Medical & Biological Engineering, vol. 49, No. 4, Feb. 2011, pp. 431-439, Available online at <https://www.ncbi.nlm.nih.gov/pubmed/21286830>, 1 page (Abstract Only).
Collins "Bioelectric Signals Can Be Used to Detect Early Cancer," Tufts News, http://now.tufts.edu/news-releases/bioelectric-signals-used-detect-early-cancer (Feb. 1, 2013).
Oyajobi "Multiple myeloma/hypercalcemia" Arthritis Research & Therapy vol. 9, Article No. S4 (2007).
Palza et al., "Electroactive Smart Polymers for Biomedical Applications," Materials, vol. 12, (2019), 24 pages.
Park et al. "Effects of SM-215 on Hair Growth by Hair Follicle Stimulation", Indian Journal of Science and Technology, vol. 8(25), DOI: 10.17485/ijst/2015/v8i25/80263, (Oct. 2015).
Park, Alice "Shrinking Stem Cells Are the Real Reason for Hair Loss" Time, (Feb. 5, 2016).
Paulus "Cytokines and heart failure," Heart Fail. Monit. 2000; 1(2):50-6.
Pierce et al. "Collection and characterization of amniotic fluid from scheduled C-section deliveries," Cell Tissue Bank, DOI 10.1007/s10561-016-9572-7 (Springer, 2012) and is available from Irvine Scientific.
Plumbing Today, "How to Remove Hard, White Mineral Deposits from Faucets/Showerheads," (available at https://plumbingtoday.biz/blog/how-to-remove-hard-white-mineral-deposits-from-faucets-showerheads), (Jul. 11, 2016), 4 pages.

(56) References Cited

OTHER PUBLICATIONS

Pozo et al., "Bioelectric Effect and Bacterial Biofilms. A Systematic Review," The International Journal of Artificial Organs, vol. 31, (2008), pp. 786-795.
Pozo et al., "Effect of Electrical Current on the Activities of Antimicrobial Agents Against Pseudomonas Aeruginosa, *Staphylococcus aureus*, and *Staphylococcus epidermidis* Biofilms," Antimicrobial Agents and Chemotherapy, vol. 53, (2009), pp. 35-40.
Pozo et al., "Prevention of *Staphylococcus epidermidis* Biofilm Formation Using Electrical Current," Journal of Applied Biomaterials & Functional Materials, vol. 12, (2014), pp. 81-83.
Pozo et al., "The Electricidal Effect: Reduction of *Staphylococcus* and Pseudomonas Biofilms by Prolonged Exposure to Low-Intensity Electrical Current," Antimicrobial Agents and Chemotherapy, vol. 53, (2009), pp. 41-45.
Price et al. "Mitral Valve Repair is Feasible Following Extensive Decalcification and Reconstruction of the Atrioventricular Groove" J Heart Valve Dis. Jan. 2015;24(1):46-52 (Abstract Only).
Prochazka et al. "Therapeutic Potential of Adipose-Derived Therapeutic Factor Concentrate for Treating Critical Limb Ischemia," Cell Transplantation, 25(9), pp. 1623-1633(11) (2016).
Prochazka et al., "Cocktail of Factors from Fat-derived Stem Cells Shows Promise for Critical Limb Ischemia" http://www.sciencenewsline.com/news/2016012204520017.html (Jan. 21, 2016).
Pupo et al., Electrotherapy on Cancer: Experiment and Mathematical Modeling, Current Cancer Treatment—Novel Beyond Conventional Approaches, Prof. Oner Ozdemir (Ed.) ISBN: 978-953-307-397-2, InTech, Available from: http://www.intechopen.com/books/current-cancer-treatment-novel-beyond-conventional-approaches/electrotherapy-on-cancer-experiment-and-mathematical-modeling, 2011.
Puro et al "Bioelectric impact of pathological angiogenesis on vascular function," PNAS Aug. 30, 2016 113 (35) 9934-9939; published ahead of print Aug. 22, 2016 https://doi.org/10.1073/pnas.1604757113.
Rachner et al. "Prognostic Value of RANKL/OPG Serum Levels and Disseminated Tumor Cells in Nonmetastatic Breast Cancer" Clin Cancer Res Feb. 15, 2019 (25) (4) 1369-1378; DOI: 10.1158/1078-0432.CCR-18-2482.
Raje et al. "Role of the RANK/RANKL Pathway in Multiple Myeloma" Clin Cancer Res 2019 25(1):12-20; DOI: 10.1158/1078-0432.CCR-18-1537.
Ren et al., "Efficient Eradication of Mature Pseudomonas Aeruginosa Biofilm via Controlled Delivery of Nitric Oxide Combined with Antimicrobial Peptide and Antibiotics," Frontiers in Microbiology, vol. 7, Article 1260, (Aug. 2016), 8 pages.
Reversing Age-Related Hair Loss and Restoring Healthy Hair Growth in Men and Women https://nutritionreview.org/2015/08/reversing-age-related-hair-loss-and-restoring-healthy-hair-growth-in-men-and-women/ (Aug. 24, 2015).
RFA (radiofrequency ablation), Swedish Medical Imaging, 2 pages, author unknown, undated.
Roy et al., "Disposable Patterned Electroceutical Dressing (PED-10) Is Safe for Treatment of Open Clinical Chronic Wounds," Advances in Wound Care, vol. 8, (1019), pp. 149-159.
Sabbah "Electrical vagus nerve stimulation for the treatment of chronic heart failure", Cleve Clin J Med, 78 Suppl 1: S24-9. doi: 10.3949/ccjm.78.s1.04 (Aug. 2011).
Sabino-Carvalho et al., "Non-invasive Vagus Nerve Stimulation Acutely Improves Blood Pressure Control in a Placebo Controlled Study," The FASEB Journal, vol. 31, 2017, available online at <https://www.fasebj.org/doi/abs/10.1096/fasebj.31.1_supplement.848.8 >, 2 pages) Abstract Only.
Sahmeddini et al., "Electro-Acupuncture Stimulation at Acupoints Reduced the Severity of Hypotension During Anesthesia in Patients Undergoing Liver Transplantation," Journal of Acupuncture and Meridian Studies, vol. 5, Issue 1, (2012), pp. 11-14.
Sahoo and Losardo, "Exosomes and Cardiac Repair After Myocardial Infarction", Circulation Research, 114:333-344 (Jan. 16, 2014).
Salcedo et al., "Low current electrical stimulation upregulates cytokine expression in the anal sphincter," Int. J. Colorectal Dis., Feb. 2012;27(2):221-5. doi: 10.1007/s00384-011-1324-3. Epub (Oct. 2011).
Sandvik et al., "Direct Electric Current Treatment under Physiologic Saline Conditions Kills *Staphylococcus epidermidis* Biofilms via Electrolytic Generation of Hypochlorous Acid," PloS one, vol. 8, (Feb. 2013), e55118, 14 pages.
Schardong et al., "Intradialytic neuromuscular electrical stimulation reduces DNA damage in chronic kidney failure patients: a randomized controlled trial," Biomarkers, vol. 23, Issue 5, 2018, pp. 1-11.
Schimmel et al. "Neuroinflammation in traumatic brain injury: A chronic response to an acute injury" Brain Circ, 2017, 3(3):135-142.
Schmidt-Malan et al., "Activity of Fixed Direct Electrical Current in Experimental *Staphylococcus aureus* Foreign-Body Osteomyelitis," Diagnostic Microbiology and Infectious Disease, vol. 93, (2019), pp. 92-95.
Seifi & Jeszri "Correlation of bone resorption induced by orthodontic tooth movement and expression of RANKL in rats", Dental Journal, vol. 26, No. 4 (2009).
Sethi et al. "Aortic stiffness: pathophysiology, clinical implications, and approach to treatment" Integr Blood Press Control. 2014; 7: 29-34.
Shahid et al., "Rhinosinusitis in Children," ISRN Otolaryngology, vol. 2012, Article ID 851831, (Dec. 2012), 11 pages.
Shirtliff et al., "Assessment of the Ability of the Bioelectric Effect to Eliminate Mixed-Species Biofilms," Applied and Environmental Microbiology, vol. 71, (2005), pp. 6379-6382.
Shoji-Matsunaga et al. "Osteocyte regulation of orthodontic force-mediated tooth movement via RANKL expression." Scientific Reports, 7: 8753, published online Aug. 18, 2017, DOI:10.1038/s41598-017-09326-7.
Showkatbakhsh et al. "Effect of Intra-Canal Direct Current Electric Stimulation on Orthodontic Tooth Movement: An Experimental Study in Canines" Journal of Dental School 2016; 34(3): 157-67.
Showkatbakhsh et al. "The effect of pulsed electromagnetic fields on the acceleration of tooth movement." World J Orthod. 2010 Winter;11(4):e52-6.
Signature Orthodontics "Accelerated Tooth Movement", http://www.sigortho.com/accelerated-tooth-movement, visited Mar. 15, 2017.
Silvers et al. "The Bioelectric Code: Reprogramming Cancer and Aging from the Interface of Mechanical and Chemical Microenvironments," Front. Cell Dev. Biol., Mar. 6, 2018; doi.org/10.3389/fcell.2018.00021.
Sisay et al. "The RANK/RANKL/OPG system in tumorigenesis and metastasis of cancer stem cell: potential targets for anticancer therapy" Onco Targets Ther. 2017; 10: 3801-3810.
Somayaji et al., "In Vitro Scanning Electron Microscopic Study on the Effect of Doxycycline and Vancomycin on Enterococcal Induced Biofilm," Iranian Endodontic Journal, vol. 5, (2010), pp. 53-58.
Souli et al., "Effects of Slime Produced by Clinical Isolates of Coagulase-Negative Staphylococci on Activities of Various Antimicrobial Agents," Antimicrobial Agents and Chemotherapy, vol. 42, (Apr. 1998), pp. 939-941.
Spadari et al., Electrical stimulation enhances tissue reorganization during orthodontic tooth movement in rats; Clinica Oral Investigations, Jan. 2017, vol. 21, Issue 1, pp. 111-120, Abstract.
Spiridonov et al. "Effect of Transcutaneous Electrical Stimulation of Nerves on Blood Pressure and Blood Content of Neuropeptide CGRP and Nitric Oxide in Hypertensive Rats with Metabolic Disturbances" Bull Exp Biol Med (Feb. 2019) 166: 436-437.
Stein et al., "The effect of transcutaneous electrical nerve stimulation on blood pressure," Blood Pressure, vol. 22, Issue 3, 2013, available online at <https://www.tandfonline.com/doi/full/10.3109/08037051.2012.722271 >, 5 pages.
Stenn et al., "Bioengineering the Hair Follicle," Organogenesis, 3(1): 6-13 (Jan.-Mar. 2007).
Stewart et al., "Electrolytic Generation of Oxygen Partially Explains Electrical Enhancement of Tobramycin Efficacy Against Pseudomonas Aeruginosa Biofilm," Antimicrobial Agents and Chemotherapy, vol. 43, (1999), pp. 292-296.

(56) References Cited

OTHER PUBLICATIONS

Stoodley et al., "Influence of Electric Fields and pH on Biofilm Structure as Related to the Bioelectric Effect," Antimicrobial Agents and Chemotherapy, vol. 41, (1997), pp. 1876-1879.
Sultana et al., "Electrochemical Biofilm Control: A Review," Biofouling, vol. 31, (2015), pp. 745-758.
Columbia "Implant Procedure Concepts—Pacemaker, ICD and CRT Overview," columbia.edu/itc/hs/medical/hickey/docs/Pacemaker,%20ICD%20and%20CRT%20Overview%20022007.pdf, last risited Sep. 12, 2018.
Control of Hair Growth by a Growth Factor Protein, http://www.hairloss-reversible.com/control-of-hair-growth-by-a-growth-factor-protein/.
Control of pelage hair follicle development and cycling by complex interactions between follistatin and activin, FASEB J (Jan. 2, 2003).
Corrigan et al. "Neurogenic inflammation after traumatic brain injury and its potentiation of classical inflammation", Journal of Neuroinflammation, 2016, 13:264; doi://doi.org/10.1186/s12974-016-0738-9.
Costerton et al., "Mechanism of Electrical Enhancement of Efficacy of Antibiotics in Killing Biofilm Bacteria," Antimicrobial Agents and Chemotherapy, vol. 38, (1994), pp. 2803-2809.
Costerton et al., "The Application of Biofilm Science to the Study and Control of Chronic Bacterial Infections," The Journal of Clinical Investigation, vol. 112, (2003), pp. 1466-1477.
Cowburn et al. "HIF isoforms in the skin differentially regulate systemic arterial pressure" Proc Natl Acad Sci U S A. Oct. 22, 2013; 110(43): 17570-17575.
Cross et al. "Milk Ejection following Electrical Stimulation of the Pituitary Stalk in Rabbits," Nature 166, 994-995 (Dec. 9, 1950); doi:10.1038/166994b0 (Abstract Only).
Dai et al. "Nanosecond Pulsed Electric Fields Enhance the Anti-tumour Effects of the mTOR Inhibitor Everolimus against Melanoma," Scientific Reports vol. 7, Article No. 39597 (2017).
Delcaru et al., "Microbial Biofilms in Urinary Tract Infections and Prostatitis: Etiology, Pathogenicity, and Combating strategies," Pathogens, vol. 5, (2016), 12 pages.
Deswal et al. "Cytokines and Cytokine Receptors in Advanced Heart Failure An Analysis of the Cytokine Database from the Vesnarinone Trial (VEST)," Circulation. 2001;103:2055-2059; ://doi.org/10.1161/01.CIR.103.16.2055.
Dibart et al. "Tissue response during Piezocision-assisted tooth movement: a histological study in rats", Eur J Orthod (2014) 36 (4): 45764; DOI: https://doi.org/10.1093/ejo/cjt079.
Dietrich et al. "Decalcification of the mitral annulus: surgical experience in 81 patients" Thorac Cardiovasc Surg. Oct. 2006;54(7):464-7 (Abstract Only).
Dong-Hwan Kim et al., The effects of electrical current from a micro-electrical device on tooth movement, Korean Orthod., Oct. 2008, 38(5):337-346.
Ehrlich et al., "Engineering Approaches for the Detection and Control of Orthopaedic Biofilm Infections," Clinical Orthopaedics and Related Research, vol. 437, (2005), pp. 59-66.
El-Bialy et al. "Effect of Low Intensity Pulsed Ultrasound (LIPUS) on Tooth Movement and Root Resorption: A Prospective Multi-Center Randomized Controlled Trial" J. Clin. Med. 2020, 9, 804; doi:10.3390/jcm9030804.
Elastatropin(Registered) in Scalp & Hair Conditioning https://www.proteingenomics.com/haircare.html.
Electric Tumor Treatment Fields, No. 0827 Policy, http://www.aetna.com/cpb/medical/data/800_899/0827.html (Nov. 18, 2016).
Electrical brain stimulation could support stroke recovery https://www.sciencedaily.com/releases/2016/03/160316151108.htm (Mar. 16, 2016).
Ellis, Marie "Cure for baldness? Stem cells bring hope" http://www.medicalnewstoday.com/articles/271898.php.
Eurekalert, UCI Study Finds Acupuncture Lowers Hypertension by Activating Natural Opioids, Available Online at < https://www.eurekalert.org/pub_releases/2016-10/uoc-usf103116.php >, (2016), 2 pages.
Fan et al., "A Review on the Nonpharmacological Therapy of Traditional Chinese Medicine with Antihypertensive Effects," Evidence-Based Complementary and Alternative Medicine, vol. 2019, (2019), Article ID 1317842, 7 pages.
Fatemi et al. "Imaging elastic properties of biological tissues by low-frequency harmonic vibration" Proceedings of the IEEE, 91(10):1503-1519 (Oct. 2003).
FDA Approves Algovita Spinal Cord Stimulation System from Greatbatch, http://www.odtmag.com/contents/view_breaking-news/2015-12-02/fda-approves-algovita-spinal-cord-stimulation-system-from-greatbatch (Dec. 2, 2015).
Ferris, "Battle against baldness turns to stem cells" http://www.cnbc.com/2015/01/29/studies-indicate-its-possible-to-use-stem-cells-to-cure-baldness.html (Jan. 29, 2015).
Ferrucci, D. A. "Introduction to This is Watson'," in IBM Journal of Research and Development, vol. 56, No. 3.4, pp. 1:1-1:15, May-Jun. 2012. DOI: 10.1147/JRD.2012.2184356.
Fili et al. "Therapeutic implications of osteoprotegerin" Cancer Cell International vol. 9, Article No. 26 (2009).
Flachskampf et al., "Randomized Trial of Acupuncture to Lower Blood Pressure," Circulation, vol. 115, (2007), pp. 3121-3129.
Fonseca et al. "Electrical stimulation: Complementary therapy to improve the performance of grafts in bone defects?" Journal of Biomedical Materials Research Part B: Applied Biomaterials 2018 vol. 000b, Issue 0.
Froughreyhani et al., "Effect of Electric Currents on Antibacterial Effect of Chlorhexidine Against Entrococcus Faecalis Biofilm: An in Vitro Study," Journal of Clinical and Experimental Dentistry, vol. 10, (Dec. 2018), pp. e1223-e1229.
Fukuoka et al. "Hair Regeneration Treatment Using Adipose-Derived Stem Cell Conditioned Medium: Follow-up With Trichograms" Eplasty, 15:e10 (Mar. 2015).
Fukuoka et al., "The Latest Advance in Hair Regeneration Therapy Using Proteins Secreted by Adipose-Derived Stem Cells" The American Journal of Cosmetic Surgery, 29(4):273-282 (2012).
Gavira et al. "Repeated implantation of skeletal myoblast in a swine model of chronic myocardial infarction," Eur. Heart J., 31(8): 1013-1021. doi: 10.1093/eurheartj/ehp342 (2010).
Giganti et al. "Changes in serum levels of TNF-alpha, IL-6, OPG, RANKL and their correlation with radiographic and clinical assessment in fragility fractures and high energy fractures", J Biol Regul Homeost Agents, Oct.-Dec. 2012; 26(4):671-80.
Giladi et al., "Microbial Growth Inhibition by Alternating Electric Fields," Antimicrobial Agents and Chemotherapy, vol. 52, (2008), pp. 3517-3522.
Golberg et al., "Eradication of Multidrug-Resistant A. Baumannii in Burn Wounds by Antiseptic Pulsed Electric Field," Technology, vol. 2, (2014), pp. 153-160.
Golberg et al., "Pulsed Electric Fields For Burn Wound Disinfection in a Murine Model," Journal of Burn Care & Research, vol. 36, (2015), pp. 7-13.
Goranov et al. "Bone Lesions in Multiple Myeloma—The OPG/RANK-ligand System" Folia Med (Plovdiv). 2004; 46(3): 5-11 (Abstract Only).
Goswami et al. "Osteoprotegerin rich tumor microenvironment: implications in breast cancer" Oncotarget. Jul. 5, 2016; 7(27): 42777-42791.
Grad, D., "Electrical Scalp Device Can Slow Progression of Deadly Brain Tumors", New York Times, https://www.nytimes.com/2014/11/16/health/electrical-scalp-device-can-slow-progression-of-deadly-brain-tumors.html?_r=0 (Nov. 15, 2014).
Greenwald "Pulse pressure and arterial elasticity" QJM: An International Journal of Medicine, vol. 95, Issue 2, 2002, pp. 107-112.
Guimarães-Camboa et al. "Redox Paradox: Can Hypoxia Heal Ischemic Hearts?" Cell, 39(4):392-394, (Nov. 21, 2016) DOI: http://dx.doi.org/10.1016/j.devcel.2016.11.007.
Gullestad et al. "Inflammatory cytokines in heart failure: mediators and markers," Cardiology. 2012;122(1):23-35. doi: 10.1159/000338166. Epub Jun. 12, 2012.
Gurbax et al. "Accelerated Orthodontic Tooth Movement: A Review" mod Res Dent. 1(2). MRD.000508. 2017. DOI: 10.31031/MRD.2017.01.000508.

(56) References Cited

OTHER PUBLICATIONS

Hair Growth Factors, Nanogen, http://www.svijet-kose.com/dokumenti/Serum-vegf.pdf.
Hamman, R. "Modulation Of RANKL and Osteoprotegerin in Adolescents Using Orthodontic Forces", Masters Thesis, University of Tennessee (2010).
Hamzelou et al. "Cancer reversed in frogs by hacking cells' electricity with light," New Scientist This Week, Mar. 16, 2016.
Hari et al., "Application of Bioelectric Effect to Reduce the Antibiotic Resistance of Subgingival Plaque Biofilm: An in Vitro Study," Journal of Indian Society of Periodontology, vol. 22, (2018), pp. 133-139.
Harkins et al., "Chitosan-Cellulose Composite for Wound Dressing Material. Part 2. Antimicrobial Activity, Blood Absorption Ability, and Biocompatibility," Journal of Biomedical Materials Research Part B, Applied biomaterials, vol. 102, (2014), 1199-1206.
Hart, K. "RANKL and Osteoprotegerin Levels in Response to Orthodontic Forces" (2012). Theses and Dissertations (ETD). Paper 107. http://dx.doi.org/10.21007/etd.cghs.2012.0127.
Alves et al. "A mesenchymal stromal cell gene signature for donor age" PLoS One. 2012;7(8):e42908. doi: 10.1371/journal.pone.0042908. Epub Aug. 23, 2012. PMID: 22927939; PMCID: PMC3426516.
Andringa et al. "Role of Hypoxia-Inducible Factors in Acute Kidney Injury" Nephron Clin Pract (Sep. 2014) 127: 70-74; doi.org/10.1159/000363669.
Apel et al. (2010), Effect of locally delivered IGF-1 on nerve regeneration during aging: an experimental study in rats, Muscle & nerve, 41(3), 335-341. doi.org/10.1002/mus.21485.
Apuzzo et al. "Biomarkers of Periodontal Tissue Remodeling during Orthodontic Tooth Movement in Mice and Men: Overview and Clinical Relevance", The Scientific World Journal, vol. 2013 (2013), Article ID 105873, 8 pages, http://dx.doi.org/10.1155/2013/1058.
Bourdillon et al. "Electromagnetic Brain Stimulation in Patients With Disorders of Consciousness" Front. Neurosci., (Mar. 18, 2019): doi org/10.3389/fnins.2019.00223.
Bowser et al. "Effects of the activin A-myostatin-follistatin system on aging bone and muscle progenitor cells" Exp Gerontol. Feb. 2013;48(2):290-7. doi: 10.1016/j.exger.2012.11.004. Epub Nov. 21, 2012. PMID: 23178301; PMCID: PMC3678732.
Bre et al. "Prevention of bioprosthetic heart valve calcification: strategies and outcomes". Curr Med Chem. 2014;21(22):2553-64. doi: 10.2174/09298673216661312121512l6. PMID: 24358975.
Bruggemann et al. "Effects of Neuromuscular Electrical Stimulation During Hemodialysis on Peripheral Muscle Strength and Exercise Capacity: A Randomized Clinical Trial." Arch Phys Med Rehabil. May 2017;98(5):822-831.e1. doi: 10.1016/j.apmr.2016.12.009. Epub Jan. 16, 2017. (Abstract Only).
Caradu et al. "Endogenous Sonic Hedgehog limits inflammation and angiogenesis in the ischaemic skeletal muscle of mice". Cardiovasc Res. Apr. 1, 2018;114(5):759-770. doi: 10.1093/cvr/cvy017. PMID: 29365079.
Chen et al. "The Strategy to Prevent and Regress the Vascular Calcification in Dialysis Patients", BioMed Research International, vol. 2017, Article ID 9035193, 11 pages, 2017; doi.org/10.1155/2017/9035193.
Chen et al. "Deficiency in the anti-aging gene Klotho promotes aortic valve fibrosis through AMPKa-mediated activation of RUNX2." Aging Cell vol. 15, 5 (2016): 853-60. doi:10.1111/acel.12494.
Chen et al. "The Role and Mechanism of a-Klotho in the Calcification of Rat Aortic Vascular Smooth Muscle Cells." BioMed Research International vol. 2015 (2015): 194362. doi:10.1155/2015/194362.
Cheng et al. "The Role of SDF-1/CXCR4/CXCR7 in Neuronal Regeneration after Cerebral Ischemia." Frontiers in Neuroscience vol. 11 590. Oct. 24, 2017, doi:10.3389/fnins.2017.00590.
Chera et al. "Diabetes recovery by age-dependent conversion of pancreatic d-cells into insulin producers." Nature, 2014; DOI: 10.1038/nature13633.
Chernet "Transmembrane voltage potential is an essential cellular parameter for the detection and control of tumor development in a Xenopus model," Dis. Models & Mech. 6, pp. 595-607 (2013); doi:10.1242/dmm.010835.
Chu et al. "Mechanical stretch induces hair regeneration through the alternative activation of macrophages." Nature Communications, 10(1), 1524 (2019). doi.org/10.1038/s41467-019-09402-8.
Dalise et al., "Biological effects of dosing aerobic exercise and neuromuscular electrical stimulation in rats", Sci Rep. Sep. 7, 2017; 7(1):10830.
Dalton et al. "New Insights into the Mechanism of Action of Soluble Klotho." Frontiers in endocrinology vol. 8 323. Nov. 17, 2017, doi:10.3389/fendo.2017.00323.
Deng et al. "Effects of SDF-1/CXCR4 on the Repair of Traumatic Brain Injury in Rats by Mediating Bone Marrow Derived Mesenchymal Stem Cells" Cell Mol Neurobiol. Mar. 2018; 38(2):467-477. doi: 10.1007/s10571-017-0490-4. Epub May 8, 2017. Erratum in: Cell Mol Neurobiol. Apr. 2021;41(3):617-618. PMID: 28484859.
Dërmaku-Sopjani et al. "Klotho-Dependent Role of 1,25(OH)2D3 in the Brain" Neurosignals. Mar. 31, 2021;29(1):14-23. doi: 10.33594/000000352. PMID: 33784444.
Dërmaku-Sopjani et al. "Significance of the anti-aging protein Klotho" Molecular Membrane Biology, 30:8, 369-385 (Aug. 2013), DOI: 10.3109/09687688.2013.837518.
Diaco et al. "Amniotic fluid-derived stem cells as an effective cell source for transplantation therapy in stroke." Brain Circ 2015;1:119-24.
Dilorio "High-frequency external muscle stimulation in acute kidney injury (AKI): potential shortening of its clinical course" Clinical Nephrology, vol. 78—No. Suppl. Jan. 2012 (S37-S45).
Dote-Montero et al. "Predictors of Sexual Desire and Sexual Function in Sedentary Middle-Aged Adults: The Role of Lean Mass Index and S-Klotho Plasma Levels. The Fit-Ageing Study." J Sex Med. Apr. 2020;17(4):665-677. doi: 10.1016/j.jsxm.2020.01.016. Epub Feb. 20, 2020. PMID: 32089483.
Drew et al. "Association between Soluble Klotho and Change in Kidney Function: The Health Aging and Body Composition Study" J Am Soc Nephrol Jun. 2017, 28(6):1859-1866; DOI: doi.org/10.1681/ASN.2016080828.
Ferrari "The Effect of Electrical Stimulation on Aged Skeletal Muscle Regenerative Potential" http://d-scholarship.pitt.edu/28094/1/FerrariRJ_ETD_May_31_2016_PDF.pdf.
Floege et al. "A New Look at Platelet-Derived Growth Factor in Renal Disease" J Am Soc Nephrol (Jan. 2008), 19(1):12-23; DOI: doi.org/10.1681/ASN.2007050532.
Fu et al. "Loss of Klotho in CKD Breaks One's Heart" J Am Soc Nephrol Oct. 2015, 26 (10) 2305-2307; DOI: https://doi.org/10.1681/ASN.2015020200.
Fukuoka et al. "Hair Regeneration Therapy: Application of Adipose-Derived Stem Cells." Current Stem Cell Research & Therapy vol. 12,7 (2017): 531-534. doi:10.2174/1574888X12666170522114307.
Garcia et al. "1,25(OH)2vitamin D3 stimulates myogenic differentiation by inhibiting cell proliferation and modulating the expression of promyogenic growth factors and myostatin in C2C12 skeletal muscle cells" Endocrinology. Aug. 2011;152(8):2976-86. doi: 10.1210/en.2011-0159. Epub Jun. 14, 2011. PMID: 21673099; PMCID: PMC3138228.
Geribaldi-Doldán et al. "Protein Kinase C: Targets to Regenerate Brain Injuries?" Front. Cell Dev. Biol., Mar. 20, 2019): doi.org/10.3389/fcell.2019.00039.
Ghuman et al. "Biodegradation of ECM hydrogel promotes endogenous brain tissue restoration in a rat model of stroke". Acta Biomater. Oct. 15, 2018;80:66-84. doi: 10.1016/j.actbio.2018.09.020. Epub Sep. 16, 2018. PMID: 30232030; PMCID: PMC6217851.
Golembiewska et al. "The Role of Klotho Protein in Chronic Kidney Disease: Studies in Animals and Humans" Current Protein & Peptide Science vol. 17, Issue 8, 2016; DOI: 10.2174/1389203717666160526123646.
Grange et al. "Urinary Extracellular Vesicles Carrying Klotho Improve the Recovery of Renal Function in an Acute Tubular Injury Mode" Molecular Therapy vol. 28 No. 2 490-502 (Feb. 2020) (with Supplemental Information) https://doi.org/10.1016/j.ymthe.2019.11.013.

(56) References Cited

OTHER PUBLICATIONS

Gutierrez et al. "a-Klotho and Kidney Function Decline: An Important Step Forward in Understanding the Link Between Mineral Metabolism and Kidney Disease Progression" Am J Kidney Dis. (Jun. 2013) 61(6):855-857.
Guyot et al. "Pancreatic nerve electrostimulation inhibits recent-onset autoimmune diabetes". Nat Biotechnol 37, 1446-1451 (2019): doi org/10.1038/s41587-019-0295-8.
Hasegawa et al. "Recent advances in renal regeneration." F1000Research vol. 8 F1000 Faculty Rev-216. Feb. 25, 2019, doi:10.12688/f1000research.17127.1.
Hoyer et al. "Electroconvulsive therapy enhances the anti-ageing hormone Klotho in the cerebrospinal fluid of geriatric patients with major depression." Eur Neuropsychopharmacol. Mar. 2018;28(3):428-435. doi: 10.1016/j.euroneuro.2017.12.012. Epub Dec. 20, 2017. PMID: 29274997.
Hu et al. "Recombinant a-Klotho may be prophylactic and therapeutic for acute to chronic kidney disease progression and uremic cardiomyopathy" Kidney International Basic Research vol. 91, Issue 5, p. 1104-1114 (Jan. 2017); DOI:https://doi.org/10.1016/j.kint.2016.10.034.
Hu et al. "Renal and extrarenal actions of Klotho." Seminars In Nephrology vol. 33,2 (2013): 118-29. doi:10.1016/j.semnephrol.2012.12.013.
Hu et al. "Secreted klotho and chronic kidney disease" Advances in Experimental Medicine and Biology, Jan. 1, 2012, 728:126-157; DOI: 10.1007/978-1-4614-0887-1_9.
International Search Report for International Application No. PCT/US2020/021556, dated Jun. 29, 2020, 3 pages.
International Written Opinion for International Application No. PCT/US2020/021556, dated Jun. 29, 2020, 4 pages.
Jayaraj et al. "Neuroinflammation: friend and foe for ischemic stroke". J Neuroinflammation 16, 142 (2019): doi.org/10.1186/s12974-019-1516-2.
Joo et al. "Various Wavelengths of Light-Emitting Diode Light Regulate the Proliferation of Human Dermal Papilla Cells and Hair Follicles via Wnt/β-Catenin and the Extracellular Signal-Regulated Kinase Pathways." Annals of Dermatology vol. 29,6 (2017): 747-754. doi:10.5021/ad.2017.29.6.747.
Jorge et al. "Klotho deficiency aggravates sepsis-related multiple organ dysfunction" Am J Physiol Renal Physiol 316: F438-F448, (Dec. 5, 2018); doi:10.1152/ajprenal.00625.2017.
Kim et al. "Hyaluronate—Epidermal Growth Factor Conjugate for Skin WoundHealing and Regeneration" Biomacromolecules (Oct. 2016) 17 , 11, 3694-3705 (Abstract Only) Publication Date : Oct. 24, 2016.
Kim et al. "Wnt/β-catenin and ERK pathway activation: A possible mechanism of photobiomodulation therapy with light-emitting diodes that regulate the proliferation of human outer root sheath cells." Lasers Surg Med. Dec. 2017;49(10):940-947. doi: 10.1002/lsm.22736. Epub Sep. 25, 2017. PMID: 28944964.
Klotho et al. "Klotho expression in osteocytes regulates bone metabolism and controls bone formation" Kidney International (2017) 92, 599-611.
Kuro-O "The Klotho proteins in health and disease" Nat Rev Nephrol 15, 27-44 (Nov. 19, 2018); doi.org/10.1038/s41581-018-0078-3.
Takenaka et al. "Klotho protein supplementation reduces blood pressure and renal hypertrophy in db/db mice, a model of type 2 diabetes" Acta Physiol (Oxf). Feb. 2019; 225(2):e13190. doi: 10.1111/apha.13190. Epub Oct. 16, 2018.
Tang-Schomer MD. "3D axon growth by exogenous electrical stimulus and soluble factors." Brain Res. Jan. 1, 2018;1678:288-296. doi: 10.1016/j.brainres.2017.10.032. Epub Oct. 31, 2017. PMID: 29097106.
The et al. "Mechanistic Roles of Matrilin-2 and Klotho in Modulating the Inflammatory Activity of Human Aortic Valve Cells" Cells 2020, 9, 385; doi:10.3390/cells9020385.
Thurston et al. "Tumor necrosis factor and interferon-gamma down-regulate Klotho in mice with colitis". Gastroenterology. Apr. 2010;138(4):1384-94, 1394.e1-2. doi: 10.1053/j.gastro.2009.12.002. Epub Dec. 11, 2009. PMID: 20004202; PMCID: PMC3454518.
Torbus-Paluszczak et al. "Klotho protein in neurodegenerative disorders," Neurol. Sci. 39, 1677-1682 (2018): doi.org/10.1007/s10072-018-3496-x.
Van Kampen et al. "Treatment of Erectile Dysfunction by Perineal Exercise, Electromyographic Biofeedback, and Electrical Stimulation," Phys. Ther. 2003; 83(6):536-543.
Vervloet et al. "Fibroblast growth factor-23 and Klotho in chronic kidney disease" Kidney International Supplements vol. 1, Issue 4, p. 130-135, Sep. 1, 2011;DOI: https://doi.org/10.1038/kisup.2011.29.
Wang et al. "Correlation between Soluble a-Klotho and Renal Function in Patients with Chronic Kidney Disease: A Review and Meta-Analysis", BioMed Research International, vol. 2018, Article ID 9481475, 12 pages, (Aug. 2018). https://doi.org/10.1155/2018/9481475.
Wang, et al. "Secreted klotho from exosomes alleviates inflammation and apoptosis in acute pancreatitis." American Journal Of Translational Research vol. 11,6 3375-3383. Jun. 15, 2019.
Witkowski et al. "Klotho-a Common Link in Physiological and Rheumatoid Arthritis-Related Aging of Human CD4+ Lymphocytes" J Immunol (2007), 178(2):771-777; DOI: doi.org/10.4049/jimmunol.178.2.771.
Xia et al. "Klotho Contributes to Pravastatin Effect on Suppressing IL-6 Production in Endothelial Cells." Mediators of Inflammation vol. 2016 (2016): 2193210. doi:10.1155/2016/2193210.
Xie et al. "Klotho Acts as a Tumor Suppressor in Cancers" Jul. 2013 Pathology & Oncology Research 19(4) DOI:10.1007/s12253-013-9663-8.
Xuan et al. "Changes in expression of klotho affect physiological processes, diseases, and cancer." Iranian journal of basic medical sciences vol. 21,1 (2018): 3-8.
Yaden et al. "Follistatin: a novel therapeutic for the improvement of muscle regeneration," Journal of Pharmacology and Experimental Therapeutics Mar. 13, 2014, jpet.113.211169; DOI: doi.org/10.1124/jpet.113.211169.
Yamauchi et al. "Wound healing delays in a-Klotho-deficient mice that have skin appearance similar to that in aged humans—Study of delayed wound healing mechanism" Biochemical and Biophysical Research Communications vol. 473, Issue 4, May 13, 2016, pp. 845-852.
Yarbrough et al. "Specific binding and mineralization of calcified surfaces by small peptides." Calcified Tissue International vol. 86,1 (2010): 58-66. doi:10.1007/s00223-009-9312-0.
Zhang et al. "Association of Klotho and interleukin 6 gene polymorphisms with aging in Han Chinese population." J Nutr Health Aging. Dec. 2014;18(10):900-4. doi: 10.1007/s12603-014-0470-z. PMID: 25470806.
Zhang et al. "Klotho Protein Protects Human Keratinocytes from UVB-Induced Damage Possibly by Reducing Expression and Nuclear Translocation of NF-?B." Medical Science Monitor : International Medical Journal of Experimental and Clinical Research vol. 24 8583-8591. Nov. 27, 2018, doi: 10.12659/MSM.910687.
Zhao et al. "Enhancing endogenous capacity to repair a stroke-damaged brain: An evolving field for stroke research" Progress in Neurobiology vols. 163-164, Apr.-May 2018, pp. 5-26.
Zhou et al. "Advance of Stem Cell Treatment for Traumatic Brain Injury" Front. Cell. Neurosci., (Aug. 13, 2019): doi.org/10.3389/fncel.2019.00301.
Zhou et al. "Sonic hedgehog signaling in kidney fibrosis: a master communicator" Science China. Life sciences vol. 59,9 (Sep. 2016): 920-9. doi:10.1007/s11427-016-0020-y.
Zhu et al. "Klotho controls the brain-immune system interface in the choroid plexus" E11388-E11396 PNAS, vol. 115, No. 48, www.pnas.org/cgi/doi/10.1073/pnas.1808609115 accessed Apr. 12, 2019.
Ziaaldini et al. "Exercise training increases anabolic and attenuates catabolic and apoptotic processes in aged skeletal muscle of male rats" Exp Gerontol. Jul. 2015; 67:9-14. doi: 10.1016/j.exger.2015.04.008. Epub Apr. 21, 2015. PMID: 25910622.
Zou et al. "The role of klotho in chronic kidney disease." BMC nephrology vol. 19,1 285. Oct. 22, 2018, doi:10.1186/s12882-018-1094-z.

(56) References Cited

OTHER PUBLICATIONS

Zununi et al. "Klotho and Renal Fibrosis," Nephro-Urol Mon. (Nov. 2013) 5(5):946-948. doi:10.5812/numonthly.16179.
Lang et al. "Therapeutic Interference with Vascular Calcification—Lessons From Klotho-Hypomorphic Mice and Beyond" Front. Endocrinol. (May 2018): doi.org/10.3389/fendo.2018.00207.
Lee et al. "Klotho ameliorates diabetic nephropathy via LKB1-AMPK-PGC1a-mediated renal mitochondrial protection" Biochemical and Biophysical Research Communications vol. 534, Jan. 1, 2021, pp. 1040-1046.
Lei "Mechanisms and Reversal Of Elastin Specific Medial Arterial Calcification." (2014). All Dissertations. 1307; tigerprints.clemson.edu/all_dissertations/1307/.
Leon et al. "Peripheral Elevation of a Klotho Fragment Enhances Brain Function and Resilience in Young, Aging, and a-Synuclein Transgenic Mice" Cell Reports vol. 20, Issue 6, Aug. 6, 2017, pp. 1360-1371.
Li et al. "GDF10 is a signal for axonal sprouting and functional recovery after stroke" Nat Neurosci 2015; Epub Oct. 15, 2015.
Li et al. "Hair Growth Promotion Activity and Its Mechanism of Polygonum multiflorum." Evid Based Complement Alternat Med. 2015;2015:517901. doi: 10.1155/2015/517901. Epub Jul. 30, 2015. PMID: 26294926; PMCID: PMC4534627.
Liebano et al. "Vascular Endothelial Growth Factor Release Following Electrical Stimulation in Human Subjects" Advances in Wound Care, vol. 3, No. 2, pp. 98-103 (Jun. 2013).
Lim et al. "a-Klotho Expression in Human Tissues." The Journal Of Clinical Endocrinology And Metabolism vol. 100,10 (2015): E1308-18. doi:10.1210/jc.2015-1800.
Lim et al. "Klotho: A Major Shareholder in Vascular Aging Enterprises" Int. J. Mol. Sci. 2019, 20(18), 4637; doi.org/10.3390/ijms20184637.
Liu et al. "Stem cell competition orchestrates skin homeostasis and ageing". Nature 568, 344-350 (2019); doi.org/10.1038/s41586-019-1085-7.
Lu et al. "Klotho/FGF23 Axis in Chronic Kidney Disease and Cardiovascular Disease" Kidney Dis (Jul. 2017) 3:15-23; doi.org/10.1159/000452880.
Malyshevskaya et al. "Role of Electrical Activity in Horizontal Axon Growth in the Developing Cortex: A Time-Lapse Study Using Optogenetic Stimulation" PLOS ONE (2013): doi.org/10.1371/journal.pone.0082954.
Martín-González et al. "Soluble a-Klotho in Liver Cirrhosis and Alcoholism, Alcohol and Alcoholism", vol. 54, Issue 3, May 2019, pp. 204-208.
Martín-Núñez et al. "Implications of Klotho in vascular health and disease" World J Cardiol. Dec. 26, 2014; 6(12):1262-1269.
Martinez-Redondo et al. "aKLOTHO and sTGFβR2 treatment counteract the osteoarthritic phenotype developed in a rat model". Protein Cell 11, 219-226 (2020): doi.org/10.1007/s13238-019-00685-7.
Mir et al. "IGF-1 mediated Neurogenesis Involves a Novel RIT1/Akt/Sox2 Cascade." Sci Rep 7, 3283 (2017): doi.org/10.1038/s41598-017-03641-9.
Missoum et al. "Recent Updates on Mesenchymal Stem Cell Based Therapy for Acute Renal Failure" Curr Urol 2019;13:189-199; DOI: 10.1159/000499272.
Mitani et al. "In Vivo klotho Gene Transfer Ameliorates Angiotensin II-Induced Renal Damage" Hypertension (Apr. 2002) 39:838-843; https://doi.org/10.1161/01.HYP.0000013734.33441.EA.
Morales-García et al. "The alkaloids of Banisteriopsis caapi, the plant source of the Amazonian hallucinogen Ayahuasca, stimulate adult neurogenesis in vitro". Sci Rep 7, 5309 (2017): doi.org/10.1038/s41598-017-05407-9.
Morimoto et al. "Electrical Stimulation Enhances Migratory Ability of Transplanted Bone Marrow Stromal Cells in a Rodent Ischemic Stroke Model" Cell Physiol Biochem (Dec. 2018) 46:57-68.
Mostafidi et al. "Serum Klotho Levels in Trained Athletes", Nephro-Urol Mon. (Jan. 2016); 8(1):e30245. doi:10.5812/numonthly.30245.
Nakamura et al. "Eicosapentaenoic acid prevents arterial calcification in klotho mutant mice." PLoS One. Aug. 3, 2017;12(8):e0181009. doi: 10.1371/journal.pone.0181009. PMID: 28771600; PMCID: PMC5542469.
Negaresh et al. "The effect of resistance training on quadriceps muscle volume and some growth factors in elderly and young men" Adv Gerontol. 2017;30(6):880-887. PMID: 29608833.
Nih et al. "Dual-function injectable angiogenic biomaterial for the repair of brain tissue following stroke". Nature Mater 17, 642-651 (2018): doi.org/10.1038/s41563-018-0083-8.
Noguchi et al. "Alteration of skin wound healing in keratinocyte-specific mediator complex subunit 1 null mice" PLoS One. Aug. 14, 2014;9(8):e102271. doi: 10.1371/journal.pone.0102271. PMID: 25122137; PMCID: PMC4133190.
Nowak et al. "Prognostic Value and Link to Atrial Fibrillation of Soluble Klotho and FGF23 in Hemodialysis Patients" PLoS One. Jul. 3, 2014;9(7):e100688. doi: 10.1371/journal.pone.0100688.
Pai et al. "Endogenous Gradients of Resting Potential Instructively Pattern Embryonic Neural Tissue via Notch Signaling and Regulation of Proliferation." Journal of Neuroscience, 2015; 35 (10): 4366 DOI: 10.1523/JNEUROSCI.1877-14.2015.
Papaioannou et al. "Sonic Hedgehog signaling limits atopic dermatitis via Gli2-driven immune regulation" J Clin Invest. 2019; 129(8):3153-3170; doi.org/10.1172/JCI125170.
Paroni et al. "Klotho Gene and Selective Serotonin Reuptake Inhibitors: Response to Treatment in Late-Life Major Depressive Disorder". Mol Neurobiol. Mar. 2017;54(2):1340-1351. doi: 10.1007/s12035-016-9711-y. Epub Feb. 3, 2016. PMID: 26843110.
Pastor et al. "Treating Systemic Klotho Deficiency" Am J Nephrol (Apr. 2019) 49:410-412; doi.org/10.1159/000499864.
Prather et al. "Longevity factor klotho and chronic psychological stress". Translational Psychiatry, 2015; 5 (6):e585 DOI: 10.1038/tp.2015.81.
Prud'homme et al. "The anti-aging protein Klotho is induced by GABA therapy and exerts protective and stimulatory effects on pancreatic beta cells." Biochem Biophys Res Commun. Dec. 2, 2017;493(4):1542-1547. doi: 10.1016/j.bbrc.2017.10.029. Epub Oct. 6, 2017. PMID: 28993191.
Qi et al. "Enhancement of neural stem cell survival, proliferation and differentiation by IGF-1 delivery in graphene oxide-incorporated PLGA electrospun nanofibrous mats" RSC Adv., 2019,9, 8315-8325.
Ranjit et al., "Potential neuroprotective role of astroglial exosomes against smoking-induced oxidative stress and HIV-1 replication in the central nervous system," Expert Opin Ther Targets. Aug. 2018; 22(8):703-714.
Rhee et al. "Neural stem cells secrete factors facilitating brain regeneration upon constitutive Raf-Erk activation." Sci Rep 6, 32025 (2016): doi org/10.1038/srep32025.
Sachdeva et al. "Klotho and the Treatment of Human Malignancies" Cancers 2020, 12, 1665; doi:10.3390/cancers12061665.
Sadagurski et al. "Insulin-like growth factor 1 receptor signaling regulates skin development and inhibits skin keratinocyte differentiation." Molecular and Cellular Biology vol. 26,7 (2006): 2675-87. doi:10.1128/MCB.26.7.2675-2687.2006.
Sanchez-Nino et al. "Klotho to Treat Kidney Fibrosis" J Am Soc Nephrol 24: 687-689, 2013. doi: 10.1681/ASN.2013030294.
Savastano et al. "Insulin-like Growth Factor-1, Psoriasis, and Inflammation: A Ménage à Trois?" European Journal of Inflammation vol. 9 issue: 3, pp. 277-283 (2011).
Schardong et al. "Effects of Intradialytic Neuromuscular Electrical Stimulation on Strength and Muscle Architecture in Patients With Chronic Kidney Failure: Randomized Clinical Trial." Artif Organs. Nov. 2017;41(11):1049-1058. doi: 10.1111/aor.12886. Epub Jun. 16, 2017. (Abstract Only).
Seo et al. "Renal Klotho expression in patients with acute kidney injury is associated with the severity of the injury" The Korean Journal of Internal Medicine (Jul. 2015);30(4):489-495.
Sharma et al. "Insulin demand regulates β cell number via the unfolded protein response." Journal of Clinical Investigation, 2015; DOI: 10.1172/JCI79264.

(56) References Cited

OTHER PUBLICATIONS

Sieg "Mini-review of neural regeneration peptides in brain development." Journal of Stem Cell Research & Therapeutics 1 (2016): DOI: 10.15406/JSRT.2016.01.00025 Corpus ID: 14566389.
Silva et al, "Analgesia Induced by 2- or 100-Hz Electroacupuncture in the Rat Tail-Flick Test Depends on the Activation of Different Descending Pain Inhibitory Mechanisms", The Journal of Pain, vol. 12, No. 1, Jan. 2011. (Year: 2011).
Sood et al. "Fetal Brain Extracellular Matrix Boosts Neuronal Network Formation in 3D Bioengineered Model of Cortical Brain Tissue" ACS Biomater. Sci. Eng. 2016, 2, 1, 131-140.
Spadaccio et al. "In Situ Electrostimulation Drives a Regenerative Shift in the Zone of Infarcted Myocardium" Cell Transplantation, vol. 21, pp. 493-503, 2013 (Final Acceptance Mar. 2012).
Stief et al. "Functional electromyostimulation of the corpus cavernosum penis—preliminary results of a novel therapeutic option for erectile dysfunction," World J. Urol. (1995) 13:243-247.
Sun et al. "Overexpression of Klotho suppresses liver cancer progression and induces cell apoptosis by negatively regulating wnt/β-catenin signaling pathway." World Journal of Surgical Oncology vol. 13 307. Oct. 24, 2015, doi: 10.1186/s12957-015-0717-0.
Takenaka et al. "[OP.4B.02] Klotho Supplementation Attenuates Blood Pressure and Oxidative Stress in Diabetes" Journal of Hypertension Sep. 2017—vol. 35—Issue—p. e38; doi: 10.1097/01.hjh.0000523076.42214.98.
Takenaka et al. "Klotho Ameliorates Medullary Fibrosis and Pressure Natriuresis in Hypertensive Rat Kidneys." Hypertension (Dallas, Tex. : 1979) vol. 72,5 (Nov. 2018): 1151-1159 doi:10.1161/HYPERTENSIONAHA.118.1117.
Chaudhari et al. "Modulating OPG and TGF-ß1 mRNA expression via bioelectrical stimulation" Bone Rep. Oct. 9, 2021;15:101141. doi: 10.1016/j.bonr.2021.101141. PMID: 34692946; PMCID: PMC8517839.
Goncalves et al. "Effect of EDTA on TGF-ß1 released from the dentin matrix and its influence on dental pulp stem cell migration" Braz Oral Res. Dec. 22, 2016;30(1):e131. doi:10.1590/1807-3107BOR-2016.vol30.0131. PIMID: 28001241.
Hu et al. "Towards Unraveling the Human Tooth Transcriptome: The Dentome" PLoS One 10(4) (2015): e0124801. doi: 10.1371/journal.pone.0124801.

* cited by examiner

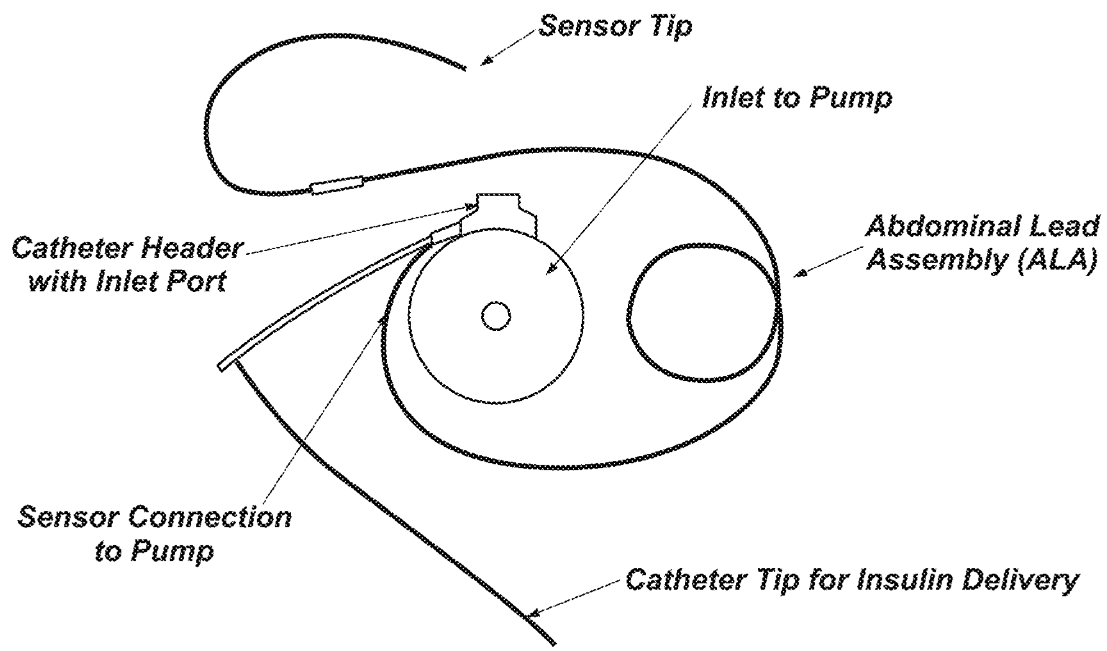
FIG. 3
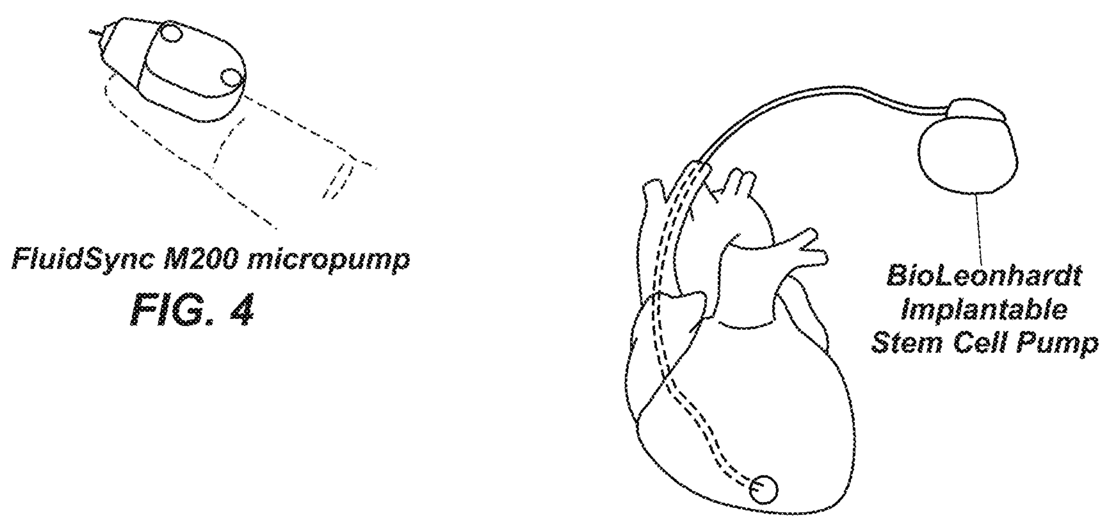
FIG. 4
FIG. 5

Acitívin B: 6.0mV, 150Hz, pulse width 100us, square wave

EGF: 10V/cm (5V here), 500Hz, pulse width 180us, square wave

Follistatin: 10V, 50Hz, Square wave

HGF: 3.5V, 10sec burst every 30 seconds, square wave

IGF-1: 3.0mV, 22Hz, square wave

OPG: 4.0mV, 2,000 Hz, square wave

PDGF30%: 3V/cm (100mV here), 10Hz, pulse width 200us, square wave

PDGF230%: 20V/cm (7.0V here), 100Hz, pulse width 100us, square wave

Proliferation: 15mV, 70Hz, square wave

Proliferation: 2.5-6.0V (4V here), 20Hz, pulse width 200-700us, square wave

RANKL: 3.0mV, 2Hz, square wave

SDF-1: 3.5mV, 30Hz, square wave

Tropoelastin: 60mV, 50Hz, square wave

VEGF: 100mV, 50Hz, square wave

SDF-1 (2nd part): 0.25mA (3.0V shown here), 100Hz, 100us pulse width, square wave

BIOELECTRIC STIMULATOR

CROSS-REFERENCE TO RELATED APPLICATIONS

This application is a continuation of co-pending U.S. Ser. No. 15/812,760, filed Nov. 14, 2017, which is a continuation-in-part of U.S. Ser. No. 15/460,129, filed on Mar. 15, 2017 (US 2017/0266371A1, Sep. 21, 2017), which itself claims the benefit under 35 USC § 119 of:

U.S. Provisional Patent Application Ser. No. 62/308,702, filed Mar. 15, 2016;

U.S. Provisional Patent Application Ser. No. 62/363,012, filed Jul. 15, 2016;

U.S. Provisional Patent Application Ser. No. 62/364,472, filed Jul. 20, 2016;

U.S. Provisional Patent Application Ser. No. 62/375,271, filed Aug. 15, 2016;

U.S. Provisional Patent Application Ser. No. 62/385,124, filed Sep. 8, 2016;

U.S. Provisional Patent Application Ser. No. 62/454,521, filed Feb. 3, 2017; and U.S. Provisional Patent Application Ser. No. 62/352,930, filed Jun. 21, 2016, the disclosure of each of which is incorporated herein in its entirety by this reference.

FIELD

The application relates generally to the field of medical devices and associated treatments, and more specifically to precise bioelectrical stimulation of a subject's tissue, augmented with the administration of a composition comprising, among other things, stem cells and nutrients, useful to stimulate and treat the subject, the subject's tissue(s), the subject's organ(s), and/or the subject's cells.

BACKGROUND

Various organs of the body lose, e.g., muscle function due to aging, disease, low blood flow, injury or blood vessel blockage(s). For example, the heart can become subject to heart failure. Realizing this, attempts have been made to address the issue with, e.g., electrical stimulation. For example, U.S. Pat. No. 7,483,749 to Leonhardt et al. (Jan. 27, 2009), the contents of which are incorporated herein by this reference, provided a method for enhancing myogenesis in a subject's injured myocardium, which method comprised identifying an injury or degeneration site in the myocardium and applying electrical stimulation to the site to enhance myogenesis. The method could be used in combination with implantation of myogenic cells into the myocardium, and the electrical stimulation could be applied before or after the implantation of myogenic cells. While good for its time, the method could be improved upon.

Prior art devices either did not produce follistatin at all or were of very high voltages (10 to 40V), which could lead to electrical disturbances in the heart tissue and which could be painful in use for applications such as treating erectile dysfunction.

BRIEF SUMMARY

Described is an organ regeneration stimulator pump and composition system.

Also described is bioelectric stimulator programmed to activate release in a subject of SDF1, IGF1, EGF, HGF, PDGF, eNOS, VEGF, Activin A and B, RANKL/OPG/TNF A, Follistatin, IL-6, HIF-1 Alpha, and tropoelastin. Described is a bioelectric stimulator including: a power source (e.g., battery, capacitor, or other suitable source of electricity), and means for delivering an electrical signal to a subject's tissue (e.g., via electrode(s) or wirelessly). The bioelectric stimulator utilizes the electrical signal to precisely control protein expression in the tissue on demand. Such a bioelectric stimulator preferably precisely controls release of SDF-1 in the subject, without diminishing effect over time.

Also described is a method of using the bioelectric stimulator to regenerate and/or recover an organ in a subject, the method including: delivering selected electrical signals to the organ so as to precisely control protein expressions in the right sequence and volume for total or near total organ regeneration and recovery. Such a method can further include separately delivering to the subject a cocktail of regenerative agents including any combination of the following: stem cells, endothelial progenitor cells, selected exosomes, selected alkaloids, selected anti-inflammatory agents, nutrient hydrogel, organ specific matrix, selected growth factors, amniotic fluid, placenta fluid, cord blood, and embryonic sourced growth factors and cells.

Also described is a method of using the bioelectric stimulator in a subject's tissue to control release of a protein, wherein the electrical signal stimulates the production of a protein selected from the group consisting of SDF-1, IGF-1, HGF, EGF, PDGF, VEGF, HIF 1 alpha, eNOS, activin A, activin B, IL-6, follistatin, tropoelastin, GDF-10, GDF-11, neurogenin 3, FGF, TGF, TNF alpha, RANKL, OPG, and any combination thereof.

Also described is a method of using the bioelectric stimulator in a subject to grow mature new blood vessels and repair existing blood vessels in a subject, the method including: generating electrical signals from the bioelectric stimulator to control the release of a protein, wherein the protein is selected from the group consisting of SDF-1, IGF-1, EGF, HGF, PDGF, eNOS, HIF 1 alpha, tropoelastin, GDF-10, GDF-11, and any combination thereof.

Also described is a method of using the bioelectric stimulator in a subject to regenerate brain cells, the method including: generating electrical signals from the bioelectric stimulator to control the release of a protein, wherein the protein is selected from the group consisting of SDF-1, IGF-1, HGF, GDF-10, GDF-11, activin A, activin B, eNOS, HIF 1 alpha, neurogenin 3, PDGF, tropoelastin, and any combination thereof. Such a method can further include: separately delivering to the subject stem cells and/or growth factors including any combination of GDF-10, GDF-11, SDF-1, IGF-1, HGH, activin A, activin B, eNOS, HIF 1 alpha, IL-6, PDGF, HGF, and tropoelastin.

Also described is a method of using the bioelectric stimulator in a subject to repair and grow muscle, the method including: generating electrical signals from the bioelectric stimulator to control the release of a protein, wherein the protein is selected from the group consisting of SDF-1, IGF-1, HGF, EGF, myoblast injections, cardiac muscle stem cell injections, immature myoblasts, PDGF, HGF, follistatin, tropoelastin, HGF, Human Growth Hormone (HGH), pyruvate, HIF 1 alpha, and any combination thereof.

Also described is a method of using the bioelectric stimulator in a subject to repair DNA, the method including: generating electrical signals from the bioelectric stimulator to control the release of IGF-1.

Also described is a method of using the bioelectric stimulator to achieve a desired result in a subject, wherein the desired result is selected from the group consisting of brain regeneration, cognitive function brain improvement, brain stroke and traumatic injury recovery, hair regeneration, eye regeneration, ear hearing regeneration, skin regeneration, tooth regeneration, dental gum regeneration, tooth root canal regeneration, accelerated tooth movement, stabilization of tooth position, sub-mucosa regeneration, breast tissue generation, aorta regeneration, limb regeneration, artery regeneration, heart regeneration, heart valve regeneration, kidney regeneration, pancreas regeneration, bladder regeneration, liver regeneration, joint regeneration, bone regeneration, and any combination thereof.

Also described is a method of using the bioelectric stimulator to achieve a desired result, wherein the desired result is selected from the group consisting of improving quantity and quality of fish in aquaculture systems, improving milk production in a mammal, renewing strength and vitality in living animals, building increase muscle strength, improving urine output, and any combination thereof.

Also described is a bioelectric stimulator including: a power source (e.g., battery, capacitor, or other suitable source of electricity), and means for delivering an electrical signal to a subject's tissue (e.g., via electrode(s) or wirelessly), wherein the bioelectric stimulator utilizes the electrical signal to precisely control stem cell homing, proliferation and differentiation in the tissue on demand. Such a bioelectric stimulator preferably utilizes the electrical signal to precisely control protein expression. Also described is a method of using such a bioelectric stimulator to regenerate and/or recover an organ in a subject, the method including delivering an electrical signal to the organ with the bioelectric stimulator.

A preferred system includes:

1. A bioelectric stimulator that controls/stimulates the release/production of SDF1, IGF1, EGF, HGF, PDGF, eNOS, VEGF, Activin A and B, RANKL/OPG/TNF A, Follistatin, IL-6, HIF-1 Alpha, and tropoelastin. In certain embodiments, it also releases/stimulates GDF-10, GDF-11, Relaxin, FGF, TGF, and/or neurogenin-3.
2. A micro infusion pump (e.g., a FluidSyncm micropump available from Fluidsynchrony of Pasadena, CA, US), which is programmable and re-fillable and preferably has a low cell damage design. Such a pump preferably includes a refilling silicon septum port or ports and reservoir chambers.
3. A multi-component organ regeneration composition that includes (depending on the application) adipose-derived stem cells, muscle-derived stem cells (when needed for muscle), exosomes, Micro RNAs, nutrient hydrogel, growth factor cocktail, organ specific matrix, selected alkaloids, and/or selected anti-inflammatory agents.

The pump and stimulator may be associated with (e.g., connected to) the organ to be treated/regenerated with a pacing infusion lead (available from Nanoscribe of Eggenstein-Leopoldshafen, Germany). The interface with the organ varies by organ, e.g., a conductive soft wrap can be used for certain applications.

The stimulator can be designed to externally deliver all regeneration promoting signals wirelessly to the subject's organ(s), tissue(s), and/or cells.

In certain embodiments, described is a preferred device for regenerating organs by controlled release of organ regenerating promoting proteins by a bioelectric stimulator. Such a device may utilize bioelectric signals delivered wirelessly to the organ(s), tissue(s), and/or cell(s) being treated. Such a device may utilize bioelectric organ regeneration signals delivered via the nervous system of the subject being treated.

In certain embodiments, described is a device for regenerating organs by controlled release of stem cell homing signals (SDF-1 and PDGF), stem cell differentiation signals, blood vessel growth signals, and organ specific tissue building signals.

Blood vessel growth signals are, e.g., first, for VEGF, then for SDF-1, then PDGF, then HIF 1 alpha, then eNOS, then tropoelastin, then HGF, followed by the signals for EGF. VEGF signals followed by SDF-1 are especially preferred.

In certain embodiments, also described is a device for regenerating organs by controlled release of, e.g., SDF-1, IGF-1, HGF, EGF, PDGF, eNOS, VEGF, follistatin, Activin A and B, Relaxin, tropoelastin, GDF-10, GDF-11 and Neurogenin-3 by bioelectric stimulation.

In certain embodiments, described is a system for regenerating organs, the system comprising: an optional bioelectric stimulator that controls release of organ regeneration promoting proteins; a re-fillable micro infusion pump; a mixed organ regeneration composition of stem cells and growth factors; and electrical pacing and infusion lead(s) directed to with tip inserted into the organ(s) to be treated. Such a device may include a mixed composition including any or all of the following components: SDF-1, IGF-1, PDGF, IL-6, HIF-1 Alpha, follistatin, tropoelastin, relaxin, GDF-10, GDG-11, HGF, EGF, eNOS, VEGF, adipose derived stem cells, iPS cells, cardiac derived stem cells, skeletal muscle derived muscle progenitor cells, endothelial cells, stromal fraction, selected exosomes, selected Micro RNAs, selected alkaloids, selected anti-inflammatory agents, organ specific matrix, and/or nutrient hydrogel.

While not intending to be bound by theory, the following might help to explain the results obtained with the use of the system. Successful organ treatment and/or regeneration is like good farming. A farmer needs soil pre-preparation, well-designed seeds, sun, irrigation, fertilizers, pruning, and protection against elements and enemies for a good crop. The same is needed for good organ treatment with, e.g., bioelectrical stimulation. The entire ecosystem should be enhanced.

Furthermore, in certain embodiments, only non-invasive bioelectric stimulation controlled protein release is first used before introducing a micro infusion pump or multi-component composition. The pump and composition are best used in severe disease states.

In such embodiments, the scarred organ tissue is first prepared before stem cell recruitment by changing the milieu so that when the stem cells arrive they know how they should differentiate. For example, a bald head is changed to a "hair milieu" so that when stem cells are recruited with the SDF-1 homing signal to the bald head the stem cells "know" to become hair, not more bald head tissue.

In another such example, post-heart attack scar tissue is changed to a "muscle milieu" so that when stem cells are recruited with the SDF-1 homing signal to the scar, they "know" to become muscle, not more fibroblasts that make up scar tissue.

As a further example, a new blood supply is grown in a previously injured organ tissue and it is loaded up with nutrients so that when the stem cells arrive, they proliferate and thrive in forming the new healthy tissue.

The most important and most difficult to achieve bioelectric signals are the ones that control stem cell differentiation into useful tissue. The bioelectric signals are also the ones that require the most precise control by the micro stimulator. A little bit to the left of right with the signal and you get bone or fat in the heart instead of stem cells differentiating into cardiac muscle tissue. In situations where the milieu change my not be optimal, this is the only way known to get new good organ tissue.

Controlled follistatin release is also useful for treating other ailments such as erectile dysfunction, aortic aneurysms, and failing heart valves. Also, it can assist in heart regeneration, Peyronie's disease, sport trauma, aortic aneurysm repair, heart valve repair, artery repair, diabetic foot ulcer repair, leg repair, growing teeth and as a muscle building product.

The herein described system can produce/may be adapted to regenerate other organs including: skin, face, aorta, heart, eyes, arteries, joints, heart valves, limbs, lungs, kidneys, pancreas, liver, bladder, whole body, biological pacemaker, and breasts, and to treat erectile dysfunction, COPD, snoring, and incontinence.

BRIEF DESCRIPTION OF THE DRAWINGS

FIG. 3 depicts an interface for use with the system.

FIG. 4 depicts a micropump for use with the system.

FIG. 5 depicts a pump associated with a subject's heart.

DETAILED DESCRIPTION

In a preferred embodiment, the organ regeneration composition hereof comprises adipose-derived stem cells, bone marrow-derived stem cells, muscle-derived stem cells (e.g., when needed for muscle), exosomes, MicroRNAs, nutrient hydrogel, growth factor cocktail, organ specific matrix, selected alkaloids, and/or selected anti-inflammatory agents.

Figure 1:
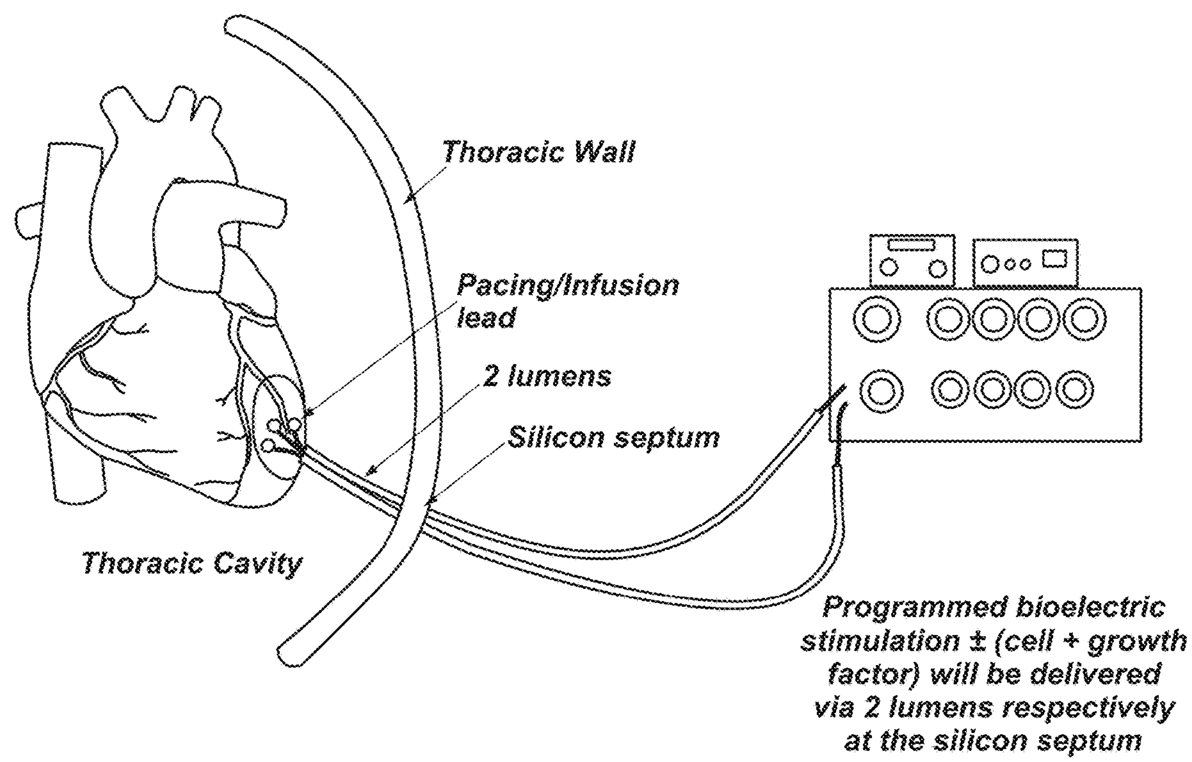
FIG. 1 depicts a programmed bioelectric stimulator (with or without cell and growth factor) for delivery to the heart of a human subject via two lumens respectively at a silicon septum.
Figure 2:
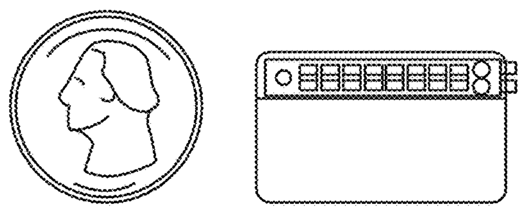
FIG. 2 depicts a programmed bioelectric stimulator depicted alongside a U.S. quarter.

Referring now to FIG. 1, depicted is a human use stimulator and pump for use with treatment of, e.g., the heart. Preferably, such a device is about the size of two quarters (available from QIG Greatbatch/Greatbatch, Inc. of Frisco, TX, US) (FIG. 2) and is programmable and re-fillable with low cell damage design. Refilling may be by silicon septum ports and reservoir chambers. Depicted particularly in FIG. 1 are the subject's heart, the pacing lead, the infusion lead, the thoracic cavity, two lumens, thoracic wall, silicon septum, and a larger programmed/programmable bioelectric stimulator with composition (e.g., cells and growth factors) for delivery via two lumens via the silica septum. The microinfusion pump for continuous or repeat delivery of a liquid composition, which microinfusion pump includes silicon septum ports and associated reservoir chambers connected to the bioelectric stimulator microinfusion pump to the tissue with a pacing infusion lead.

The described system is currently being investigated for various applications including heart and cardiovascular (e.g., heart regeneration, aorta regeneration, biological pacemaker regeneration, heart valve regeneration, artery regeneration, limb blood flow improvement and limb salvage, and wireless diabetic foot ulcer treatment), brain (e.g., brain regeneration, stroke, concussion, Parkinson's, Alzheimer's, memory and cognitive function improvement, cerebral aneurysm treatment and cancer, and cognitive function improvement), cosmetic & personal care (e.g., breast regeneration, dental gum regeneration and tooth pulp storage, orthodontics, skin regeneration, erectile dysfunction treatment, and hair regeneration), major organ regeneration (e.g., eye, pancreas regeneration, lung, liver regeneration, kidney regeneration, ear hearing, bladder regeneration, whole body regeneration, and sub-gastric mucosa), and associated cancer treatment (e.g., some organ specific technology platforms have integrated cancer tumor stoppage signals).

The described system may be incorporated into, for example, a whole body regeneration chamber that scans and/or analyzes the body for its deficiencies and precisely delivers the right stem cells and proteins to the right location at the right time combined with programmed infusion of whole body regeneration substances. Ultimately, the goal for the technology is whole and complete body regeneration, every organ.

The organ specific matrix is a composition comprising cells of an organ which is to be treated. The organ specific matrix is believed to aid in stem cell differentiation, but in any event is found to be useful in the composition. It has been found that for the multicomponent composition, cells plus selected growth factors are better than just cells alone. See, e.g., Prochizka et al. "Therapeutic Potential of Adipose-Derived Therapeutic Factor Concentrate for Treating Critical Limb Ischemia," Cell Transplantation, 25(9), pp. 1623-1633(11) (2016) and "Cocktail of Factors from Fat-derived Stem Cells Shows Promise for Critical Limb Ischemia," world wide web at sciencenewsline.com/news/2016012204520017.html (Jan. 22, 2016), the contents of each of which are incorporated herein by this reference.

In case of an advanced disease state, a micro infusion pump (e.g., FIGS. 3-5) is used for daily delivery of, e.g., 2 ml of organ regeneration composition (comprised of adipose-derived cells or bone marrow-derived mesenchymal stem cells plus cocktail of growth factors (usually derived from amniotic fluid or placenta), selected Micro RNAs, selected alkaloids, selected anti-inflammatory agents, nutrient hydrogel, organ specific matrix, selected exosomes). For muscle regeneration, immature myoblasts are included in the composition.

Exosomes represent a specific subset of secreted membrane vesicles, which are relatively homogeneous in size (30-100 nm). Exosomes have been proposed to differ from other membrane vesicles by its size, density, and specific composition of lipids, proteins, and nucleic acids, which reflect its endocytic origin Exosomes are formed in endosomal vesicles called multivesicular endosomes (MVEs) or multivesicular bodies, which originate by direct budding of the plasma membrane into early endosomes. The generation of exosomes to form MVEs involves the lateral segregation of cargo at the delimiting membrane of an endosome and inward budding and pinching of vesicles into the endosomal lumen. Because exosomes originate by two successive invaginations from the plasma membrane, its membrane orientation is similar to the plasma membrane. Exosomes from many cell types may contain similar surface proteins as the cell from which it is derived. Membrane proteins that are known to cluster into microdomains at the plasma membrane or at endosomes, such as tetraspanins (CD63, CD81, CD82), often are also enriched in EVs. It is also thought that endosomal sorting complex responsible for transport system and tetraspanins, which are highly enriched in MVEs, play a role in exosome production. How cytosolic constituents are recruited into exosomes is unclear but may involve the association of exosomal membrane proteins with chaperones, such as HSC70, that are found in exosomes from most cell types. MVEs are also sites of miRNA-loaded RNA-induced silencing complex accumulation, and the fact that exosome-like vesicles are considerably enriched in GW182 and AGO2 implicates the functional roles of these proteins in RNA sorting to exosomes. Exosomes are released to the extracellular fluid by fusion of MVE to the plasma membrane of a cell, resulting in bursts of exosome secretion. Several Rab GTPases such as Rab27a and Rab27b, Rab11 and Rab35, all seem to be involved in exosomes release.

Repeat doses of the composition are also preferred. See, e.g., Gavira et al. "Repeated implantation of skeletal myoblast in a swine model of chronic myocardial infarction," *Eur Heart J,* 31(8): 1013-1021. doi: 10.1093/eurheartj/ehp342 (2010), the contents of which are incorporated herein by this reference.

For heart muscle regeneration, immature myoblasts and cardiac-derived progenitors cells as well as endothelial progenitor cells (EPCs) may be included in the composition.

Generally, the system hereof involves a bioelectric stimulator controlling release of SDF-1, IGF-1, HGF, EGF, VEGF, PDGF, eNOS, follistatin, Activin A and B, and tropoelastin. Optionally and in certain applications, GDF-10, GDF-11, Neurogenin-3 and Relaxin may also be included.

SDF-1 is generally for recruiting stem cells and maturing blood vessels. IGF-1 is for DNA repair. HGF is for tissue regeneration and reduces arrhythmias in the case of heart. EGF grows tissue. VEGF grows blood vessels. PDGF is a second stem cell homing factor and helps tissue regeneration especially heart. eNOS dilates blood vessels. Follistatin promotes muscle growth. Activin A and B regenerates nerve cells and neurons. Tropoelastin increases elasticity of all tissues especially arteries, skin, heart, aorta. GDF-10 and GDF-11 promote regeneration especially of nerve cells and neurons. Neurogenin-3 is especially helpful in brain and pancreas regeneration. Relaxin helps heart regeneration.

The micro voltage signal generator may be produced utilizing the same techniques to produce a standard heart pacemaker well known to a person of ordinary skill in the art. An exemplary microvoltage generator is available (for experimental purposes from Cal-X Stars Business Accelerator, Inc. DBA Leonhardt's Launchpads or Leonhardt Vineyards LLC DBA Leonhardt Ventures of Salt Lake City, UT, US). The primary difference is the special electrical stimulation signals needed to control, e.g., precise follistatin release on demand (which signals are described later herein). The leading pacemaker manufacturers are Medtronic, Boston Scientific Guidant, Abbott St. Jude, BioTronik and Sorin Biomedica.

Construction of the electric signal generators and pacemakers, are known in the art and can be obtained from OEM suppliers as well as their accompanying chargers and programmers. The electric signal generators are programmed to produce specific signals to lead to specific protein expressions at precisely the right time for, e.g., optimal organ treatment or regeneration.

The pacing infusion lead may be constructed or purchased from the same suppliers that build standard heart pacemaker leads. Pacing infusion leads may be purchased from a variety of OEM vendors. The pacing infusion lead may, for example, be a standard one currently used in heart failure pacing studies in combination with drug delivery.

An infusion and electrode wide area pitch may be constructed by cutting conduction polymer to shape and forming plastic into a flat bag with outlet ports in strategic locations.

Micro stimulators may be purchased or constructed in the same manner heart pacemakers have been made since the 1960's. Micro infusion pumps can be purchased or produced similar to how they have been produced for drug, insulin, and pain medication delivery since the 1970's. The programming computer can be standard laptop computer. The programming wand customary to wireless programming wands may be used to program heart pacers.

Any one of the protein expression signals work well on their own for organ regeneration, but they work better together. SDF-1 is the most powerful regeneration protein followed by IGF-1.

Wireless, single lumen infusion pacing lead or infusion conduction wide array patch may all be used to deliver the regeneration signals and substances to the organ of interest to be treated or they may be used in combination.

A re-charging wand for use herein is preferably similar to the pacemaker re-charging wand developed by Alfred Mann in the early 1970's for recharging externally implantable pacemakers.

Figure 21:
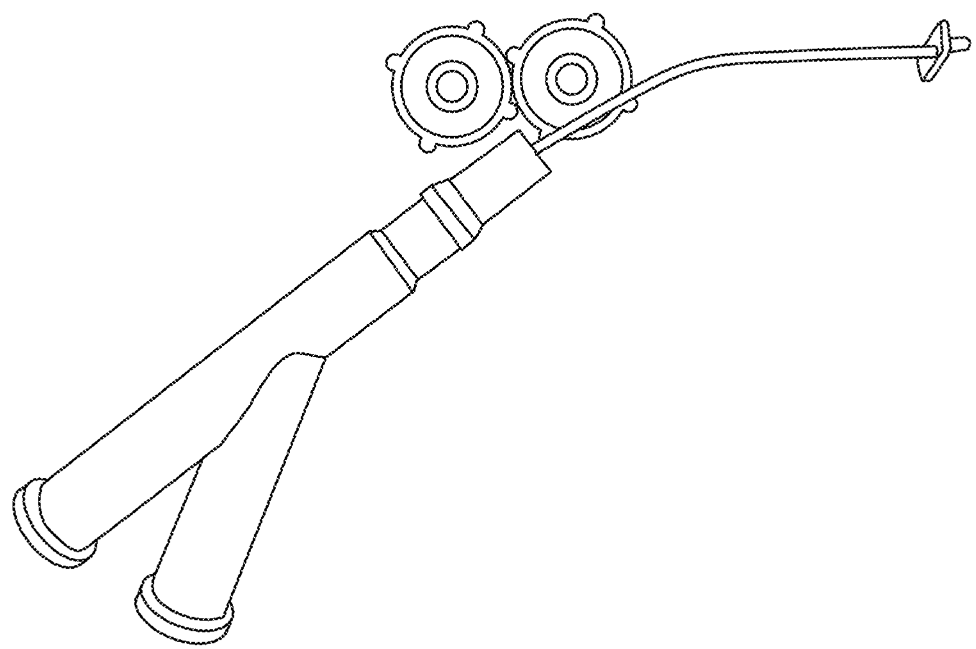
FIG. 21 depicts a combination bioelectric stimulation and stem cells and growth factors infusion catheter.

FIG. 21 depicts a combination bioelectric stimulation and stem cell and growth factor(s) infusion catheter usable with the described system.

Figure 22:
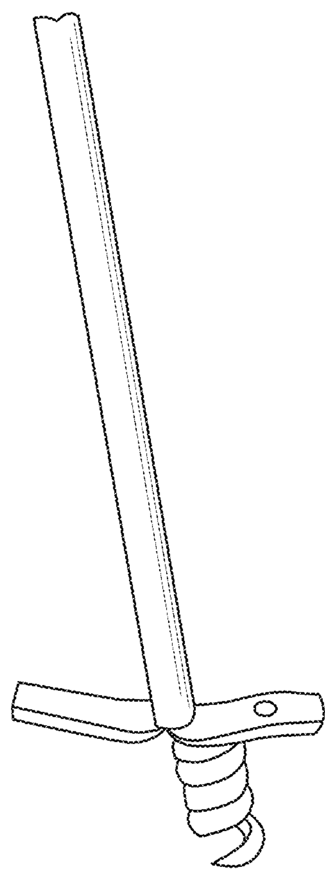
FIG. 22 is a close up view of the conductive and infusion cork screw tip for use with the catheter system of FIG. 21.

A corkscrew tip may be of a standard type utilized to secure most heart pacemakers in heart tissue. Wireless delivery of the signal or electro-acupuncture needle delivery is included. FIG. 22 is a close up of the conductive and infusion cork screw tip for getting deep into target tissue. The tip include suture tabs for even more secure fixation to the target organ.

Additionally, the micro stimulator and micro pump and regeneration composition and bioelectric signaling programming may be used to generate tissue(s) and/or organ(s), such as hair and skin. Alternatively, the system may be used for hair removal.

With respect to hair regeneration, the expression signals for hair regeneration promoting growth factors/proteins are described herein as are the study durations for each signal. Particularly described are a method and apparatus for producing hair growth stimulation using bioelectric energy, topical compositions, stem cell/growth factor micro infusions and combinations thereof. By using bioelectric signaling resulting from specific protein expressions and their cellular responses to exposure to specific micro voltages. The described system controls release of SDF-1 a stem cell homing factor as well as IGF-1, HGF, EGF, follistatin, tropoelastin, eNOS and VEGF as well as micro infusion delivery of an, e.g., 15 component hair regeneration cocktail which includes nutrient hydrogel, thus providing all the supporting element to grow a full head of hair.

A preferred composition includes adipose-derived cells (or bone marrow derived MSCs or any pluripotent stem cell, such as iPS cells) and growth factor mix which should include (SDF-1, IGF-1, EGF, HGF, PDGF, VEGF, eNOS, activin A, activin B, follistatin, relaxin, GDF-10, GDF-11 and tropoelastin plus selected exosomes (miR-146a, miR-294, mES-Exo) plus selected alkaloids (harmine and tetrahydroharmine) plus selected anti-inflammatory factors plus nutrient hydrogel (IGF-1, SDF-1, HGF plus FGF) plus organ specific matrix. For regenerating muscle, one includes into the composition skeletal muscle or cardiac muscle-derived cells. Also, preferably included are amniotic fluid, placenta, or cord blood when available.

For heart treatment/regeneration (e.g., for treating congestive heart failure), the compositions may be modified to include: cardiac tissue biopsy derived cells, adipose tissue-derived cells, skeletal muscle derived cells (immature myoblasts (Tamaki selection process—Tamaki et al. "Cardiomyocyte Formation by Skeletal Muscle-Derived Multi-Myogenic Stem Cells after Transplantation into Infarcted Myocardium," *PLoS ONE* 3(3): e1789. doi:10.1371/journal.pone.0001789 (2008), the contents of which are incorporated herein by this reference)), nutrient hydrogel, selected growth factors (SDF-1, PDGF, HGF, IGF-1, follistatin, relaxin, tropoelastin, eNOS, VEGF, and EGF), exosomes, alkaloids, anti-inflammatory agent(s), cardiac matrix soaked in selected growth factors, and Micro RNAs.

For human use, longer repeat doses are needed and a natural release from a patient's own electrically stimulated cells leads to successful human heart regeneration. For example, the described signals for follistatin release match more closely with the natural low voltage signals in the human body.

In a booster composition for heart treatment/regeneration, the composition may include: adipose tissue-derived cells, cardiac tissue-derived cells, skeletal muscle derived cells—immature myoblasts (Tamaki selection process—cardiac progenitor—Tamaki et al. supra (2008)), growth factors (SDF-1, PDGF, HGF, Follistatin, and IGF-1), and cardiac matrix. In the basic composition for heart treatment/regeneration, the composition may include: adipose tissue-derived cells and muscle-derived immature myoblast cells (Tamaki process selection—see Tamaki et al. supra (2008)) or cardiac derived cells, together with selected growth factors (SDF-1, PDGF, HGF, and Follistatin).

There are three compositions, i.e., a basic composition, an intermediate composition, and an advanced composition. The basic composition includes MSCs or adipose derived cells, amniotic fluid, and myoblasts. The intermediate composition includes the ingredients of the basic composition together with a cocktail of growth factors (Follistatin rich). The advanced composition is adipose-derived or bone marrow-derived stem cells (MSCs), endothelial progenitor cells, selected growth factors cocktail, selected exosomes, selected Micro RNAs, selected alkaloids, selected anti-inflammatory agents, nutrient hydrogel, organ specific matrix, amniotic fluid (240 growth factors), and cardiac derived cells or immature myoblasts.

The concentration of cells in the compositions is preferably about 50,000,000 cells/ml. The amniotic fluid is preferably as described in Pierce et al. "Collection and characterization of amniotic fluid from scheduled C-section deliveries," Cell Tissue Bank, DOI 10.1007/s10561-016-9572-7 (Springer, 2012) and is available from Irvine Scientific.

In certain embodiments, an organ regeneration mixed composition (e.g., a cardio angiogenic and cardio myogenic "cocktail" for heart treatment/regeneration) is loaded into a micro infusion pump (or in the case of limb salvage injected directly in the patient's leg with a needle and syringe). The pump may be refilled, e.g., weekly to achieve a slow, timed infusion delivery of the composition to the heart scar tissue. Administration of the composition(s) is combined with bioelectric stimulation to control the release of more than twelve regeneration promoting proteins. Treatment times for assisting the heart may last 36 months.

For treating heart failure, a single (prior art) injection session is insufficient to fully recover a failing organ especially a failing heart. Furthermore, injecting just one cell type alone one time is not enough for full organ recovery. Bioelectric stimulation for controlled release of SDF-1 in a subject is powerful to improve organ regeneration results. Bioelectric stimulation controlled release of VEGF, eNOS and SDF is powerful in improving blood flow to a failing organ. Nutrient hydrogels and organ specific matrixes can highly improve cell transplantation results. A mix of growth factors provides better organ recovery results than just one growth factor or just one cell type. Bioelectric stimulation controlled release of a variety of growth factors offers more improvement than just one. Hepatocyte growth factor not only aides in organ regeneration, but also reduces arrhythmias risk in the heart. Follistatin injected or released via bioelectric stimulation can greatly improve muscle based organ regeneration results. Tropoelastin can improve elasticity of any treated organ, which in itself is valuable and is deemed to be especially valuable in the heart. An implantable micro infusion re-fillable programmable pump designed to reduce cell damage is better than injecting the patient's heart numerous times with separate procedures.

Bioelectric stimulation can be done with the described microstimulator, which has a pacing infusion lead with a corkscrew lead placed/attached at, e.g., the center of heart scar tissue. The microstimulator is actuated and runs through programmed signals to signal the release of, e.g., SDF-1 and a differentiation signal. Described is a method of activating a tissue to differentiate a stem cell or to stimulate the tissue to produce a protein. The protein is selected from the group consisting of insulin-like growth factor 1 ("IGF1"), epidermal growth factor ("EGF"), hepatocyte growth factor ("HGF"), platelet-derived growth factor ("PDGF"), endothelial NOS ("eNOS"), vascular endothelial growth factor ("VEGF"), activin A, activin B, receptor activator of nuclear factor kappa-B ligand ("RANKL"), osteoprotegerin ("OPG"), tumor necrosis factor alpha ("TNF A"), follistatin, interleukin 6 ("IL-6"), hypoxia-inducible factor 1-alpha ("HIF-1-alpha"), and tropoelastin, the method including: stimulating the, e.g., human tissue with an electrical signal appropriate for the protein and tissue.

In such a method, when the electrical signal includes (within 15%): 0.1V applied at a frequency of about 50 Hz with a duration of about three (3) minutes (wherein the electrical signal is as measured three (3) mm deep into the tissue), the protein produced is VEGF.

In such a method, when the electrical signal includes (within 2%): 200 picoamps for about 10 seconds for about one (1) hour and the pulse has an amplitude of about 5 volts and a width of about 0.5 milliseconds for about 1 hour, with a duration of about one (1) minute (wherein the electrical signal is as measured three (3) mm deep into the tissue), stem cells differentiate.

In such a method, when the electrical signal includes (within 15%): 10V at 50 Hz and 100 Hz for about 12 hours each (duration 1 minute) (wherein the electrical signal is as measured three (3) mm deep into the tissue), the protein produced is follistatin.

In such a method, when the electrical signal includes (within 15%): 3.5 V stimulation in 10 second bursts, 1 burst every 30 seconds at a frequency of about 50 HZ (duration 5 minutes) (wherein the electrical signal is as measured three (3) mm deep into the tissue), the protein produced is HGF.

In such a method, when the electrical signal includes (within 15%): 3 mV with a frequency of about 22 Hz, and a current of about 1 mA for about fifteen (15) minutes and 3 mA for about fifteen (15) minutes (duration 5 minutes) (wherein the electrical signal is as measured three (3) mm deep into the tissue), the protein produced is IGF-1.

In such a method, when the electrical signal includes (within 15%): 0.06 V with 50 Hz alternating electrical field and a current of about 1 mA for about fifteen (15) minutes and 3 mA for about fifteen (15) minutes (duration 2 minutes) (wherein the electrical signal is as measured three (3) mm deep into the tissue), the protein produced is tropoelastin.

In such a method, when the electrical signal includes (within 15%): alternating high-frequency (HF) and medium-frequency signals (MF), symmetric, biphasic, trapezoid pulses, with 400-μs pulse duration and 1.5/1-s ramp-up/ramp-down duration, respectively (wherein the electrical signal is as measured three (3) mm deep into the tissue), the protein produced is eNOS. In such a method, when the HF consists of about 75 Hz pulses with six (6) seconds on and 21 seconds off for about fifteen (15) minutes. In such a method, when the MF consists of about 45 Hz pulses with 5 seconds on 12 seconds off for about fifteen (15) minutes followed by stimulation duration set as 20 minutes. In such a method, when the electrical signal includes (within 15%): 1 Hz stimulation, stimulation applied for about nine (9) seconds, followed by a one (1) second silent period, a total of about 1080 stimulations for about 20 minutes. In such a method, when the electrical signal includes (within 15%): 20 Hz stimulation, stimulation applied for about two (2) seconds, followed by silent period for about 28 seconds, a total of about 1600 stimulations for about 20 minutes (duration 2 minutes).

In such a method, when the electrical signal includes (within 15%): 6 mV at 150 Hz, monophasic square wave pulse 0.1 ms in duration current of fifteen (15) mA for about fifteen (15) minutes (duration two (2) minutes) (wherein the electrical signal is as measured three (3) mm deep into the tissue), the protein produced is Activin B.

In such a method, when the electrical signal includes (within 15%): 10 V/cm, pulse-width 180 μs, 500 Hz (duration nine (9) minutes) (wherein the electrical signal is as measured three (3) mm deep into the tissue), the protein produced is EGF.

For example, upregulation of RANKL, IGF-1, VEGF, and SDF-1 was achieved in cardiomyocytes using such signals. Upregulation of SDF-1 was achieved in pig heart. Upregulation of VEGF, endothelial NOS ("eNOS"), hypoxia-inducible factor 1-alpha ("HIF-1-alpha"), and IL-6 was achieved in eye cells. Upregulation of RANKL and osteoprotegerin ("OPG") was achieved in bone, tooth and gum.

Also described is a method of activating a tissue to produce stromal cell-derived factor 1 ("SDF1"), the method including: stimulating the (e.g., human) tissue with an electrical signal, wherein the electrical signal includes (within 15%): 30 pulses per second with a voltage of about 3.5 mV, and successively alternating currents of about 700 to 1500 picoamps for about one minute, and again with 700 to 1500 picoamps for about one minute and stimulated with current of about 0.25 mA, pulse duration of about 40 pulses/s, pulse width of about 100 μs, wherein the electrical signal is as measured three (3) mm deep into the tissue.

Further described is a method of activating a tissue to attract a stem cell, the method including: stimulating the (e.g., human) tissue with an electrical signal, wherein the electrical signal includes (within 2%): fifteen (15) mV and a current of about 500 picoamps at 70 pulses per minute for about three (3) hours and 20 pulses per minute, a pulse amplitude of from about 2.5-6 volts, and a pulse width of from about 0.2-0.7 milliseconds for about three (3) hours for about three (3) minutes, wherein the electrical signal is as measured three (3) mm deep into the tissue.

A combination bioelectric stimulator that controls release in the scarred heart of SDF-1, IGF-1, HGF, EGF, eNOS, VEGF, Activin A and B, follistatin, tropoelastin, GDF-10, GDF-11 and Neurogenin 3 combined with repeat delivery of a mixed stem cell and growth factor cardiac matrix composition via an implantable re-fillable micro infusion pump may be advantageously used.

In some cases, SDF-1 recruits via a presumed homing signal new reparative stem cells to the damaged organ. VEGF causes new nutrient and oxygen producing blood vessels to grow into the area being treated. IGF-1 repairs damaged cells, tissues and organs. Follistatin repairs damaged muscle. Tropoelastin adds elasticity to treated tissues making them more compliant. HGF aides in all repair processes and in the specific case of the heart regeneration reduces the risk of arrhythmias. All of these proteins work together to fully regenerate an organ over time.

The healing process can be accelerated with the use of a micro infusion pump that is filled with various types of stem cells and growth factors and in some cases drugs.

In certain embodiments relating to the treatment of cancer and tumors, described is a method of inhibiting the growth of cancer cells in a target region, wherein the method includes treating the cancer cells with an anti-cancer drug; and applying an electric field to the target region for a period of time, wherein the electric field has frequency and field strength characteristics selected to inhibit the growth of cancer cells in the target region. In such a method, in the applying step, the field may be applied in at least two different directions in an alternating sequence.

In such a method, the drug dosage may be less than 20% of a standard dosage for the drug.

In such a method, the period of time is typically at least 24 hours.

In such a method, the field strength is typically at least 1 V/cm.

In such a method, the drug typically comprises at least one of paclitaxel, doxorubicin cyclophosphamide, and cisplatin. In such a method, the field strength is typically at least 1 V/cm and the period of time is at least 24 hours.

Also described in certain embodiments is a method of killing or inhibiting the growth of cancer cells in a target region, wherein the method includes applying an electric field to the target region for a period of time while the cancer cells are being treated with an anti-cancer drug, wherein the electric field has a field strength in the target region of at least 1 V/cm. In such a method, the drug dosage is less than 20% of a standard dosage for the drug. In such a method, the period of time is at least 24 hours. In such a method, the drug comprises at least one of paclitaxel, doxorubicin cyclophosphamide, and cisplatin. In such a method, the field strength is between 1 V/cm and 5 V/cm and the period of time is at least 24 hours. In such a method, in the applying step, the field is applied in at least two different directions in an alternating sequence. Typically, the drug comprises cyclophosphamide, and typically, the period of time is at least 6 hours.

What follows are preferred signals from the stimulator. For example, described are two PDGF expression control signals, one low voltage and one higher voltage. The test tissue is sheep heart tissue. The test cells are mesenchymal stem cells.

30% PDGF increase>3 V/cm, 10 Hz, 2 micro amps (0.000002 amps) and the pulse duration 0.2 ms.

230% PDGF increase>20 V/cm 100 Hz, 0.25 mA (2.5e-7 amps) and pulse duration of 40 pulses/s, width of 100 μs.

40 minute treatment cycles 2 times a week for 4 weeks and then 3 times a week for 12 weeks.

PDGF Signal: 20 V for 1 minute, 20 mV for 10 minutes, current of 0.25 mA, pulse duration of 40 pulses/s, pulse width of 100 μs, and frequency of 100 Hz for 5 minutes followed by 528 Hz for 3 minutes and 432 Hz for 3 minutes and 50 Hz for 3 minutes.

VEGF—Blood vessel sprouting growth: 0.1V applied at a frequency of 50 Hz. Duration 3 minutes.

SDF-1—Stem cell recruiting signal: 30 pulses per second with a voltage of 3.5 mV, and successively alternating currents of 700 to 1500 picoamps for one minute, and again with 700 to 1500 picoamps for one minute and stimulated with current of 0.25 mA, pulse duration of 40 pulses/s, pulse width of 100 μs, and frequency of 100 Hz—each signal for 40 minutes to 8 hours a day for 2 to 36 months as needed for ideal results. Duration 7 minutes.

Stem cell proliferation signals: 15 mV and a current of 500 picoamps at 70 pulses per minute for 3 hours and 20 pulses per minute, a pulse amplitude of from 2.5-6 volts, and a pulse width of from 0.2-0.7 milliseconds for 3 hours. Duration 3 minutes.

Stem cell differentiation signals to become muscle: 200 picoamps for 10 seconds for 1 hour and the pulse has an amplitude of 5 volts and a width of 0.5 milliseconds for 1 hour. Duration 1 minute.

Another method is to reverse polarity and drop the voltage.

Follistatin—(muscle growth) production signal: 10 V at 50 Hz and 100 Hz 0.25 mA. Duration 1 minute.

HGF—Hepatocyte growth factor (arrhythmia reduction) signal: 3.5 V stimulation in 10 second bursts, 1 burst every 30 seconds at frequency 50 Hz. Duration 5 minutes.

IGF-1: 3 mv with electric frequency of 22 Hz, and electric current of 1 mA for 15 minutes and 3 ma for 15 minutes. Duration 5 minutes.

Tropoelastin: 0.06 V with 50 Hz alternating electrical field and electric current of 1 ma for 15 minutes and 3 ma for 15 minutes. Duration 2 minutes.

RANKL/TNF Alpha nuclear factor-kappa B (NF-κB) ligand/TNF Alpha: 3 mV at 2/100 Hz alternating frequency with current of 3 mA followed by 15 Hz, 1 Gauss EM field, consisting of 5-millisecond bursts with 5-microsecond pulses followed by 200- μs pulse duration at 30 Hz and with current amplitude of 140 mA. (Optional use depending on application.)

eNOS: Alternating high-frequency (HF) and medium-frequency signals (MF): Symmetric, biphasic, trapezoid pulses, with 400-μs pulse duration and 1.5/1-s ramp-up/ramp-down duration, respectively. HF consisted of 75 Hz pulses with 6 second on-21 second off for 15 minutes. MF consisted of 45 Hz pulses with 5 second on-12 second off for 15 minutes. Followed by stimulation duration set as 20 minutes for both 1 Hz and 20 Hz stimulations. For 1 Hz stimulation, stimulation is applied for 9 seconds, followed by a 1 second silent period, a total of 1080 stimulations for 20 min. For 20 Hz stimulation, stimulation is applied for 2 seconds, followed by silent period for 28 seconds, a total of 1600 stimulations for 20 min. Duration 2 minutes.

Activin B: 6 mv at 150 HZ Monophasic square wave pulse 0.1 ms in duration current of 15 mA for 15 minutes. Duration 2 minutes.

EGF—10 V/cm, pulse-width 180 μs, 500 Hz. Duration 9 minutes.

An exemplary bioelectric signal sequence suggested for heart regeneration in humans split into six phases is as follows.

- Phase I—Prepare Scar ("soil prep"): 10 minutes
  - IGF-1 signal 3 minutes
  - PDGF signal 3 minutes
  - HGF signal 2 minutes
  - EGF signal 2 minutes
- Phase II—Grow New Blood Vessels ("lay irrigation system"): 5 minutes
  - VEGF signal—3 minutes
  - SDF-1 signal—1 minute
  - eNOS signal—1 minute
- Phase III—Recruit and Inject Stem Cells ("plant"): 15 minutes
  - SDF-1 signal—10 minutes
  - PDGF-1 signal 5 minutes
- Phase IV—Build Tissue ("grow"): 25 minutes
  - Stem Cell Proliferation Signal—5 minutes
  - Stem Cell Differentiation Signal—5 minutes
  - Follistatin Signal—5 minutes
  - Tropoelastin Signal—5 minutes
  - GDF-10-2 minutes
  - GDF-11-3 minutes Phase V—Post Tissue Growth Maintenance ("fertilize"): 30 minutes
- VEGF—3 minutes
- EGF—2 minutes
- eNOS—2 minutes
- HGF—5 minutes
- PDGF—3 minutes
- Tropoelastin—5 minutes
- Relaxin—5 minutes
- Follistatin—5 minutes Phase VI—Protect Against Enemies ("pesticides"): 10 minutes
- Activin A and B—5 minutes
- IGF-1-5 minutes Results of Electrical Stimulation (ES) of Cells In Vitro IL-1β: mRNA expression was up regulated from 16 up to more than 400 times when cells were treated with 10 to 20 V between 3 and 20 hours.

IL-6: mRNA expression was up regulated from 3 times—as soon as 15 minutes- to 10 times.

IL-8: mRNA expression was stimulated by 5 to 50 times.

HGF: mRNA expression was up regulated by more than 10 times.

TNFα: mRNA expression was up regulated by 9 to 24 times.

MMP9: mRNA expression was up regulated 9 to 23 times with 3 and 24 hours of ES, respectively.

CCL2: mRNA expression was up regulated 15 to 64 times.

CXCL5: mRNA expression up regulated thousands of times.

CXCL10: mRNA expression up regulated thousands of times.

A week after treatment, samples can be collected for morphometric evaluation by in-situ hybridization or RT-PCR.

FIGS. 6-20 are images of the corresponding signals with the name, voltage, and frequency of each signal written on each image. eNOS and differentiation signals were omitted due to of complexity or lack of frequency parameters. The signals are to be further defined in terms of current and frequency, not voltage and frequency as shown. The voltage delivered to the cells will be different for each tissue type, but with current all of the signals can be kept constant regardless of tissue type. The device should have a current driven signal (instead of voltage driven like most other devices).

Figure 6:
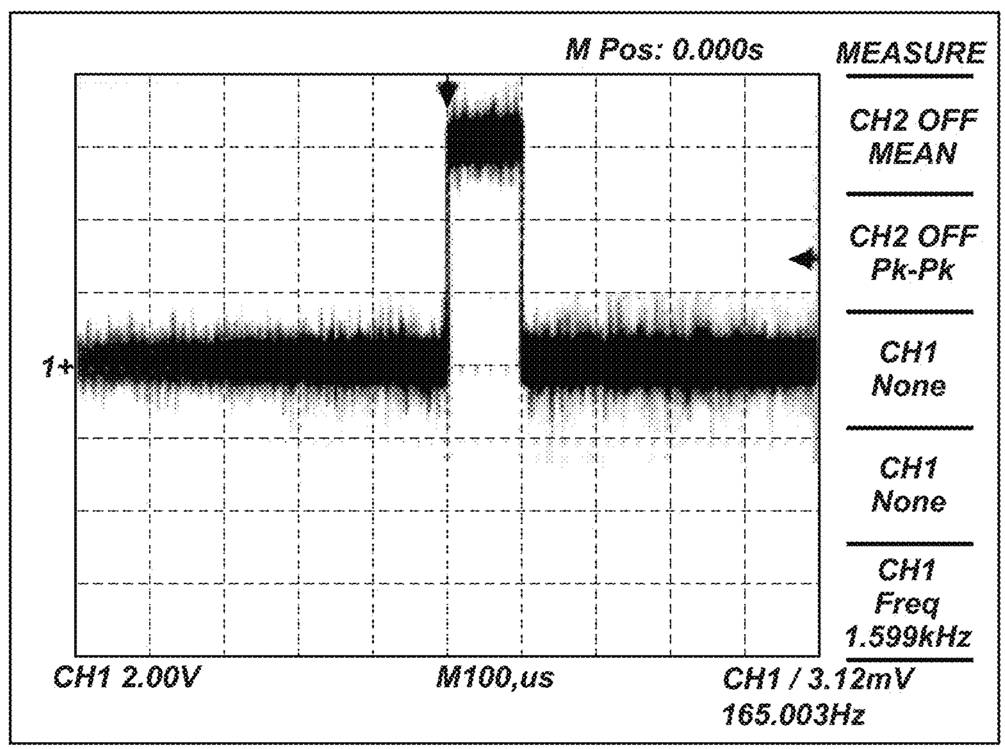
FIG. 6 depicts an image of the signal (voltage and frequency) associated with Activin B at 6.0 mV, pulse width 100 μs, square wave.
Figure 7:
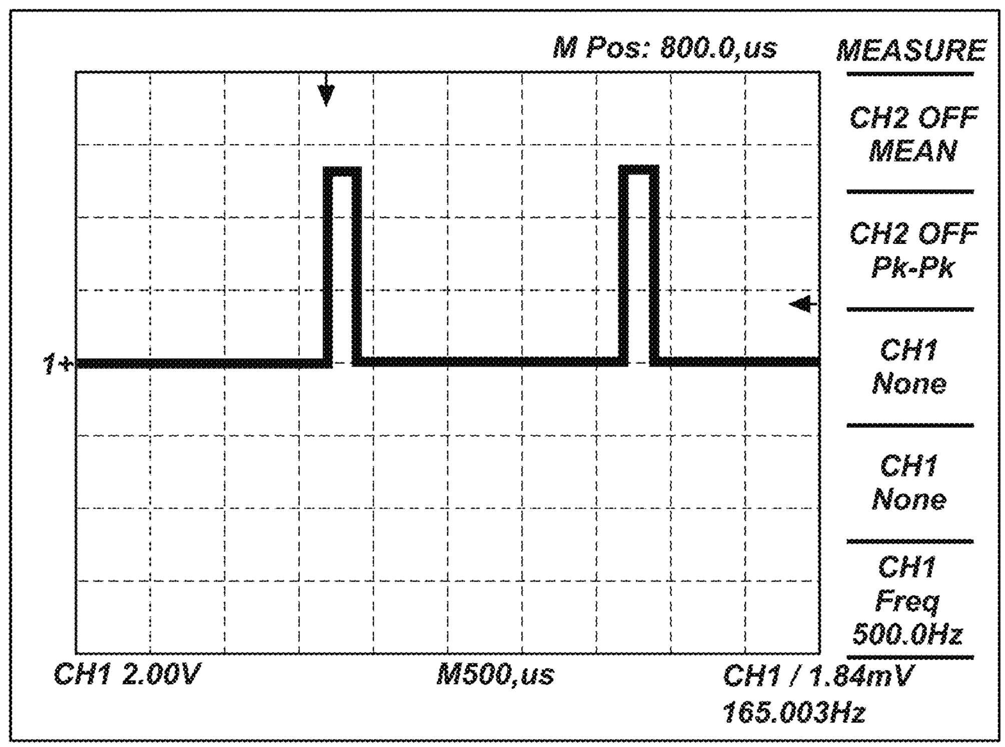
FIG. 7 depicts an image of the signal (voltage and frequency) associated with EGF at 10V/cm (5V here), 500 Hz, pulse width 180 μs, square wave.
Figure 8:
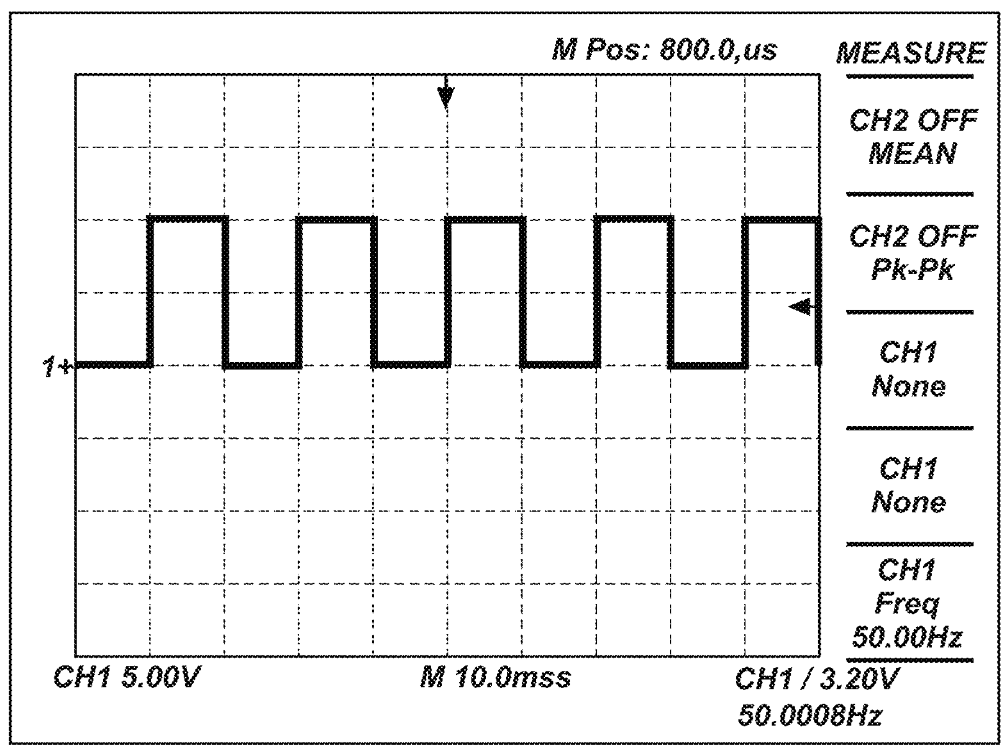
FIG. 8 depicts an image of the signal (voltage and frequency) associated with follistatin at 10V/cm, 50 Hz, square wave.
Figure 9:
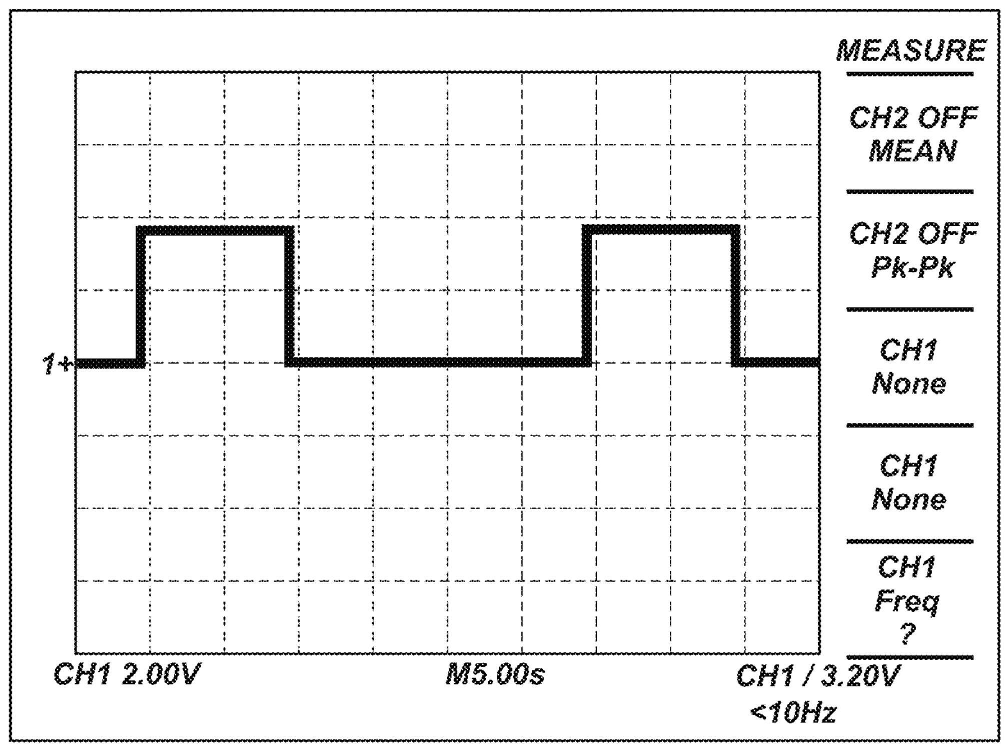
FIG. 9 depicts an image of the signal (voltage and frequency) associated with HGF at 3.5V, 10 second burst every 30 seconds, square wave.
Figure 10:
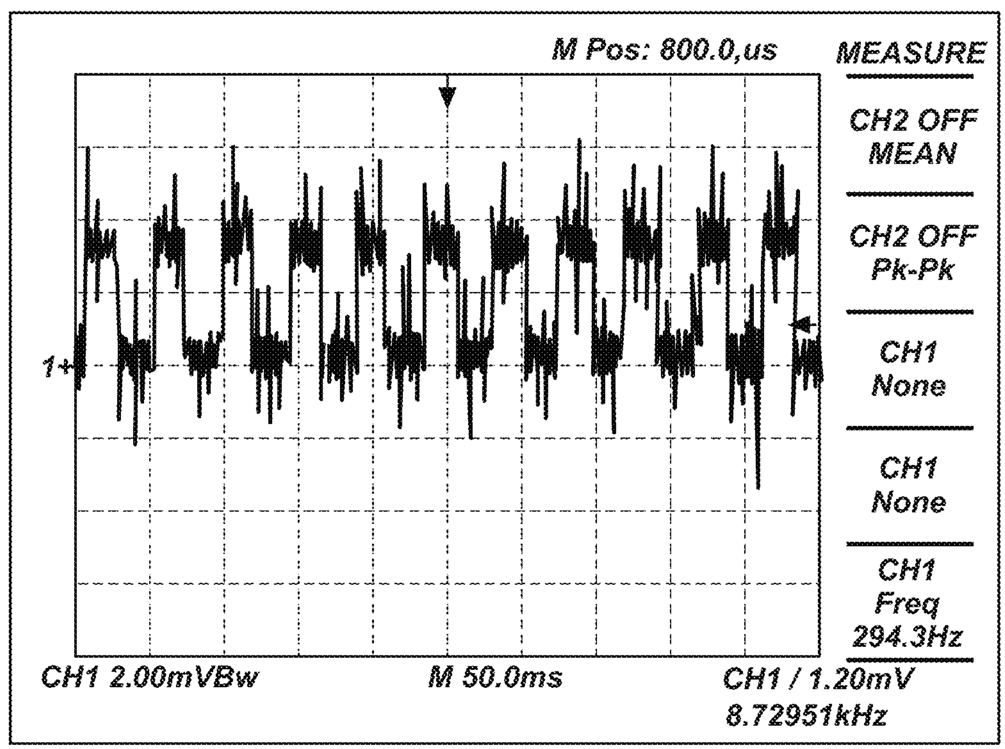
FIG. 10 depicts an image of the signal (voltage and frequency) associated with IGF-1: 3.0 mV, 22 Hz, square wave.
Figure 11:
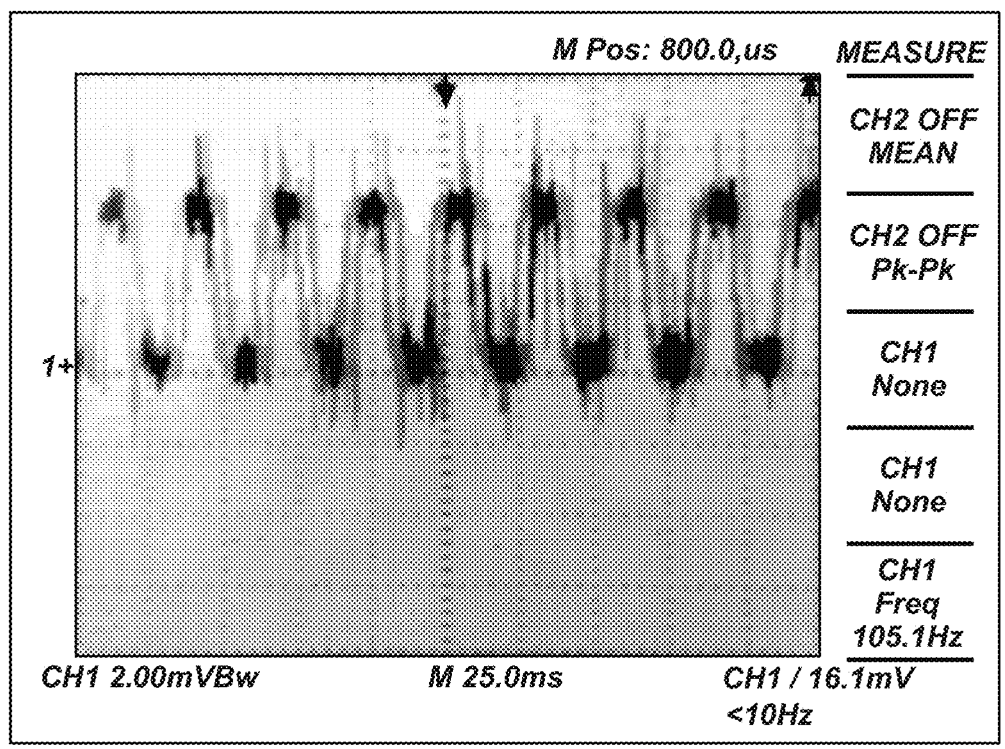
FIG. 11 depicts an image of the signal (voltage and frequency) associated with OPG: 4.0 mV, 2,000 Hz, square wave.
Figure 12:
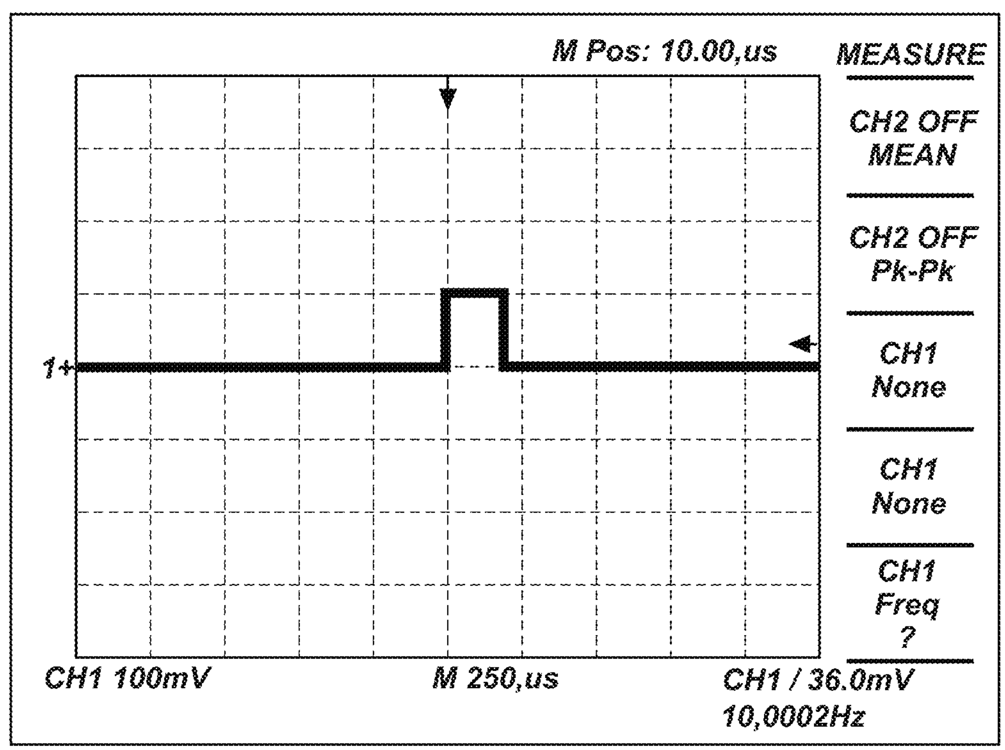
FIG. 12 depicts an image of the signal (voltage and frequency) associated with PDGF30%: 3V/cm (100 mV here), 10 Hz, pulse width 200 μs, square wave.
Figure 13:
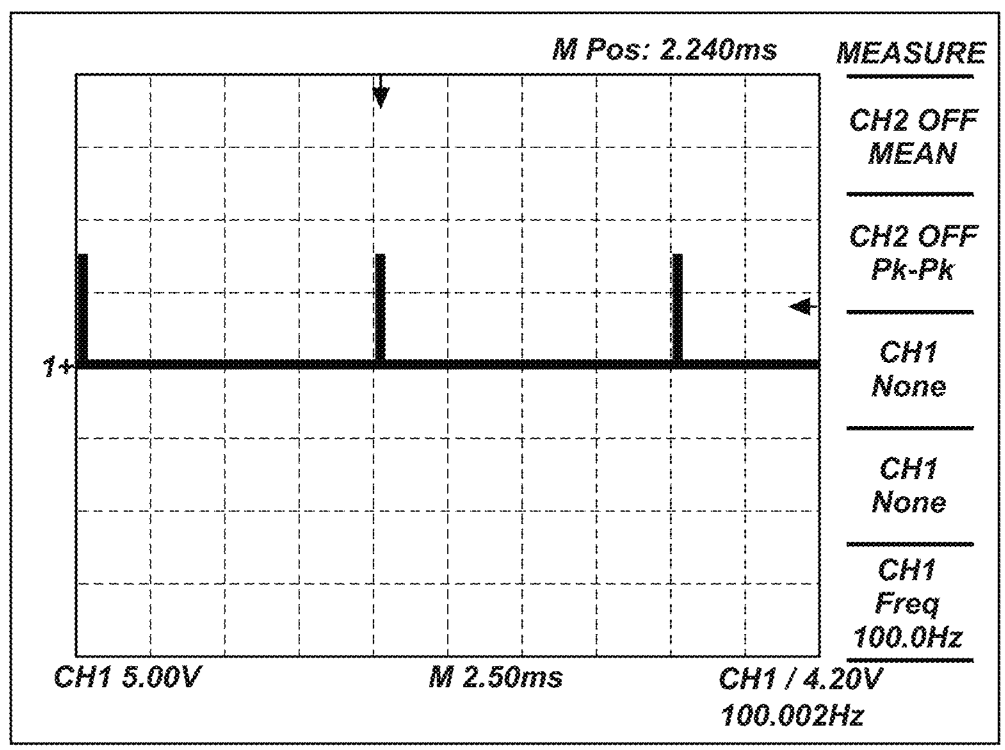
FIG. 13 depicts an image of the signal (voltage and frequency) associated with PDGF230%: 20V/cm (7.0V here), 100 Hz, pulse width 100 μs, square wave.
Figure 14:
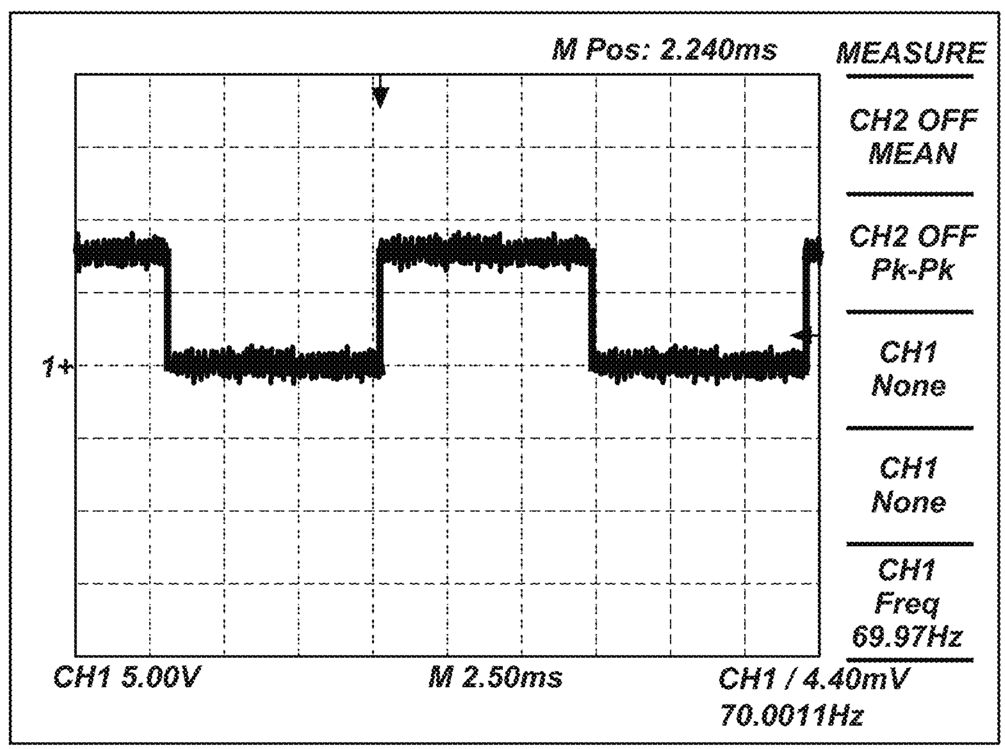
FIG. 14 depicts an image of the signal (voltage and frequency) associated with proliferation: 15 mV, 70 Hz, square wave.
Figure 15:
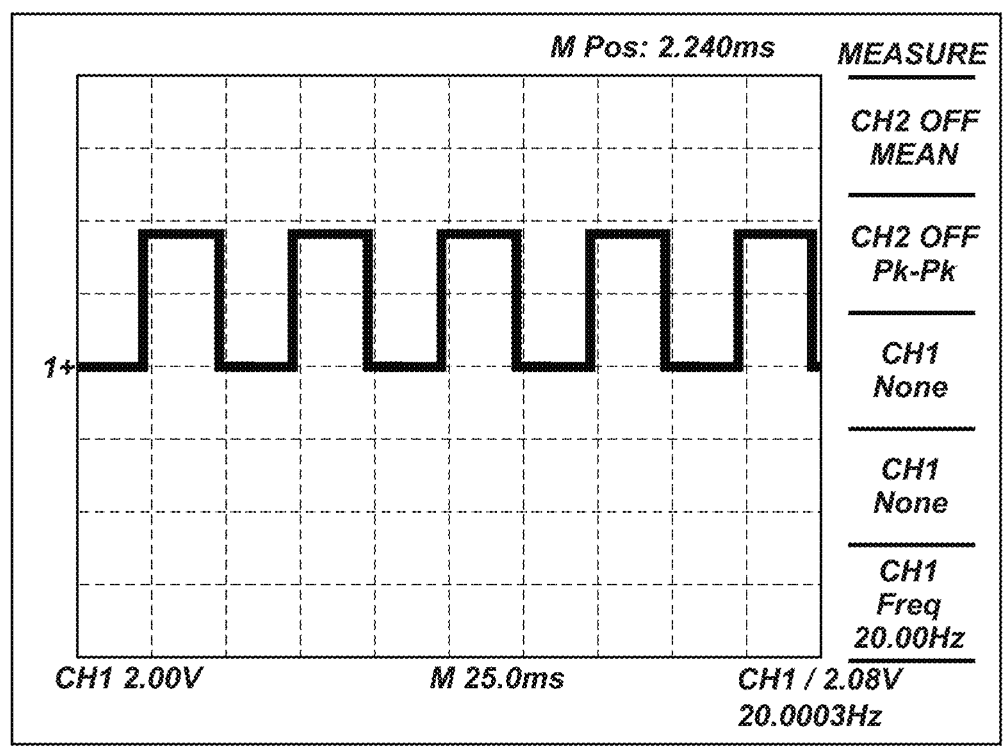
FIG. 15 depicts an image of the signal (voltage and frequency) associated with proliferation: 2.5-6.0 V (4V here), 20 Hz, pulse width 200-700 μs, square wave.
Figure 16:
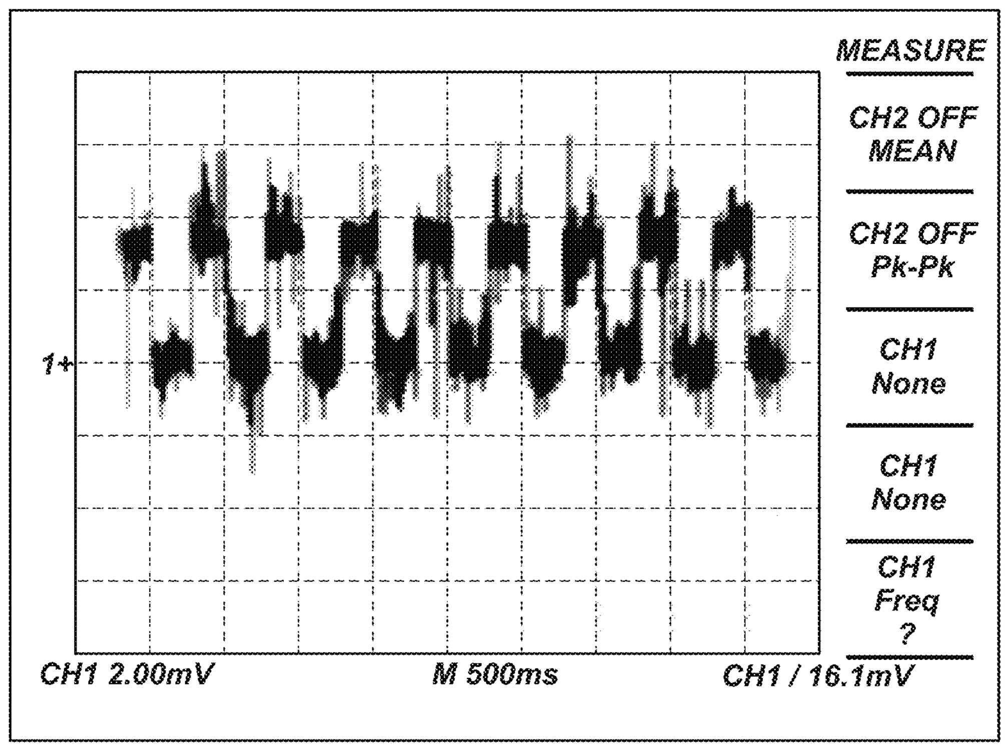
FIG. 16 depicts an image of the signal (voltage and frequency) associated with RANKL: 3.0 mV, 2 Hz, square wave.
Figure 17:
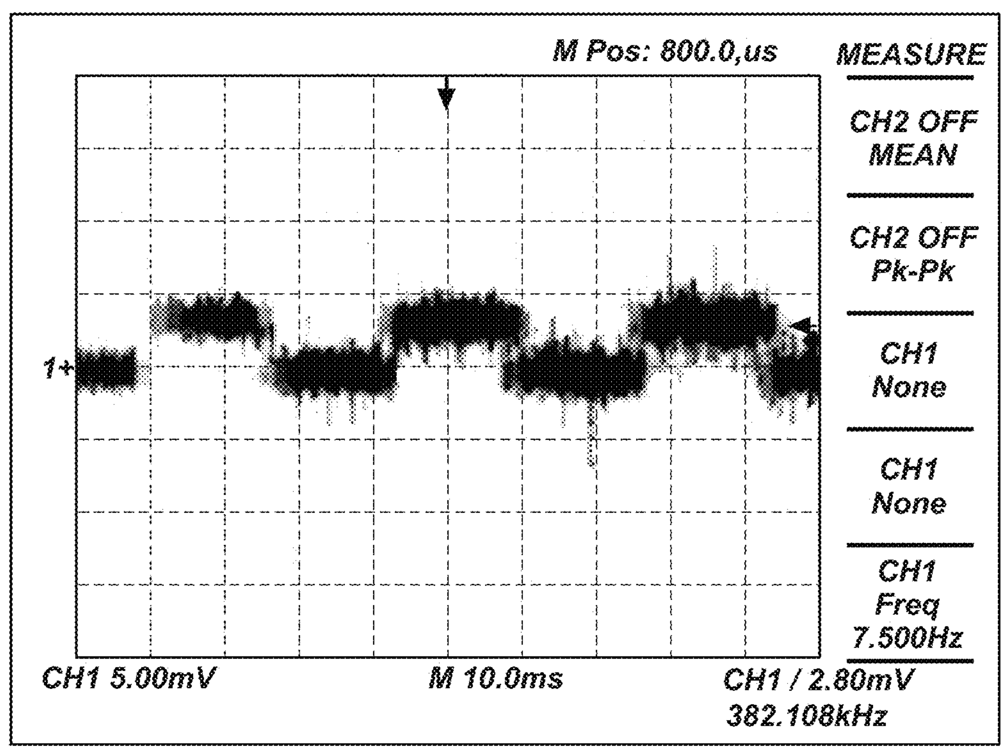
FIG. 17 depicts an image of the signal (voltage and frequency) associated with SDF-1: 3.5 mV, 30 Hz, square wave.
Figure 18:
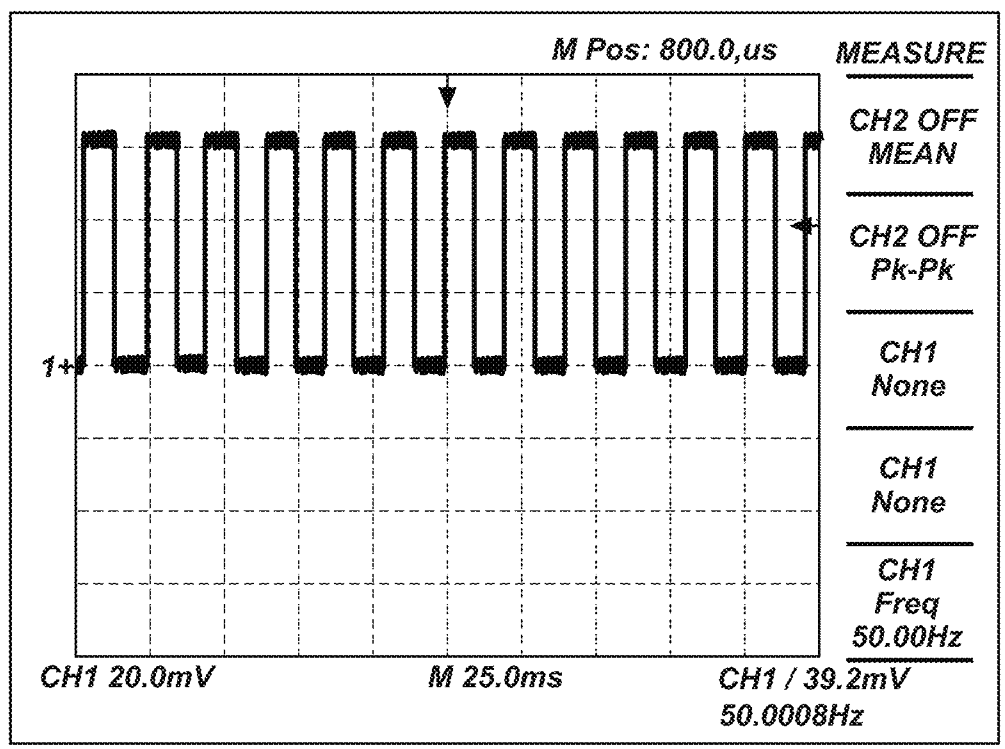
FIG. 18 depicts an image of the signal (voltage and frequency) associated with tropoelastin: 60 mV, 50 Hz, square wave.
Figure 19:
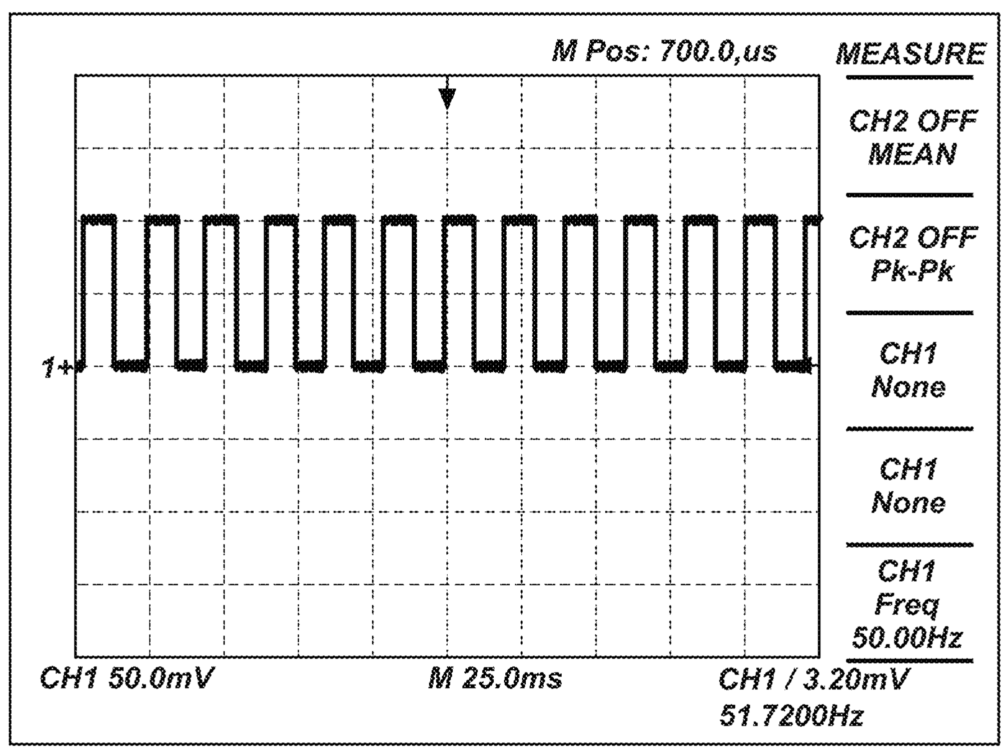
FIG. 19 depicts an image of the signal (voltage and frequency) associated with VEGF: 100 mV, 50 Hz, square wave.
Figure 20:
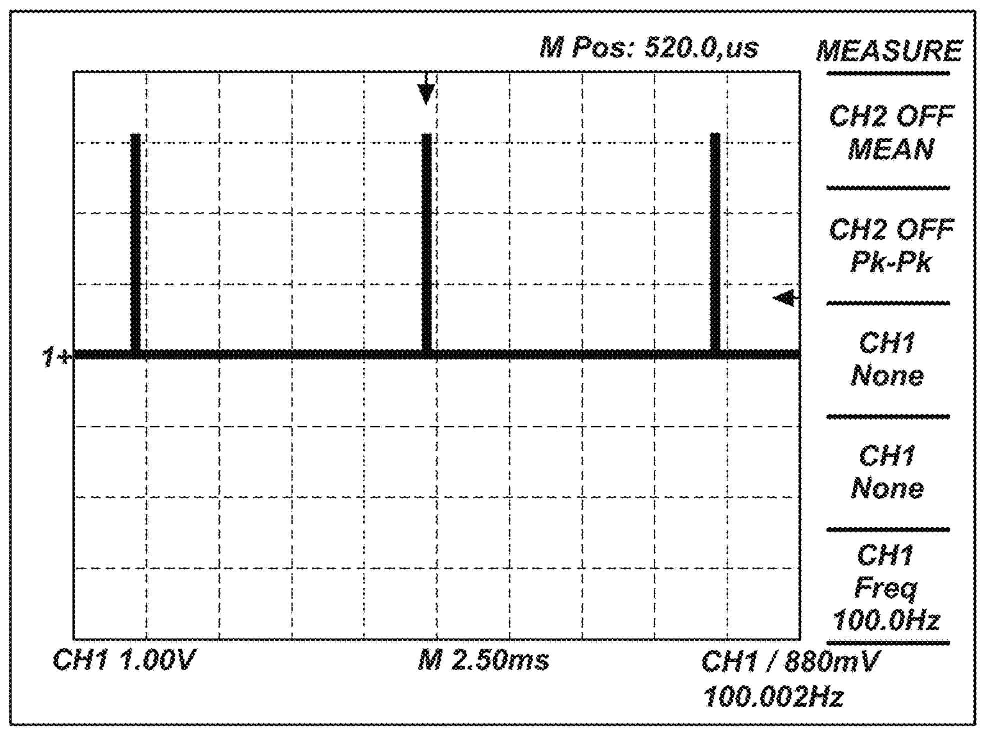
FIG. 20 depicts an image of the signal (voltage and frequency) associated with SDF-1 (2$^{nd}$ part): 0.25 mA (3.0V shown here), 100 Hz, 100 μs pulse width, square wave.

Specifically, FIG. 6 depicts an image of the signal (voltage and frequency) associated with Activin B at 6.0 mV, pulse width 100 μs, square wave on a TEKTRONIX® TPS 2024 four channel digital storage oscilloscope. FIG. 7 depicts an image of the signal (voltage and frequency) associated with EGF at 10V/cm (5V here), 500 Hz, pulse width 180 μs, square wave. FIG. 8 depicts an image of the signal (voltage and frequency) associated with follistatin at 10V/cm, 50 Hz, square wave. FIG. 9 depicts an image of the signal (voltage and frequency) associated with HGF at 3.5V, 10 second burst every 30 seconds, square wave. FIG. 10 depicts an image of the signal (voltage and frequency) associated with IGF-1: 3.0 mV, 22 Hz, square wave. FIG. 11 depicts an image of the signal (voltage and frequency) associated with OPG: 4.0 mV, 2,000 Hz, square wave. FIG. 12 depicts an image of the signal (voltage and frequency) associated with PDGF30%: 3V/cm (100 mV here), 10 Hz, pulse width 200 μs, square wave. FIG. 13 depicts an image of the signal (voltage and frequency) associated with PDGF230%: 20V/cm (7.0V here), 100 Hz, pulse width 100 μs, square wave. FIG. 14 depicts an image of the signal (voltage and frequency) associated with proliferation: 15 mV, 70 Hz, square wave. FIG. 15 depicts an image of the signal (voltage and frequency) associated with proliferation: 2.5-6.0 V (4V here), 20 Hz, pulse width 200-700 μs, square wave. FIG. 16 depicts an image of the signal (voltage and frequency) associated with RANKL: 3.0 mV, 2 Hz, square wave. FIG. 17 depicts an image of the signal (voltage and frequency) associated with SDF-1: 3.5 mV, 30 Hz, square wave. FIG. 18 depicts an image of the signal (voltage and frequency) associated with tropoelastin: 60 mV, 50 Hz, square wave. FIG. 19 depicts an image of the signal (voltage and frequency) associated with VEGF: 100 mV, 50 Hz, square wave. FIG. 20 depicts an image of the signal (voltage and frequency) associated with SDF-1 ($2^{nd}$ part): 0.25 mA (3.0V shown here), 100 Hz, 100 μs pulse width, square wave.

In certain embodiments, a subject's organ(s) and/or tissue(s) are first scanned or analyzed with a device to determine what his or her needs may be before treatment begins. The scanning/analysis can be by, e.g., generating mechanical vibrations at position adjacent the location to be an analyzed as described in, e.g., US 2003/0220556 A1 to Porat et al. (the contents of which are incorporated herein by this reference) and/or by measuring transmembrane voltage potential of a cell (see, e.g., Chernet & Levin, "Transmembrane voltage potential is an essential cellular parameter for the detection and control of tumor development in a *Xenopus* model," *Dis. Models & Mech.* 6, pp. 595-607 (2013); doi:10.1242/dmm.010835, the contents of which are also incorporated herein by this reference. See, also, Brooks et al. "Bioelectric impedance predicts total body water, blood pressure, and heart rate during hemodialysis in children and adolescents" J. Ren Nutr., 18(3):304-311 (May 2008); doi:10.1053/j.jrn.2007.11.008, the contents of which are incorporated herein by this reference, describing the use of bioelectric impedance to evaluate the variability of blood pressure, systolic blood pressure, etc.

As used herein, "scanning" means measuring bioelectrical electrical activity of organs, sometimes by placement of a bion coil reader and transmitter in the organ, and direct that information to a computer. The computer stores the bioelectrical read measurements of diseased organs and healthy organs and makes a comparative exam classifying the organ into one category or another, which is much like a doctor using information to make a diagnosis.

Presently, the best approach for whole body and individual organ scanning is to use a combination of: a. 3D Body Scannint, b. Quantum Magnetic Resonance Scanning, c. Biofeedback scanning, d. Bioelectric scanning, e. Bion implant scanning, f Nervous system scanning, and g. Light activated cell reaction reading.

Scanners such as the Ina'Chi scanner, the Quantum Magnetic Resonance Analyzer (QMRA), the 3D Quantum Health Analyzer Scan whole body organ health 2, Body-Scan® scanner, and the "BIONic muscle spindle" are also useful.

See, also, P. Collins "Bioelectric Signals Can Be Used to Detect Early Cancer," *Tufts News*, http://now.tufts.edu/news-releases/bioelectric-signals-used-detect-early-cancer (Feb. 1, 2013) reported that scientists had discovered a bioelectric signal that can identify cells likely to develop into tumors, and that they could lower the incidence of cancerous cells by manipulating the electrical charge across cell membranes. After the subject's needs in this regard are determined, then treatment (e.g., enhanced tissue growth or regeneration) may be initiated as needed and/or desired, preferably with the same device.

U.S. Pat. No. 9,032,964 to Schuler, the contents of which are incorporated herein by this reference, entitled "Method and system for processing cancer cell electrical signals for medical therapy" describes a scientific computer system with processor capable of recording, storing, and reprogramming the natural electrical signals of cancer cells as found in tumors of humans and animals. The reprogramming process is designed to create a confounding electrical signal for retransmission into a malignant tumor to damage or shutdown the cellular internal electrical communication system. Altering the electrical charge on the glycocalyx of the outer cell membrane is also part of the treatment by application of ions. The system causes cancer cell death as a medical treatment using ultra-low voltage and amperage encoded signals which are reprogrammed from cancer cell communication signals.

For example, the subject is positioned for analysis with a device, preferably with a non-invasive testing device for evaluating, e.g., the autonomic nervous system, organ function(s), and risk factors associated with heart disease, diabetes, and stroke. The non-invasive testing device may analyze data from, e.g., the subject's skin galvanic response, skin color, oximeter, blood pressure, and body composition analyzer to determine hardening and thickening of the subject's arteries, the subject's heart health, exercise capacity, thyroid function, neurotransmitter balance, and multiple other markers for health. See, also, Fatemi et al. "Imaging elastic properties of biological tissues by low-frequency harmonic vibration" *Proceedings of the IEEE,* 91(10):1503-1519 (October 2003).

In an alternative embodiment, the analysis conducted by the device comprises (or further includes) detecting minute energy fields around the human body with, e.g., a "SQUID magnetometer" (SQUID is an acronym for "Superconducting Quantum Interference Device"), able to detect biomagnetic fields associated with physiological activities in the subject's body. A quantum resonant magnetic analyzer analyzes such fields. The magnetic frequency and energy of a subject's organ(s) and/or tissue(s) are collected by appropriately positioning the sensor with respect to the portion of the subject's organ(s) and/or tissue(s) to be analyzed, and after amplification of the signal by the instrument, the data are compared with standard quantum resonant spectrum of diseases, nutrition, and other indicators/markers to determine whether the sample waveforms are irregular using a Fourier approach.

Treatment may include, e.g., moving magnets or changing magnetic fields (pulsed electromagnetic fields) about the tissue and/or organ, for example, to reduce inflammation or treat pain or induce tissue growth in the subject.

The subject's body is scanned to detect non-cancerous tissue damage. When non-cancer damage is detected, treatment may be initiated/indicated/scheduled.

The invention is further described with the aid of the following illustrative Examples.

EXAMPLES

Example—Controlling Expression of Follistatin

Low voltage pulsed electrical stimulation device for controlling expression of follistatin, a muscle formation promotion protein, from tissues.

Epicardial stimulation is especially useful for heart regeneration.

In one embodiment, the system stimulates the controlled production/release of follistatin, a known myostatin inhibitor, thus promoting the formation of new muscle and repair of damaged or weakened muscle including heart muscle post heart attack. Follistatin-like 1 (FSTL1) is a protein that encourages the growth of healthy cells, contractile muscle tissue and even blood vessels, helping supply the newly created muscle tissue with oxygen and nutrients. This therapy was originally designed to reduce or eliminate scarring of the heart following a heart attack and reversing heart failure, but may also be applicable to treating other organs suffering from muscle loss or degradation.

The electrical stimulation device promotes the reliable controlled release of follistatin with practical, safe, low voltages. The version of the system described in this Example includes the following components: Micro voltage signal generator (micro-stimulator from QIG Greatbatch); pacing and infusion lead; corkscrew tip; conductive polymer bandage wrap or patch; signal programmer; and external battery charging wand.

Relationship Between the Components:

The micro voltage signal generator is attached to the pacing infusion lead with, e.g., a corkscrew tip or conductive polymer bandage or patch to the tissue or organ to be treated. An external signal programmer may be used to program the micro voltage signal generator with the proper signals for treatment including the follistatin producing signal. The device battery may be re-chargeable with an external battery charging wand.

In use, the signal generator sends a signal to the target tissue organ that causes the genes within the DNA of that tissue to start the follistatin synthesis process on demand. The signal generator sends a signal to the target tissue organ that causes the genes within the DNA of that tissue to start releasing follistatin on demand. The follistatin—(muscle growth) production signal is preferably 10V at 50 Hz and 100 Hz 0.25 mA alternating back and forth. A 3V signal is being developed.

The system not only controls the DNA to build ribosomes and proteins, but also controls the gates of the cell membranes opening and closing correctly to promote regeneration.

The essential elements are the micro voltage signal generator and the means for delivering the signal to the target tissue.

A micro infusion pump is included to the system for delivering other supportive substances or even follistatin in greater volume more quickly.

The signal generator may be external or internal. The transmission of the signal may be wireless, via liquid and/or via wires.

The tissue contact interface may be a patch or bandage or may be via electrodes or leads.

The described system produces follistatin under precise dosing control at safe and comfortable low voltages.

The signal generator programmed with the follistatin release signal is directed via a lead, bandage of patch to the target organ tissue in need of muscle repair or build up. As the signal is in stimulation mode the tissue releases follistatin and muscle is built or repaired as needed until full function resumes or the desired enhanced function is reached.

Example—Treatment of the Pancreas with Bioelectric Controlled Protein

Treatment of the pancreas with bioelectric controlled protein expression and micro infusion pump stem cell composition delivery.

A pancreas regeneration system includes three primary components. First, the micro bioelectric regeneration stimulator (micro-stimulator from QIG Greatbatch) that controls release of 10 regeneration promoting proteins including SDF-1 a stem cell homing signal, IGF-1, HGF, EGF, activin A and B, eNOS, VEGF, follistatin and tropoelastin. Second, a programmable, re-fillable micro infusion pump. Third, a fifteen component stem cell-based regeneration composition comprising a variety of cell types, growth factors, BMP-7, PDLI-1, HGH, selected alkaloids, micro RNAs, nutrient hydrogel, NADA and pancreatic matrix.

In use, the stimulator and pump are implanted just below the subject's skin with a re-fillable silicone septum port with pacing infusion lead directed to the pancreas with a total conductive infusion wrap tip that is gentle on the pancreatic tissue. One portion of the pacing infusion lead is directed to the interior portion of the pancreas.

Example—a Device for Decalcifying and Regenerating a Heart Valve or Valves so a Patient May Keep their Own Valve(s) Rather than Receiving an Implant The device combines three methods of decalcification. The system regenerates heart valve tissue. Shape reform is combined via a nitinol ring with decalcification and regeneration.

Heart valves become dysfunctional from calcification build up, and clots form, which causes strokes, heart valves lose shape and thus function. Heart valve leaflets degenerate and do not function properly.

Other devices failed to completely de-calcify heart valve and left dangerous deposits. They failed to even attempt to regenerate heart valve tissues. They failed to combine shape reform with decalcification and regeneration.

The described system has three methods of decalcification combined. Described are a device and method combining shape reform via a nitinol ring with decalcification and regeneration.

As stated above, heart valves become dysfunctional from calcification build up, clots form which causes strokes, heart valves lose shape and thus function. Heart valve leaflets degenerate and do not function properly.

The device decalcifies the heart valves, restores shape, and regenerates them restoring full normal function.

The disclosed system reduces calcification in a heart valve. It also regenerates the heart valve with stem cell recruitment and differentiation supported by a full range of regeneration promotion proteins. The system may be combined with a non-surgical reforming option when required or thought desirable.

The disclosed system combines three methods of decalcification, which leads to heart valve tissue regeneration. The system combines shape reform via a nitinol ring with decalcification and regeneration.

Also, it can produce heart valve decalcification system, a heart valve regeneration system, a heart valve shape reform system, a heart varve autologous cell created leaflets, and a heart valve catheter based delivery system.

The version of the system discussed for this Example includes the following components: Abrasive surface burr on tip of catheter for decalcification; Ultrasonic cleaning on tip of catheter; Biological safe solvent cleaner delivery system on tip of catheter; Bioelectric signal delivery array on tip of catheter; Bioelectric SDF•1 stem cell homing signal; Bioelectric IGF-1 DNA repair signal; Bioelectric HGF regeneration signal; Bioelectric EGF regeneration signal; Bioelectric Activin A and B regeneration signals; Bioelectric follistatin regeneration signal; Bioelectric Tropoelastin elasticity regeneration signal; Bioelectric eNOS blood flow signal; Bioelectric VEGF blood flow signal; Bioelectric stem cell proliferation signal; Bioelectric stem cell differentiation control signal; Nitinol ring placement catheter for shape reform; Autologous cell-created heart valve leaflets; Autologous cell-created heart valve placement device; Optical viewing catheter; Cerebral protection device to stop debris from reaching brain; Bioelectric stimulator signal generator; Micro Infusion pump; Suction cup system for holding heart valve leaflet; and Suction system to vacuum away debris.

Relationship Between the Components:

The abrasive surface burr on tip of catheter for decalcification, ultrasonic cleaning on tip of catheter, and biological safe solvent cleaner delivery system on tip of catheter in sequence work to fully decalcify clean the heart valve leaflets and orifice. The optical viewing system/catheter provides visualization of areas being cleaned. The suction cup system helps hold the heart valve leaflets during cleaning. The suction vacuum helps remove debris. The optical viewing system/catheter provides cerebral protection with a filter or deflector or the bioelectric signal delivery array on tip of catheter, bioelectric SDF•1 stem cell homing signal, bioelectric IGF-1 DNA repair signal, bioelectric HGF regeneration signal, bioelectric EGF regeneration signal, bioelectric Activin A and B regeneration signals, bioelectric follistatin regeneration signal, bioelectric Tropoelastin elasticity regeneration signal, bioelectric eNOS blood flow signal, bioelectric VEGF blood flow signal, and bioelectric stem cell proliferation signal bioelectric regeneration signals powered by the bioelectric signal generator, which is external work to regenerate the native heart valve by recruiting stem cells and building new healthy tissues. The nitinol ring is placed by a catheter delivery system only if the above decalcification and regeneration procedure has not restored full function. The autologous cell created heart valve leaflets are only placed via the heart valve catheter-based delivery system if all the previous steps have not restored full function.

The three decalcification catheters; abrasive burr, ultrasonic cleaning and biological safe solvent under high pressure clean the heart valve. The ten bioelectric regeneration signals regenerate the heart valve. The nitinol ring restores original shape and thus improves function. The autologous cell created heart valve leaflets are placed only if all the decalcification, regeneration, and shape reform steps have failed to restore full normal function. If all of the above has failed a micro infusion pump may be connected to the guiding catheter and a fifteen component regeneration cocktail composition may be infused until function is restored.

If the three decalcification steps and 10 and regeneration signals do not restore full heart valve function, then a nitinol ring is placed by catheter in the heart valve orifice to attempt to restore shape and function. If the decalcification, regeneration, and nitinol ring shape reform procedures do not work to restore full function then an autologous cell created heart valve is placed via a catheter delivery system The three cleaning devices are delivered via a deflecting tip guiding catheter to their position. An optical viewing catheter provides visualization. A suction cup holds leaflets. A dental burr is used on tip of deflecting catheter for first cleaning. An ultrasonic cleaner second cleaning. A biological safe solvent high pressure sprayer for third cleaning. The cleaning is followed by regeneration utilizing bioelectric signals delivered via an array on the tip of a catheter that control more than 10 protein expressions. If needed a nitinol ring is placed via a catheter to reform shape. If needed a new set of autologous cell created heart valve leaflets are placed via catheter.

The heart valve function may be restored with cleaning only. The regeneration procedure may be used after autologous cell-created implant to improve strength and function. The microinfusion pump could replace or supplement the regeneration stimulator.

The three decalcification procedures are completed first under optical guidance. A cerebral protection device is essential. This is followed by the delivery of ten regeneration signals via the bioelectric signal array at the tip of the catheter. If full normal function is not restored at this point, a nitinol ring may be placed to help reform normal shape. If full function is still not restored after all these steps, autologous cell created heart valve leaflets may be placed via catheter.

The nitinol ring and new heart valve leaflets are only necessary if the decalcification and regeneration procedure failed to restore full normal function. The micro infusion pump is optional.

In an alternative embodiment, a robot could control the full procedure of cleaning, regeneration, nitinol ring placement and percutaneous autologous cell created valve placement.

Example—Hair Growth Stimulation I

A "brain cap" is connected to the stimulator and pump and treatment is 40 minutes, 3 times a week for 8 to 36 weeks as needed.

A method and apparatus for producing hair growth stimulation using bioelectrical energy, topical composition(s), stem cell/growth factor micro infusions, and combinations thereof.

By using bioelectric signaling resulting from specific protein expressions and their cellular responses to exposure to specific micro voltages. The device controls release of SDF-1 a stem cell homing factor as well as IGF-1, HGF, EGF, follistatin, Tropoelastin, eNOS, and VEGF as well as micro infusion delivery of an, e.g., 15 component hair regeneration cocktail which includes nutrient hydrogel, thus providing all the supporting elements to grow a full head of hair. The composition preferably includes at least EGF and HGF.

Low doses on shaven arms and legs are being tested before moving to higher doses on the head. Safety or the bioelectric stimulation signals in sheep has been studied. The bioelectric stimulation delivery (micro-stimulator from QIG Greatbatch) is combined with a 14 electrode helmet and a hair matrix ointment to ensure the bald areas of the head have the "hair protein" signals so when the SDF-1 bioelectric signal recruits stem cells to the balding areas, those stem cells get the "create hair" signal not the "create skin" signal.

What follows is the signal sequence for the hair regeneration. Note—These are the signals to be reached 3 mm deep in the tissues, not the originating signal. The resistance from the driving signal stimulator to the target tissue needs to be calculated to determine the originating signal in order to reach the below target signals 10 mm to 3 cm deep within the target tissues.

40 minute treatment cycles twice a week for 4 weeks and then 3 times a week for 12 weeks.

1. VEGF—Blood vessel sprouting growth=0.1V applied at a frequency of 50 Hz (duration 3 minutes).
2. SDF-1—Stem cell recruiting signal=30 pulses per second with a voltage of 3.5 mV, and successively alternating currents of 700 to 1500 picoamps for one minute, and again with 700 to 1500 picoamps for one minute and stimulated with current of 0.25 mA, pulse duration of 40 pulses/s, pulse width of 100 μs, and frequency of 100 Hz—each signal for 40 minutes to 8 hours a day for 2 to 36 months as needed for ideal results (duration 7 minutes.)
3. Stem cell proliferation signals: 15 mV and a current of 500 picoamps at 70 pulses per minute for 3 hours and 20 pulses per minute, a pulse amplitude of from 2.5-6 volts, and a pulse width of from 0.2-0.7 milliseconds for 3 hours (duration 3 minutes).
4. Stem cell differentiation signals to become muscle: 200 picoamps for 10 seconds for 1 hour and the pulse has an amplitude of 5 volts and a width of 0.5 milliseconds for 1 hour (duration 1 minute.)
5. Follistatin—(muscle growth) production signal: 10V at 50 Hz and 100 Hz for 12 hours each (duration 1 minute.)
6. HGF: Hepatocyte growth factor (arrhythmia reduction) signal: 3.5V stimulation in 10 second bursts, 1 burst every 30 seconds at frequency 50 Hz (duration 5 minutes.)
7. IGF-1: 3 mv with electric frequency of 22 Hz, and electric current of 1 mAfor 15 minutes and 3 ma for 15 minutes (duration 5 minutes.)
8. Tropoelastin: 0.06 V with 50 Hz alternating electrical field and electric current of 1 ma for 15 minutes and 3 ma for 15 minutes (duration 2 minutes.)
9. eNOS: Alternating high-frequency (HF) and medium-frequency signals (MF): Symmetric, biphasic, trapezoid pulses, with 400-μs pulse duration and 1.5/1-s ramp-up/ramp-down duration, respectively. HF consisted of 75 Hz pulses with 6 second(s) on-21 second(s) off for 15 minutes. MF consisted of 45 Hz pulses with 5 second(s) on-12 second(s) off for 15 minutes. Followed by stimulation duration set as 20 minutes for both 1 Hz and 20 Hz stimulations. For 1 Hz stimulation, stimulation is applied for 9 seconds, followed by a 1 second silent period, a total of 1080 stimulations for 20 minutes For 20 Hz stimulation, stimulation is applied for 2 seconds, followed by silent period for 28 seconds, a total of 1600 stimulations for 20 minutes (duration 2 minutes.)
10. Activin B: 6 mv at 150 HZ Monophasic square wave pulse 0.1 ms in duration current of 15 mA for 15 minutes (duration 2 minutes.)
11. EGF: 10 V/cm, pulse-width 180 μs, 500 Hz (duration 9 minutes.)

Drop down resistors may be used in the pacing infusion lead line to adjust down voltages when necessary.

Hair Growth

In a method of stimulating hair growth, the method includes: exposing a hair growth structure to a source of narrow band of bioelectric signals without having applied a drug, cosmeceutical, and/or chromophore to the hair growth structure; and applying a bioelectrical signal controlled protein to promote hair growth by maintaining the exposure of the hair growth structure to the source of narrowband of bioelectric signals for protein expression for a clinically effective duration and at a clinically effective depth to stimulate hair growth without causing skin ablation.

The source of narrowband bioelectric signals may be delivered by, e.g., wireless transmission, electro-acupuncture needles, conductive patches doped with hair growth promoting drugs and proteins, a conduction signal helmet or cap, a metal hair scalp tickler or any combination thereof.

The bioelectric signal may produce vascular endothelial growth for factor release VEGF—to promote hair growth and blood vessel sprouting growth 0.1 V applied at a frequency of 50 Hz.

The method bioelectric signal may produce SDF-1-Stem cell recruiting signal: 30 pulses per second with a voltage of 3.5 mV and successively alternating currents of 700 to 1500 picoamps for one minute, and again with 700 to 1500 picoamps for one minute and stimulated with current of 0.25 mA pulse duration of 40 pulses/s, pulse width of 100 pS, and frequency of 100 Hz.

The bioelectrical signal may produce a stem cell proliferation signal: 15 mV and a current of 500 picoamps at 70 pulses per minute for three (3) hours and 20 pulses per minute, a pulse amplitude of from 2.5-6 volts, and a pulse width of from 0.2-0.7 milliseconds for 3 hours.

The bioelectric signal may produce stem cell differentiation signals—200 picoamps for 10 seconds for 1 hour and the pulse has an amplitude of 5 volts and a width of 0.5 milliseconds for 1 hour.

The bioelectric signal may produce Follistatin (muscle growth) production signal: 10 V at 50 Hz and 100 Hz for 12 hours each.

The method bioelectric signal may produce HGF~Hepatocyte growth factor (arrhythmia reduction) signal: 3.5V stimulation in 10 second bursts, 1 burst every 30 seconds at frequency 50 Hz.

The bioelectric signal may also produce IGF-1: 3 mv with electric frequency of 22 Hz, and electric current of 1 mA for 15 minutes and 3 mA for 15 minutes.

The method bioelectric signal may also produce Tropoelastin: 0.06V with 50 Hz alternating electrical field and electric current of 1 ma for 15 minutes and 3 mA for 15 minutes.

The method bioelectric signal may also produce RANKL nuclear factor kappa B (NF-KB) ligand: 3 mV at: 2/100 Hz alternating frequency with current of 3 ma followed by 15 Hz, 1 Gauss EM field, consisting of 5-mlllisecond bursts with 5-microsecond pulses followed by 200 μs pulse duration at 30 Hz and with current amplitude of 140 mA.

The bioelectric signal may also produce eNOS. Alternating high frequency (HF) and medium-frequency signals (MF): Symmetric; biphasic, trapezoid pulses, with 400 μs pulse duration and $1.5/1^{-S}$ ramp-up/ramp-down duration, respectively. HF consisted of 75 Hz pulses with 6 seconds on and 21 seconds off for 15 minutes. MF consisted of 45 Hz pulses with 5 seconds on and 12 second off for 15 minutes. Followed by stimulation duration set as 20 minutes for both 1 Hz and 20 Hz stimulations. For 1 Hz stimulation, stimulation is applied.

Example—Hair Growth Stimulation II

Described is a method for stimulating hair growth, the method comprising: exposing a hair growth structure to a source of narrow band of bioelectric signals, without having applied a drug, cosmeceutical, and/or chromophore to the hair growth structure; together with bioelectrical signal controlled protein release to promote hair growth by maintaining the exposure of the hair growth structure to the source of narrowband of bioelectric signals for protein expression for a clinically effective duration and at a clinically effective depth to stimulate hair growth without causing skin ablation.

In such a method, the source of narrowband bioelectric signals may be delivered by, for example, wireless transmission, electro-acupuncture needles, conductive patches doped with hair growth promoting drugs and proteins, a conduction signal helmet or cap, a metal hair scalp tickler, or any combination thereof.

In such a method, the bioelectric signal may be used to produce vascular endothelial growth for factor release VEGF—to promote hair growth and blood vessel sprouting growth 0.1V applied at a frequency of 50 Hz.

In such a method, the bioelectric signal may be used to produce SDF-1: Stem cell recruiting signal: 30 pulses per second with a voltage of 3.5 mV, and successively alternating currents of 700 to 1500 picoamps for one minute, and again with 700 to 1500 picoamps for one minute and stimulated with current of 0.25 mA, pulse duration of 40 pulses/s, pulse width of 100 μs, and frequency of 100 Hz.

In such a method, the bioelectric signal may be used to produce a stem cell proliferation signal: 15 mV and a current of 500 picoamps at 70 pulses per minute for 3 hours and 20 pulses per minute, a pulse amplitude of from 2.5-6 volts, and a pulse width of from 0.2-0.7 milliseconds for 3 hours.

In such a method, the bioelectric signal may be used to produce—stem cell differentiation signals: 200 picoamps for 10 seconds for 1 hour and the pulse has an amplitude of 5 volts and a width of 0.5 milliseconds for 1 hour.

In such a method, the bioelectric signal may be used to produce Follistatin—(muscle growth) production signal: 10 V at 50 Hz and 100 Hz for 12 hours each.

In such a method, the bioelectric signal may be used to produce HGF—Hepatocyte growth factor (arrhythmia reduction) signal: 3.5V stimulation in 10 second bursts, 1 burst every 30 seconds at frequency 50 HZ In such a method, the bioelectric signal may be used to produce IGF-1: 3 mv with electric frequency of 22 Hz, and electric current of 1 mA for 15 minutes and 3 ma for 15 minutes.

In such a method, the bioelectric signal may be used to produce Tropoelastin: 0.06V with 50 HZ alternating electrical field and electric current of 1 ma for 15 minutes and 3 ma for 15 minutes.

In such a method, the bioelectric signal may be used to produce RANKL nuclear factor-kappa B (NF-KB) ligand: 3 MV at 2/100 Hz alternating frequency with current of 3 mA followed by 15 Hz, 1 Gauss EM field, consisting of 5-millisecond bursts with 5-microsecond pulses followed by 200 μs pulse duration at 30 Hz and with current amplitude of 140 mA.

In such a method, the bioelectric signal may be used to produce eNOS: Alternating high-frequency (HF) and medium-frequency signals (MF): Symmetric, biphasic, trapezoid pulses, with 400 μs pulse duration and 1.5/1-s ramp-up/ramp-down duration, respectively. HF consisted of 75 Hz pulses with 6 second on and 21 second off for 15 minutes. MF consisted of 45 Hz pulses with 5 second on and 12 second off for 15 minutes. Followed by stimulation duration set as 20 minutes for both 1 Hz and 20 Hz stimulations. For 1 Hz stimulation, stimulation is applied for 9 seconds, followed by a 1 second silent period, a total of 1080 stimulations for 20 min. For 20 Hz stimulation, stimulation is applied for 2 seconds, followed by silent period for 28 seconds, a total of 1600 stimulations for 20 min.

In such a method, the bioelectric signal may be used to produce Activin A: 6 mv at 150 HZ Monophasic square wave pulse 0.1 ms in duration current of 15 mA for 15 minutes.

In such a method, the sequence order is preferably VEGF, eNOS, SDF-1, Proliferation, VEGF, eNOS, HGF, IGF-1, Follistatin, Differentiation, Tropoelastin, Follistatin, IGF-1, HGF, SDF-1 and may be repeated.

In such a method, the bioelectric signal may be used to control expression of FGF and/or EGF.

For this Example, the system optimally includes the following components: Brain Electroacupuncture Cap; Micro regeneration stimulator and connecting leads; Micro infusion pump; Bioelectric signal program SDF-1=Stem Cell Homing Factor; Bioelectric signal program IGF-1; Bioelectric signal program HGF; Bioelectric signal program EGF; Bioelectric signal program Follistatin; Bioelectric signal program Tropoelastin; Bioelectric signal program eNOS; Bioelectric signal program VEGF; Bioelectric signal program Activin A and B; Hair regeneration cocktail 15 component composition; Bioelectric signal for cell proliferation; and Bioelectric signal to control differentiation.

The brain electroacupuncture cap is placed onto the head of the patient. The micro regeneration stimulator and connecting leads are connected to the brain electroacupuncture cap. The micro infusion pump is connected to the brain electroacupuncture cap. The Micro stimulator runs through a program releasing, e.g., 10 specific proteins for specific purposes all of which work together for hair regeneration. In severe cases of hair loss, a micro pump is filled with the HC-15 fifteen component hair regeneration cocktail comprising three types of stem cells, growth factors, nutrient hydrogel, scalp matrix, and Micro RNAS as well as known topical solutions for hair regeneration (e.g., minoxidil).

The micro hair regeneration stimulator may be used as a standalone. Results are accelerated and enhanced with the addition of the micro infusion pump that is re-filled daily, weekly or monthly.

The brain electroacupuncture cap may be adapted from EEG monitoring caps and electro acupuncture needles. The micro stimulator is obtained from an OEM supplier of heart pacemakers. The software is programmed into the stimulator with a standard programmer. The micro pump is obtained from an OEM supplier that makes pumps for drug infusion.

For this Example, the micro regeneration stimulator is essential. For this Example, the brain electroacupuncture cap is optional. One can use tape electrodes or standard electro acupuncture needles instead or the signals can be transmitted by a wireless light like device.

The micro infusion pump is optional for severe cases or for accelerating results.

The brain electroacupuncture cap is connected to the stimulator and pump and treatment is 40 minutes three times a week for 8 to 36 weeks as needed.

Example—Brain and Organ Regeneration Device Based on Bioelectric IGF-1 Stimulation An organ regeneration device that produces controlled release of platelet-derived growth factor by bioelectric stimulation is disclosed. The system provides controlled sustained and repeated release of PDGF via a wire conduction lead or wireless signal delivery and may be combined with a micro infusion pump for maximum results in severe organ failure cases.

A Brain and Organ Regeneration Device based on Bioelectric IGF-1 Stimulation is disclosed. The system directs a lead to exactly the right position with the target organ and stimulates controlled expression of IGF-1 in combination with SDF-1, VEGF, HGH, HGF, Follistatin and tropoelastin in the proper sequence to optimize repair and regeneration.

Damaged aged or cancer stricken organs and tissues are unable to be regenerated back to their original health with current available therapies.

Injections wash away and needle pricks are painful and the entry site is too far away from the organ. Other electrical stimulation devices do not: produce the expression IGF-1 or other combination useful proteins in the most effective sequence.

The disclosed system directs a lead to exactly the right position with the target organ and stimulates controlled expression of IGF-1 in combination with SDF-1, VEGF, HGH, HGF, Follistatin, and tropoelastin in the proper sequence to optimize repair and regeneration.

IGF-1 can transport raw materials to the cells for repair and renovation. IGF-1 promotes raw material transport to the cells. Meanwhile, nucleic acids are helpful in repairing the damage in the DNA, while stimulating ceil division. IGF-1 is able to minimize the DNA and cell stellar damage, but also treat the DNA and the cell. The IGF repair cells and thus tissues and organs, especially when delivered over time in combination with other factors such as SDF-1, VEGF, HGH, HGF, follistatin, and tropoelastin.

Controlled on demand expression of IGF-1 can help repair cells, tissues and organs including brain, muscle, pancreas, lung, skin, kidney and liver.

IGF-1 injections and infusions do not get enough repair material to the target organ or tissue and cause inflammation, which is counterproductive to regeneration. Thus electrical stimulation is preferred. Prior art electrical stimulation systems failed to express the right regenerative proteins at the right time.

The system directs a lead to exactly the right position with the target organ and stimulates controlled expression of IGF-1 in combination with SDF-1, VEGF, HGH, HGF, Follistatin, and tropoelastin in the proper sequence to optimize repair and regeneration. Also, it can produce hearts, kidneys, livers, lungs, brains, pancreas, lung, skin, knees, and elbows, skin, penis, breasts, aorta, arteries, and limbs.

The version of the system discussed for this Example includes the following components: bioelectric regeneration stimulator (micro-stimulator from QIG Greatbatch); signal for causing controlled release of IGF-1: applied 20V at 1 Hz with a frequency of 5 ms for 24 hours; signal for causing controlled release of SDF-1; signal for causing controlled release of VEGF; signal for causing controlled release of HGH; signal for controlled release of HGF; signal for controlled release of follistatin; signal for controlled release of tropoelastin; pacing infusion lead to implant in organ or tissue to be treated; infusion and electrode wide area patch (optional); wireless transmitter for all signals listed above (optional); refillable micro pump (optional); external programmer; and external battery charger.

The regeneration stimulator may be implanted just below the skin of the patient or may be external, especially if the wireless option is chosen. For the implantable model, an infusion conduction lead is directed from the stimulator to the organ or tissue to be repaired. The tip of the lead is lodged into the tissue with a corkscrew or other fixation tip. The regeneration stimulator is programmed by an external programmer. The stimulator is programmed to cause release of specific regeneration proteins in a preferred sequence to optimize organ repair starting with VEGF, then SDF-1, then IGF-1, then HGH, then HGF, then follistatin, then tropoelastin. The wireless version is applied externally with the signal pointed to the organ to be regenerated. The signal may be constantly calibrated to adjust for fat, skin, and other obstacles between the signal generator and the organ of Interest to be treated. The device may be recharged with an external charger. In cases of very widespread organ damage, a wide array infusion and electrode patch may be used to cover the damaged organ area more completely. To accelerate the organ regeneration, an implantable, programmable, refillable micro infusion pump may be used to deliver various stem cells, nutrient hydrogels Micro RNA's and growth factors and (in some cases) drugs.

SDF-1 recruits via homing signal new reparative stem cells to the damaged organ, VEGF causes new nutrient and oxygen producing blood vessels to grow into the area being treated. IGF-1 repairs damaged cells, tissues and organs. Follistatin repairs damaged muscle. Tropoelastin adds elasticity to treated tissues making them more compliant. HGF aides in all repair processes and in the specific case of heart regeneration, reduces the risk of arrhythmias. All of these proteins work together to fully regenerate an organ over time. The process am be accelerated with the use of a micro infusion pump that is filled with various types of stem cells and growth factors and in some cases drugs.

The construction of electric signal generators, and pacemakers, are known to the art and can be obtained from OEM suppliers as well as their accompanying chargers and programmers. What is unique is the programming of specific signals to use specific protein expressions at precisely the right time for optimal organ regeneration. Pacing infusion leads may be purchased from a variety of OEM vendors. An infusion and electrode wide area pitch may be constructed by cutting conduction polymer to shape and forming plastic into a flat bag with outlet ports in strategic locations.

Any one of the protein expression signals work well on their own for organ regeneration, but they work better together. As previously identified herein, SDF-1 is the most powerful regeneration protein followed by IGF-1.

A wireless, single lumen infusion pacing lead or infusion conduction wide array patch may all be used to deliver the regeneration signals and substances to the organ of interest to be treated or they may be used in combination.

A bionic neuron ("BION") device (injectable microstimulator) may be adapted to provide the requisite stimulation. Such a device is typically the size of a long grain of rice (2 mm wide by 15 mm long) and comprises an integrated circuit chip sandwiched inside an antenna coil.

The regeneration stimulator lead or wireless signal is directed to the organ to be regenerated and the protein signals are delivered. Again, the most important is SDF-1 which recruits new stem cells to the site and its accompanying reverse polarity signal which triggers differentiation of the recruited stem cells into useful tissues.

The second most important is IGF-1, which is highly potent in cell repair. VE'GF helps grow in blood vessels for feeding the newly created and newly regenerated tissues.

Example—PDGF

Described herein is the bioelectric controlled expression of platelet derived growth factor (PDGF). PDGF is a powerful organ regeneration protein/cytokine. PDGF is one of the most potent growth factors in promoting cell, tissue and organ repair applicable to a wide variety of uses. It has been demonstrated to be especially useful in heart regeneration.

Described is the precise bioelectric signal for triggering PDGF expression from tissues. PDGF combined with the programmable micro-infusion pump and fifteen component organ regeneration composition is to help patients with degenerating and diseased organs to recover. Both wireless non-invasive and implantable wire lead based means may be utilized to get the regeneration and healing promoting bioelectric signals to organs.

PDGF constitute a family of four gene products (PDGF-A-D) acting by means of two receptor tyrosine kinases, PDGFRα and β. Three of the ligands (PDGF-A, PDGF-B, and PDGF-C) bind to PDGFRα with high affinity. PDGF signaling is essential for epicardial cell proliferation. PDGF signaling plays important roles in coronary vessel formation.

PDGF also induces DNA synthesis in cardiomyocytes. PDGF recruits stem/progenitor cells. PDGF can trigger controlled cell proliferation. PDGF can contribute to cell reprogramming and transformation into induced multipotent stem cells. PDGF downstream effects include regulation of gene expression and the cell cycle. PDGF can be used to create cell-specific antifibrotic compounds including those needed for liver regeneration. PDGFs are required for normal kidney development via recruitment of mesenchymal cells to both glomeruli and the interstitium. PDGF exerts essential roles from the gastrulation period to adult neuronal maintenance by contributing to the regulation of development of preplacodal progenitors, placodal ectoderm, and neural crest cells to adult neural progenitors, in coordinating with other factors. PDGF plays critical roles for maintenance of many specific cell types in the nervous system together with vascular cells through controlling the blood brain barrier homeostasis. PDGF modulates neuronal excitability through adjusting various ion channels, and affecting synaptic plasticity and function. PDGF stimulates survival signals, majorly P13-K/Akt pathway but also other ways, rescuing cells from apoptosis. PDGF in dendrite spine morphology is critical for memory in the developing brain. PDGF has been found to stimulate regeneration of periodontal tissues and bone. PDGF has been found to highly stimulate hair regeneration. PDGF signaling is essential in regeneration of hearts in animals. PDGF signaling induces DNA synthesis in the cells and is required for cardiomyocyte proliferation during heart regeneration. PDGF was used in biological pacemaker development, and it worked well to help form new sino atrial node cells from atrial myocytes. PDGF has been found useful in regeneration of other organs such as eyes, lungs, kidneys, brains, hair and aortas.

Described is an organ regeneration device that produces controlled release of PDGF by bioelectric stimulation. Failing organs cannot produce enough PDGF to fully regenerate.

Other devices only provide one time delivery of PDGF, which is insufficient to fully regenerate a failing organ. Infusion systems lose too much therapeutic agent.

The system provided herein provides controlled sustained and repeated delivery of PDGF via a wire conduction lead or wireless signal delivery and may be combined with a micro infusion pump for maximum results in severe organ failure cases.

The bioelectric stimulator preferably reads the needs of an organ and produces release of PDGF in just needed amounts to enhance organ regeneration. Researchers previously conducted organ regeneration studies of one time injection of PDGF with a needle and syringe. This is impractical and will not work for major organ repair.

A onetime dose is not enough to fully regenerate an organ. To access the organ with a needle and syringe is very invasive, dangerous and painful. Injected or infused PDGF has a high wash out loss rate.

The system provides controlled sustained and repeated release of PDGF via, e.g., a wire conduction lead or wireless signal delivery and may be combined with a micro infusion pump for maximum results in severe organ failure cases.

Also, it can produce the device may also be used for organ enhancement instead of just organ repair such as brain function enhancement.

The version of the system discussed for this Example includes the following components: micro bioelectric signal generator; programming wand; programming computer; pacing infusion lead; micro infusion pump; PDGF bioelectric signal program; PDGF solution; organ reading device and processor; organ reading software program and analysis software; and wireless energy beam transmitter.

Relationship Between the Components:

The micro bioelectric stimulator is programmed with the programming wand connected to the programming computer with the PDGF bioelectric signal of 20V, 50 Hz, and 0.2 amps. The micro stimulator is connected to the pacing infusion lead and the other side of that lead is affixed in the central portion of the damaged or diseased target organ. The programming wand connected to the programming computer can active the micro bioelectric stimulator to become an organ reading device. When programmed with the organ reading and analysis software the organ reader is able to read all the bioelectric activity of the failing organ as well as its phenotype, genotype including genetic defects and variation and chemical and biologically metabolism.

The bioelectric stimulation controlled PDGF expression causing new blood vessels to grow into the failing organ(s) and new healthy organ tissue to form. The reader adjusts the therapeutic dose as needed. The micro infusion pump refilled daily with a mixed stem cell based composition that includes PDGF and may also include SDF-1, IGF, EGF, HGF, HGH, Activin A and B, eNOS, VEGF, follistatin, tropoelastin. GDF-10, GDF-11 and Neurogenin-3, selected alkaloids, and selected anti-inflammatory factors may be used to supplement the bioelectric stimulation therapy for organ repair in seriously failing organs.

If the organ failure is severe, an added programmable, implantable, re-fillable micro infusion pump may be added to the therapy. The micro pump is refilled daily with about 2 ml of stem cell-based organ regeneration composition that includes PDGF. If it is not easy or desirable to reach the organ to be treated with a wire-based pacing infusion lead, the operator may utilize a wireless energy beam transmitter to deliver the bioelectric regeneration signals wirelessly to the organ.

In this embodiment, the stimulator, lead, and programmer are essential. The micro infusion pump and mixed organ regeneration composition are optional.

The micro stimulator, and if chosen, the micro infusion pump are implanted somewhere below the skin of the patient with the pump silicone septum ports accessible for refilling just below the skin. The stimulator must be in a location reachable by the programming wand attached to a portable computer. The pacing infusion lead form the stimulator and pump is directed to the central damaged portion of the damaged organ i.e., heart, kidney, pancreas, liver. The micro stimulator may optionally be non-invasive and external and can deliver its signal to the failing organ via a focalized wireless energy beam. Much like how they focalize radiation to treat cancer tumors, but this energy stimulates organ regeneration.

Additionally: The micro stimulator may be programmed for additional protein expressions. The micro pump may be used a stand-alone device. The sequence of use may be changed.

The device may also be used for organ enhancement instead of just organ repair such as brain function enhancement.

Two PDGF expression control signals. One low voltage and one higher voltage. The test tissue is sheep heart tissue, while the test cells are mesenchymal stem cells. 30% PDGF increase with 3 V/cm, 10 Hz, 2 micro amps (0.000002 amps) and the pulse duration 0.2 ms. 230% PDGF increase with 20 V/cm 100 Hz, 0.25 mA ($2.5e^{-7}$ amps) and pulse duration of 40 pulses/s, width of 100 μs.

Example—Treating Cancer Tumors Using Bioelectric Stimulation in Combination with Micro Infusion Previous cancer treatments failed to address the combination of stopping cell proliferation and blood supply followed by regenerating the damaged tissue or organ.

Cytokine and Chemotherapeutic and regenerative treatment for certain cancers may be combined with low intensity, intermediate frequency alternating electric fields that are tuned to release specific beneficial proteins at specific time intervals. More specifically, cell proliferation inhibition and halting blood supply to tumors in the first treatment stage. The bioelectric stimulation treatment may be increased in volume and efficacy by the combination use of an implantable, programmable, re-fillable micro infusion pump that delivers anti-cell proliferation and anti-blood vessel growth proteins as well, if desired, standard cancer treatment drugs such as chemo therapy agents. The second stage of treatment is focused regeneration of cancer damaged tissues back to their most optimal healthy state. The regenerative phase comprises a sequence of recruiting reparative stem cells to the damaged organ by bioelectrically stimulating the release of SDF-1 (stem cell homing factor), followed by a controlled proliferation signal, a controlled blood vessel supply signal (VEGF) and if desired and useful release of Follistatin, tropoelastin, HGF, IGF-1 and Activin. The stimulation cycle causing release of beneficial proteins for regeneration may be upgraded in volume and speed of delivery by the combination use of an implantable, re-fillable, programmable micro infusion pump for delivering a higher quantity of stem cells, nutrient hydrogel, matrix and beneficial tissue and organ regeneration promotion proteins.

Cytokine and Chemotherapeutic and regenerative treatment for certain cancers comprising a combination low intensity, intermediate frequency alternating electric fields that are tuned to release particular beneficial proteins in two stages, stage (1) is stopping cancer spread by halting cell proliferation and halting tumor blood supply and stage (2) regenerating the cancer damaged tissue or organ back to optimal health. In many cases, the resulting cell proliferation inhibition is significantly higher than the inhibition obtained by drug-only regimens of treatment.

A method of killing or inhibiting the growth of cancer cells in a target region followed by regenerating the tissue or organ back to optimal health, the method comprising the steps of:

Stage 1=Stop cancer growth by:

Applying, to the target region, a series of bioelectric signals that damages the cancer cells or inhibits the growth of the cancer cells via stopping cell proliferation and halting blood supply temporarily, but leaves normal cells in the target region substantially unharmed; and Treating the cancer cells with another anti-cancer regimen via programmable micro pump infusion, wherein the applying step and the treating step are performed simultaneously.

Stage 2=Regeneration of post cancer tissue or organ by:
- Treating the target region with a series of bioelectric signals to recruit stem cells, grow healthy blood vessels and re-grow healthy functional tissues in the previous cancer damaged region In such a method, in the applying step, the field may be applied in at least two different directions in an alternating sequence to halt cell proliferation and to stop blood supply to the tumor.

In such a method, the other anti-cancer regimen may comprise treating the cancer cells with an anti-cancer drug. In this method, the drug may comprise at least one drug selected from the group consisting of paclitaxel, doxorubicin cyclophosphamide, and cisplatin. In such a case, the drug dosage may be less than 20% of a standard dosage for the drug.

In such a method, the bioelectric stimulation may release any one of these regeneration of tissue and organ beneficial proteins SDF-1, IGF-1, Activin, HGF, VEGF, Follistatin or tropoelastin and in specific sequences for optimal organ health.

In such a method, all bioelectric regeneration signal may be delivered wirelessly and/or non-invasively.

In such a method, the target cancer may be breast cancer and the target regenerative organ may be breast reconstruction.

In such a method, the target cancer may be brain cancer and the target regenerative organ is brain.

In such a method, the target cancer may be prostate cancer and the target regenerative organ may be the prostate.

In such a method, the target cancer may be colon cancer and the target regenerative organ may be the colon.

In such a method, the target cancer may be throat or esophageal cancer and the target regenerative organ may be throat or esophagus.

In such a method, the target cancer may be pancreas cancer and the target regenerative organ may be the pancreas with improved insulin production.

In such a method, the target cancer may be lung cancer and the target regenerative organ may be lung(s).

In such a method, the target cancer may be eye cancer and the target regenerative organ may be the eye.

Example—a Combination Protein Expression Stimulator, Micro Infusion Pump, and Fifteen (15) Component Stem Cell-Based Composition for Saving Brain Function in a Subject Following Stroke or Injury Brain function is lost when a stroke or brain injury occurs in a subject due to lack of oxygen and nutrients reaching a particular portion of the brain. Prior art therapies are typically drugs that do nothing to regenerate lost brain tissue. Chemical drugs do not do anything to affect neurogenesis (the growth of new brain tissue to replace damaged brain tissue). For example, the most popular simply dissolves blood clots, stopping further damage, but doing nothing to recover brain tissue already lost.

Prior art electrical stimulation devices do not have the correct signals for homing stem cells or for regenerating brain tissue. Existing electrical stimulation devices deliver one signal and that signal does not promote regeneration of lost brain tissue. Burst electrical pulses of old-type stimulators do nothing to affect neurogenesis.

Prior art one-time stem cell injections of one type of stem cell or modified stem cell have achieved some success, but this therapy is limited and incomplete. One-time needle injection cell therapies are too limited to recover major lost brain function. One-time injection of stem cells on a stand-alone basis mostly die out without a support system and cannot affect major neurogenesis.

The herein described combination of bioelectric stimulation of ten (10) key regeneration proteins via bioelectric signals, 24 hours a day for seven days a week, combined with daily or weekly infusions of the herein described fifteen component compositions provides much more complete repair, recovery, and regeneration of lost brain function.

The herein described device, method, and system practice all forms of “good farming” to grow a “new crop” of functional brain tissue in the skulls of post-stroke and post-injury subjects.

The herein described system rapidly and easily delivers ten (10) brain regeneration promoting bioelectric signals to the subject within minutes, combined with a micro infusion pump that delivers fifteen (15) component angiogenic and regeneration compositions rapidly and safely. This, in combination, can fully restore brain functionality back to normal.

The ten (10) key regeneration proteins are SDF-1 (stem cell homing signal), IGF—(1 DNA repair and brain regeneration signal), HGF, EGF, Activin A and B, eNOS, VEGF, follistatin, and tropoelastin signal as described herein.

The system discussed in this Example preferably includes: the bioelectric signal generator, a programmable, re-fillable micro infusion pump, a brain saving helmet with electroacupuncture needles built in, micro infusion leads stereotaxic directed to deep brain regions, a fifteen component angiogenic composition, a fifteen component regeneration composition, human placenta, fetal serum, a cell proliferation signal, and a cell controlled differentiation signal.

In use, the bioelectric signal generator and the micro infusion pump are both attached to the brain saving helmet with electroacupuncture needles (not shown). The helmet is placed on the head of the patient. If the brain saving helmet with electroacupuncture needles is not used, one may use “off the shelf” standard, readily available electro-acupuncture needles. The bioelectric signal generator stimulator is activated and the micro infusion pump is filled with first the fifteen component angiogenic composition to increase blood flow and then the next day with the fifteen component regeneration composition.

The bioelectric stimulator cycles through the SDF-1 signal for stem cell homing, then IGF-1 for DNA repair, then HGF, EGF, Activin A and B, eNOS, VEGF, follistatin, tropoelastin, cell proliferation, and cell differentiation. The micro infusion pump may be re-loaded with fetal serum and placenta in severe cases to enhance results. Anti-inflammatory agents may also be used. The bioelectric signal generator stimulator recruits stem cells, causes release of regeneration support factors, and multiples cells, and then controls their differentiation into healthy full functioning brain tissue.

The micro infusion pump is filled daily or week with the fifteen component angiogenic and regeneration compositions designed to facilitate neurogenesis. The fifteen component angiogenic and regenerative compositions provide much more complete repair, recovery, and regeneration of lost brain function.

If electrical stimulation alone does not work, the micro pump is filled with angiogenic and regeneration compositions for daily delivery. If those compositions do not work, then fetal serum and placenta may be added.

A bioelectric signal generator can be as described otherwise herein. For some signals, a drop down resistor in the pacing infusion lead may be necessary to drop the lowest voltage and current from the standard pacemakers down to a natural micro voltage level (the same level of natural electricity in a human body). A micro infusion pump can be as described otherwise herein and may be sourced from various drug delivery pump manufacturers and adapted by taking any filters out. The compositions for angiogenic and regeneration purposes are comprised of mixing together components that can be obtained from a person's own body as described herein further processed in a standard cell culturing laboratory (many contract manufacturers are available) or from reliable known suppliers.

The bioelectric signal generator is essential. All other components may be optional. The micro infusion pump, compositions, fetal serum, placenta, and anti-inflammatory agents are only necessary if the bioelectric stimulation on its own has not restored complete function or (e.g., in emergency recovery cases) where time is of the essence such as in an acute stroke situation.

One could use the compositions on their own injected by needle syringe. One could use the micro infusion pump on its own filled with other mixes of stem cells or drugs. One could use the bioelectric stimulator on its own running only one or a few signal programs instead of all of them, or one could program the bioelectric stimulator for entirely different signaling.

Upon arrival to the location of an acute stroke patient, a rapid assessment is made including video phone examination of the patient. A clot dissolving drug is first administered. Then, the brain-saving helmet is placed on the patient's head, and the bioelectric signal generator is turned on running though all ten (10) regeneration signals and the micro infusion pump is loaded first with an angiogenic composition followed immediately thereafter with a regeneration composition. If normal brain function is not restored in the subject with the above steps, the micro infusion pump may be re-filled with fetal serum, placenta, and anti-inflammatory agents, which are then administered.

EXAMPLE

In bioelectric stimulation tissue studies, a 2000% and increase in IL-6 was achieved. IL-6 is a key promoter of regeneration. With respect to IL-6, Mosteiro et al. (2016) shows that tissue damage is a relevant factor for cells to go back to an embryonic state. Nobel Prize winner Shinya Yamanaka opened the door to regenerative medicine by cell reprogramming, based on introducing a combination of four genes known as OSKM (for genes, OCT4, SOX2, KLF4, and MYC), which reverts adult cells to an embryonic-like state, and transforms these cells into pluripotent cells. Cell reprogramming was later achieved within a living organism (i.e., a mouse) in 2013.

Mosteiro et al. (2016) analyzes what happens in living tissues when reprogramming is induced using OSKM. OSKM was found to be inefficient at inducing reprogramming or pluripotency in the highly specialized cells that constitute adult tissues. Tissue damage plays a critical role by complementing the activity of the OSKM genes.

This relationship between damage and reprogramming is mediated by the proinflammatory molecule, interleukin-6 (IL-6). Without IL-6 presence, the OSKM genes are far less efficient at inducing the reprogramming process. These findings suggest the following sequence of events: the expression of the OSKM genes results in damage to the cells; accordingly, they secrete IL-6; the presence of this molecule induces the reprogramming of some neighboring cells.

Both wireless non-invasive and/or implantable wire lead ("electrode") based means may be used to deliver the regeneration and healing promoting bioelectric signals to target organs.

The controlled expression of Hypoxia Inducible Factor 1 (HIF-1 Alpha or "HIF-1a") for, e.g., promoting organ regeneration (particularly liver regeneration) is also described herein. HIF-1 Alpha is a powerful organ regeneration protein. A more than 286% increase of HIF-1 Alpha on demand in test article tissues was achieved with a specific, optimized bioelectric signal. In other experiments, a 2300% increase in expression of HIF-1 Alpha was achieved.

Hypoxia has been proven as a critical element in the organ regeneration process. HIF-1a is a master regulator of the adaptive response to hypoxia. HIF-1a over expression in cells mimics the mechanisms triggered by hypoxia in injured or diseased tissues and increases their therapeutic potential without direct hypoxia stimulation.

Potential useful properties of HIF-1a for organ regeneration include: HIF-1a signaling promotes heart regeneration, HIF-1a signaling reduces infarction size and attenuates cardiac dysfunction, HIF-1a induces coronary collateral vessel formation, HIF-1a is a tumor suppressor, HIF-1a has been reported a gateway controller of cancer, HIF-1a promotes liver regeneration, HIF-1a promotes lung regeneration via alveolar development, HIF-1a promotes brain saving following traumatic brain injury or stroke, HIF-1a promotes retinal eye regeneration, HIF-1a management seems to be important to healthy kidney function and can protect against kidney injury, HIF-1a helps promote muscle regeneration, HIF-1a helps promote wound healing, HIF-1a has a supportive role in hair regeneration, HIF-1a promotes extracellular matrix, HIF-1a has a critical role in bone development and healing, HIF-1a may be important to stabilize teeth positions after accelerated tooth movement, and HIF-1a is an essential regulator of inflammation.

REFERENCES (The contents of the entirety of each of which is incorporated herein by this reference.)

Thattaliyath et al. "Modified Skeletal Myoblast Therapy For Cardiac Failure Using AAV SDF1," *Proc. Intl. Soc. Mag. Reson. Med.* 16, page 579 (2008).

Prochazka et al. "Cocktail of Factors from Fat-derived Stem Cells Shows Promise for Critical Limb Ischemia" http://www.sciencenewsline.com/news/2016012204520017.html (Jan. 21, 2016).

Wei et al. "Epicardial FSTL1 reconstitution regenerates the adult mammalian heart," *Nature* 525: 479-485 (24 Sep. 2015).

"Hearts build new muscle with this simple protein patch," jacobsschool.ucsd.edu/news/news_releases/release.sfe?id=1813 (Sep. 16, 2015).

Stenn et al. "Bioengineering the Hair Follicle," *Organogenesis,* 3(1): 6-13 (January-March 2007).

Salcedo et al. "Low current electrical stimulation upregulates cytokine expression in the anal sphincter," *Int. J. Colorectal Dis.,* 2012 February; 27(2):221-5. doi: 10.1007/s00384-011-1324-3. Epub (October 2011).

Marie Ellis "Cure for baldness? Stem cells bring hope" medicalnewstoday.com/articles/271898.php.

Alice Park "Shrinking Stem Cells Are the Real Reason for Hair Loss" Time, (Feb. 5, 2016).

Robert Ferris "Battle against baldness turns to stem cells" cnbc.com/2015/01/29/studies-indicate-its-possible-to-use-stem-cells-to-cure-baldness.html (Jan. 29, 2015).

"Control of pelage hair follicle development and cycling by complex interactions between follistatin and activin," *FASEB J.* (Jan. 2, 2003).

Chen et al. "Regenerative Hair Waves in Aging Mice and Extra-Follicular Modulators Follistatin, Dkk1, and Sfrp4," *Journal of Investigative Dermatology*, August 2014, Volume 134, Issue 8, Pages 2086-2096.

Li et al. "Exogenous IGF-1 promotes hair growth by stimulating cell proliferation and down regulating TGF-β1 in C57BL/6 mice in vivo," *Growth Hormone & IGF Research, Volume* 24, *Issues* 2-3, Pages 89-94 (April-June 2014).

"Our Approach to Improve Hair Loss by Increasing Hair Growth Factor IGF-1," jhgc.com.sg/theory/igf-1/index-.html.

Hy et al. "Insulin-like growth factor 1 and hair growth," *Dermatol. Online J.;* 5(2):1 (November 1999).

Lee et al. "Hepatocyte growth factor (HGF) activator expressed in hair follicles is involved in in vitro HGF-dependent hair follicle elongation," *J. Dermatol. Sci.,* 25(2):156-63 (February 2001).

Fukuoka and Suga, "Hair Regeneration Treatment Using Adipose-Derived Stem Cell Conditioned Medium: Follow-up With Trichograms," *Eplasty,* 15: e10 (March 2015).

Fukuoka et al. "The Latest Advance in Hair Regeneration Therapy Using Proteins Secreted by Adipose-Derived Stem Cells," *The American Journal of Cosmetic Surgery,* 29(4):273-282 (2012).

"Reversing Age-Related Hair Loss and Restoring Healthy Hair Growth in Men and Women" nutritionreview.org/2015/08/reversing-age-related-hair-loss-and-restoring-healthy-hair-growth-in-men-and-women/(Aug. 24, 2015).

Yamakazi et al. "Hair cycle-dependent expression of hepatocyte growth factor (HGF) activator, other proteinases, and proteinase inhibitors correlates with the expression of HGF in rat hair follicles," *J. Investig. Dermatol. Symp. Proc.,* 4(3):312-5 (December 1999).

"Involvement of hepatocyte growth factor/scatter factor and Met receptor signaling in hair follicle morphogenesis and cycling," *FASEB J.*, February 2000 14:319-332.

"Interesting study about prolactin, VEGF and angiogenic inhibition," regrowth.com/hair-loss-forums/topic/interesting-study-about-prolactin-vegf-and-angiogenic-inhibition/(November 2006).

"Control of Hair Growth by a Growth Factor Protein," hairloss-reversible.com/control-of-hair-growth-by-a-growth-factor-protein/.

"Hair Growth Factors," Nanogen, svijet-kose.com/dokumenti/Serum-vegf.pdf.

"Blood Vessels Hold Key To Thicker Hair Growth," sciencedaily.com/releases/2001/02/010215074636.htm (February 2001).

Jia et al. "Activin B Promotes Initiation and Development of Hair Follicles in Mice," *Cells Tissues Organs,* 198:318-326 (February 2014).

"Elastatropin® in Scalp & Hair Conditioning," proteingenomics.com/haircare.html.

"What Is Elastin?" keracyte.com/index.php/site/page?view=whatIsElastin Park et al. "Effects of SM-215 on Hair Growth by Hair Follicle Stimulation," *Indian Journal of Science and Technology*, Vol 8(25), DOI: 10.17485/ijst/2015/v8i25/80263, (October 2015).

Thattaliyath et al. "Modified Skeletal Myoblast Therapy For Cardiac Failure Using AAV SDF1," *Proc. Intl. Soc. Mag. Reson. Med.* 16, p. 579 (2008).

"Electrical brain stimulation could support stroke recovery," sciencedaily.com/releases/2016/03/160316151108.htm (Mar. 16, 2016).

"Electric Tumor Treatment Fields," No. 0827 Policy, aetna.com/cpb/medical/data/800_899/0827.html (Nov. 18, 2016).

D. Grady "Electrical Scalp Device Can Slow Progression of Deadly Brain Tumors," New York Times, https://www.nytimes.com/2014/11/16/health/electrical-scalp-device-can-slow-progression-of-deadly-brain-tumors.html?_r=0 (Nov. 15, 2014).

B. Borgobello "FDA approves the treatment of brain tumors with electrical fields," *New Atlas*, http://newatlas.com/treatment-of-brain-tumors-with-electrical-fields/21433/ (Feb. 13, 2012).

Hopkins Medicine "Overview of Pacemakers and Implantable Cardioverter Defibrillators (ICDs)," hopkinsmedicine.org/healthlibrary/conditions/cardiovascular_diseases/overview_of_pacemakers_and_implantable_cardioverter_defibrillators_icds_85,P00234/.

Medtronic "Cardiac Resynchronization Therapy (CRT) Devices For Heart Failure," medtronic.com/us-en/patients/treatments-therapies/crt-devices.html.

Columbia "Implant Procedure Concepts—Pacemaker, ICD and CRT Overview," columbia.edu/itc/hs/medical/hickey/docs/Pacemaker,%20ICD %20 and %20CRT %200verview %2 0022007.pdf "FDA Approves Algovita Spinal Cord Stimulation System from Greatbatch," http://www.odtmag.com/contents/view_breaking-news/2015-12-02/fda-approves-algovita-spinal-cord-stimulation-system-from-greatbatch (Dec. 2, 2015).

Mass Device "Greatbatch wins FDA PMA for Algovita SCS," http://www.massdevice.com/greatbatch-wins-fda-pma-for-algovita-scs/(Dec. 1, 2015).

P. Banerjee "Electrical muscle stimulation for chronic heart failure: an alternative tool for exercise training?" *Curr. Heart Fail. Rep.,* 7(2):52-8. doi: 10.1007/s11897-010-0013-9 (June 2010).

H N Sabbah "Electrical vagus nerve stimulation for the treatment of chronic heart failure," *Cleve. Clin. J. Med.,* 78 Suppl. 1:524-9. doi: 10.3949/ccjm.78.sl.04 (August 2011).

Bio-Leonhardt "Micro Stimulator" bioleonhardt.com/micro-stimulator/.

H U Klein "Vagus Nerve Stimulation: A new approach to reduce heart failure" *Cardiology Journal* (2010).

"Israeli innovation uses nerve stimulation to treat heart failure" israel21c.org/israeli-innovation-uses-nerve-stimulation-to-treat-heart-failure/(Feb. 11, 2007).

Sahoo and Losordo "Exosomes and Cardiac Repair After Myocardial Infarction," *Circulation Research,* 114:333-344 (Jan. 16, 2014).

Tamaki et al. "Cardiomyocyte Formation by Skeletal Muscle-Derived Multi-Myogenic Stem Cells after Transplantation into Infarcted Myocardium," *PLoS ONE* 3(3): e1789. doi:10.1371/journal.pone.0001789 (March 2008).

W. Hoffmann "Regeneration of the gastric mucosa and its glands from stem cells," *Curr. Med. Chem,* 15(29):3133-44 (2008).

Cerrada et al. "Hypoxia-Inducible Factor 1 Alpha Contributes to Cardiac Healing in Mesenchymal Stem Cells-Mediated Cardiac Repair," *Stem Cells and Development,* 22(3): 501-511 (2013).

Fatemi et al. "Imaging elastic properties of biological tissues by low-frequency harmonic vibration" *Proceedings of the IEEE,* 91(10):1503-1519 (October 2003) DOI: 10.1109/JPROC.2003.817865.

Guimarães-Camboa & Evans "Redox Paradox: Can Hypoxia Heal Ischemic Hearts?" *Cell,* 39(4):392-394, (21 Nov. 2016) DOI: http://dx.doi.org/10.1016/j.devcel.2016.11.007

Huang et al. "Myocardial transfection of hypoxia-inducible factor-1a and co-transplantation of mesenchymal stem cells enhance cardiac repair in rats with experimental myocardial infarction", *Stem Cell Research & Therapy* 5:22 (2014) DOI: 10.1186/scrt410

Kido et al. "Hypoxia-Inducible Factor 1-Alpha Reduces Infarction and Attenuates Progression of Cardiac Dysfunction After Myocardial Infarction in the Mouse" *JACC*, Volume 46, Issue 11, 6 Dec. 2005, Pages 2116-2124. https://doi.org/10.1016/j.jacc.2005.08.045.

Mosteiro et al. "Tissue damage and senescence provide critical signals for cellular reprogramming in vivo." *Science,* 2016; 354 (6315): aaf4445 DOI: 10.1126/science.aaf4445

Tajima et al. "HIF-1alpha is necessary to support gluconeogenesis during liver regeneration" *Biochem Biophys Res Commun.* 2009 Oct. 2; 387(4):789-94. doi: 10.1016/j.bbrc.2009.07.115. Epub 2009 Jul. 28.

Tamaki et al. "Cardiomyocyte Formation by Skeletal Muscle-Derived Multi-Myogenic Stem Cells after Transplantation into Infarcted Myocardium," *PLoS ONE* 3(3): e1789. doi:10.1371/journal.pone.0001789 (2008).

What is claimed is:

1. A method of using a bioelectric stimulator to stimulate target tissue of a subject to control stem cell homing, proliferation, or differentiation and/or upregulate expression of at least one protein by the target tissue, wherein the protein is selected from the group consisting of activin, epidermal growth factor (EGF), follistatin, hepatocyte growth factor (HGF), insulin-like growth factor 1 (IGF-1), platelet-derived growth factor (PDGF), receptor activator of nuclear factor kappa-B ligand (RANKL), stromal cell-derived factor 1 (SDF1), tropoelastin, vascular endothelial growth factor (VEGF) and any combination thereof, the method comprising:

delivering at least one bioelectric signal to the target tissue so as to control stem cell homing, proliferation, or differentiation and/or to upregulate expression of at least one protein in the target tissue, wherein the bioelectric signal(s) comprise(s) at least one bioelectric signal(s) selected from the group consisting of (a) 2 Hz, square biphasic wave, pulse width 1,000 μs so as to upregulate expression of RANKL by the target tissue;

(b) within 15%, 30 Hz, square biphasic wave, pulse width 100 μs so as to upregulate expression of SDF1 to the target tissue and stimulate stem cell homing to the target tissue;

(c) within 15%, 100 Hz, square biphasic wave, pulse width 100 μs so as to upregulate expression of PDGF and stimulate stem cell homing to the target tissue;

(d) 20 Hz, square wave, pulse width 200 to 700 μs so as to stimulate stem cell proliferation;

(e) 10 Hz, square biphasic wave, pulse width 200 μs so as to upregulate expression of PDGF by the target tissue and stem cell homing to the target tissue;

(f) within 15%, 150 Hz, monophasic square wave, pulse width 100 μs so as to upregulate expression of activin by the target tissue;

(g) within 15%, 500 Hz, square biphasic wave, pulse-width 180 μs so as to upregulate expression of EGF by the target tissue;

(h) within 15%, 22 Hz, square monophasic wave, pulse width 50% duty cycle so as to upregulate expression of IGF-1 by the target tissue;

(i) 70 Hz, square wave, pulse width 10%-50% duty cycle, (j) 200 picoamps with a pulse having an amplitude of 5 V and a width of 0.5 milliseconds so as to stimulate stem cell proliferation;

(k) 50 Hz, square wave so as to upregulate expression of follistatin, tropoelastin, VEGF and HGF by the target tissue, and (l) any combination(s) thereof.

2. The method according to claim 1, further comprising: separately delivering to the subject an admixture comprising any combination of the following: stem cells, endothelial progenitor cells, selected exosomes, selected alkaloids, selected anti-inflammatory agents, nutrient hydrogel, organ specific matrix, selected growth factors, amniotic fluid, placenta fluid, cord blood, and embryonic sourced growth factors and cells.

3. The method according to claim 1, wherein the target tissue is selected from the group consisting of brain, scalp, eye, ear, skin, tooth, dental gum, tooth root, sub-mucosa, breast, aorta, limb, artery, heart, heart valve, kidney, pancreas, bladder, liver, joint, bone, and any combination thereof.

4. The method according to claim 1, wherein the bioelectric signal(s) comprise(s): a signal of 2 Hz, square biphasic wave, pulse width 1,000 μs so as to upregulate expression of RANKL.

5. The method according to claim 1, wherein the bioelectric signal(s) comprise(s), within 15%, 30 Hz, square biphasic wave, pulse width 100 μs so as to upregulate expression of SDF-1.

6. The method according to claim 1, wherein the bioelectric signal(s) comprise(s): a signal of 100 Hz, square biphasic wave, pulse width 100 μs so as to upregulate expression of PDGF.

7. The method according to claim 1, wherein the bioelectric signal(s) comprise(s): a signal of 20 Hz, square wave, pulse width 200 to 700 μs so as to increase stem cell proliferation.

8. The method according to claim 1, wherein the bioelectric signal(s) comprise(s): a signal of 10 Hz, square biphasic wave, pulse width 200 μs so as to upregulate expression of PDGF.

9. The method according to claim 1, wherein the bioelectric signal(s) comprise(s), within 15%, 150 Hz, monophasic square wave, pulse width 100 μs so as to upregulate expression of activin.

10. The method according to claim 1, wherein the bioelectric signal(s) comprise(s), within 15%, 500 Hz, square biphasic wave, pulse-width 180 μs so as to upregulate expression of EGF.

11. The method according to claim 1, wherein the bioelectric signal(s) comprise(s), within 15%, 22 Hz, square monophasic wave, pulse width 50% duty cycle so as to upregulate expression of IGF-1.

12. The method according to claim 1, wherein the bioelectric signal(s) comprise(s) a signal of 70 Hz, square wave, pulse width 10%-50% duty cycle so as to increase stem cell proliferation.

13. The method according to claim 1, wherein the bioelectric signal(s) comprise(s) a signal of 200 picoamps with a pulse having an amplitude of 5 V and a width of 0.5 milliseconds so as to induce stem cell differentiation.

14. The method according to claim 1, wherein the bioelectric signal(s) comprise(s), within 15%, 50 Hz, square wave so as to upregulate expression of follistatin, tropoelastin, and/or VEGF.

15. The method according to claim 1, wherein the bioelectric signal(s) comprise(s): a signal of within 15%, 50 Hz, square biphasic wave, pulse width 100 μs, with surge delivery of 10 seconds on and 30 seconds off so as to upregulate expression of HGF.

* * * * *